US012286663B2

(12) United States Patent
Hu et al.

(10) Patent No.: US 12,286,663 B2
(45) Date of Patent: Apr. 29, 2025

(54) TRANSFORMANT FOR PRODUCING DODECANEDIOIC ACID AND METHOD FOR PRODUCING DODECANEDIOIC ACID

(71) Applicants: NATIONAL TSING HUA UNIVERSITY, Hsinchu (TW); Chang Chun Plastics Co., Ltd., Taipei (TW); Chang Chun Petrochemical Co., LTD., Taipei (TW); DAIREN CHEMICAL CORP., Taipei (TW)

(72) Inventors: Yu-Chen Hu, Hsinchu (TW); Nam Ngoc Pham, Hsinchu (TW); June-Yen Chou, Taipei (TW); Hsing-Yun Wang, Taipei (TW); Vincent Jianan Liu, Taipei (TW)

(73) Assignees: NATIONAL TSING HUA UNIVERSITY, Hsinchu (TW); Chang Chun Plastics Co., Ltd., Taipei (TW); Chang Chun Petrochemical Co., LTD., Taipei (TW); DAIREN CHEMICAL CORP., Taipei (TW)

( * ) Notice: Subject to any disclaimer, the term of this patent is extended or adjusted under 35 U.S.C. 154(b) by 0 days.

(21) Appl. No.: 18/189,272

(22) Filed: Mar. 24, 2023

(65) Prior Publication Data
US 2024/0110208 A1   Apr. 4, 2024

(30) Foreign Application Priority Data

Sep. 29, 2022   (TW) .................... 111137112

(51) Int. Cl.
*C12P 7/6409* (2022.01)
*C12N 15/52* (2006.01)
*C12N 15/90* (2006.01)

(52) U.S. Cl.
CPC .......... *C12P 7/6409* (2013.01); *C12N 15/52* (2013.01); *C12N 15/905* (2013.01); *C12Y 101/01* (2013.01); *C12Y 101/0302* (2013.01); *C12Y 114/14* (2013.01); *C12Y 207/01086* (2013.01)

(58) Field of Classification Search
CPC ..... C12P 7/6409; C12N 15/52; C12N 15/905; C12Y 114/14
See application file for complete search history.

(56) References Cited

U.S. PATENT DOCUMENTS

2019/0010524 A1* 1/2019 Laplaza ................ C12N 15/81

OTHER PUBLICATIONS

Okazaki, K. "Peroxisomal acyl-coenzyme A oxidase multigene family of the yeast Candida tropicalis; nucleotide sequence of a third gene and its protein product." Gene, 58: 37-44. (Year: 1987).*

Wheeler and Mathews, "Effects of a Mitochondrial Mutator Mutation in Yeast POS5 NADH Kinase on Mitochondrial Nucleotides." The Journal of Biological Chemistry, 287(37): 31218-31222 (Year: 2012).*
Cao et al. "High-level productivity of alpha, omega-dodecanedioic acid with a newly isolated Candida viswanathii strain." J Ind Microbiol Biotechnol. 44:1191-1202. (Year: 2017).*
Lee et al. "Biotransformation of dicarboxylic acids from vegetable oil-derived sources: current methods and suggestions for improvement." Applied Microbiology and Biotechnology. 103:1545-1555. (Year: 2019).*
Zhang, L et al. "Development of an efficient genetic manipulation strategy for sequential gene disruption and expression of differnt heterologous GFP genes in Candida tropicalis." Biotechnology and Bioengineering 2020; 117:531-542. (Year: 2019).*
Ilmen et al., "Production of L-lactic acid by the yeast Candida sonorensis expressing heterologous bacterial and fungal lactate dehydrogenases." Microbial Cell Factories, 12:53. (Year: 2013).*
Lu et al., "CRISPR-based metabolic engineering in non-model microorganisms." Current Opinion in Biotechnology. 75 (Year: 2022).*
"Popular Promoters" Vector Builder. Downloaded Feb. 28, 2024. https://en.vectorbuilder.com/resources/vector-component/promoter.html (Year: 2014).*
Lombardi et al., "Plasmin-Based CRISPR-Cas9 Gene Editing in Multiple Candida species." mSphere, 4:2:e00125-19. (Year: 2019).*
ABSS Sequence Alignment 1. downloaded Jul. 1, 2024, p. 10, <https://abss.uspto.gov/abss4examiners/>. (Year: 2019).*
ABSS Sequence Alignment 2. downloaded Jul. 1, 2024, p. 10, <https://abss.uspto.gov/abss4examiners/>. (Year: 2019).*
Pham, et al., "Rational genome and metabolic engineering of Candida viswanathii by split CRISPR to produce hundred grams of dodecanedioic acid", Metabolic Engineering 77, pp. 76-88 (2023).
Yujie Li et al., "Development of a gRNA Expression and Processing Platform for Efficient CRISPR-Cas9-Based Gene Editing and Gene Silencing in Candida tropicalis", Microbiology Spectrum, vol. 10, Issue 3, pp. 1-14 (May 11, 2022).

(Continued)

*Primary Examiner* — Suzanne M Noakes
*Assistant Examiner* — Ciara A McKnight
(74) *Attorney, Agent, or Firm* — McBee Moore & Vanik, IP, LLC

(57) ABSTRACT

A gene editing system of *Candida viswanathii* includes a *Candida viswanathii*, a first gene editing fragment and a second gene editing fragment. The first gene editing fragment successively includes a first homology arm and a screening gene. The second gene editing fragment is connected to a C-terminus of the first gene editing fragment and includes a second homology arm, a Cas9 expression cassette and a sgRNA cassette. The Cas9 expression cassette successively includes a Cas9 promoter, a Cas9 gene and three nuclear localization sequences. The sgRNA cassette successively includes a sgRNA promoter, a first ribozyme, a targeting sequence, a scaffold and a second ribozyme. The first gene editing fragment and the second gene editing fragment are constructed as a linear fragment for gene editing of a chromosome of the *Candida viswanathii*.

8 Claims, 34 Drawing Sheets

Specification includes a Sequence Listing.

(56) References Cited

OTHER PUBLICATIONS

Deeva Uthayakumar et al., "CRISPR-Based Genetic Manipulation of Candida Species: Historical Perspectives and Current Approaches", Frontiers in Genome Editing, vol. 2, Article 606281, pp. 1-23 (Jan. 8, 2021).

* cited by examiner

| Table 2 ||
|---|---|
| Name | NO. |
| $P_{PGK1}$ | SEQ ID NO: 1 |
| *SpCas9* | SEQ ID NO: 2 |
| SV40 NLS | SEQ ID NO: 3 |
| $P_{TDH1}$ | SEQ ID NO: 4 |
| *Nrs$^R$* | SEQ ID NO: 5 |
| Frt | SEQ ID NO: 6 |
| HRL | SEQ ID NO: 7 |
| HRR | SEQ ID NO: 8 |
| N20::*Ade2* | SEQ ID NO: 9 |
| Ham | SEQ ID NO: 10 |
| HDV | SEQ ID NO: 11 |
| tRNA$^{Ala}$ | SEQ ID NO: 12 |
| tRNA$^{Gly}$ | SEQ ID NO: 13 |
| N20::*Ade2*-1 | SEQ ID NO: 14 |
| N20::*Ade2*-2 | SEQ ID NO: 15 |
| P1 | SEQ ID NO: 16 |
| P2 | SEQ ID NO: 17 |
| P3 | SEQ ID NO: 18 |
| P4 | SEQ ID NO: 19 |
| *Hyg$^R$* | SEQ ID NO: 20 |
| *Flp* | SEQ ID NO: 21 |
| *ARS2* | SEQ ID NO: 22 |
| *ColE1* | SEQ ID NO: 23 |
| *Ap$^R$* | SEQ ID NO: 24 |
| *CYP52A13* | SEQ ID NO: 25 |
| *CYP52A15* | SEQ ID NO: 26 |
| *CYP52A18* | SEQ ID NO: 27 |
| *CYP52A19* | SEQ ID NO: 28 |
| *CPRb* | SEQ ID NO: 29 |
| $P_{CYP52A15}$ | SEQ ID NO: 30 |
| $P_{CYP52A18}$ | SEQ ID NO: 31 |
| $P_{CYP52A19}$ | SEQ ID NO: 32 |
| $P_{CPRb}$ | SEQ ID NO: 33 |
| $P_{CYP52A13}$ | SEQ ID NO: 34 |

Fig. 14A

| Table 3 ||
|---|---|
| Name | NO. |
| *CYP52A13*-HRL | SEQ ID NO: 35 |
| *CYP52A13*-HRR | SEQ ID NO: 36 |
| *CYP52A15*-HRL | SEQ ID NO: 37 |
| *CYP52A15*-HRR | SEQ ID NO: 38 |
| *POX2*-HRL | SEQ ID NO: 39 |
| *POX2*-HRR | SEQ ID NO: 40 |
| N20::*CYP52A13/14* | SEQ ID NO: 41 |
| N20::*CYP52A15/16* | SEQ ID NO: 42 |
| N20::*POX2* | SEQ ID NO: 43 |
| *CYP52A18-CPRb* | SEQ ID NO: 44 |
| *CYP52A19-CPRb* | SEQ ID NO: 45 |
| *FAO2* | SEQ ID NO: 46 |
| $P_{POX4}$ | SEQ ID NO: 47 |
| $P_{CYP52A17}$ | SEQ ID NO: 48 |
| $P_{FAO2}$ | SEQ ID NO: 49 |
| *G6DP* | SEQ ID NO: 50 |
| *6-PGDH* | SEQ ID NO: 51 |
| *POS5* | SEQ ID NO: 52 |
| *GDP1* | SEQ ID NO: 53 |
| *PNTA* | SEQ ID NO: 54 |
| *PNTB* | SEQ ID NO: 55 |

SEQUENCE LISTING

```
Sequence total quantity: 55
SEQ ID NO: 1           moltype = DNA   length = 967
FEATURE                Location/Qualifiers
source                 1..967
                       mol_type = other DNA
                       organism = synthetic construct
SEQUENCE: 1
gactaaaagg tatgtgttgg tgtgaagaag aaagtggaag ggaagctggt gatggtgggt  60
tcgtctatcc cttttttata gttgcttgtt agtagggtac tctctaggga ctcgatgggg 120
gaaggttctt gatatttgct tagttcgaga aggttccaga tgagcgagac attttggta  180
gcgacattgg gcttgatcga tgatgatctg cacgacattt tgtgttcttg cgacacgctg 240
cactaccaag tgtaatctgg ctgaacggat cacaagataa acctctgaaa aattatctca 300
gggcatgcaa caacaattat acatagaaga gggagtcacg atatacacct gtgaaggaat 360
catgtggtcg gctctccttg aactttgaat tcatgcaatt attaagaaga agcacaggtg 420
agcaacccac catacgttca tttgcaccac ctgatgatta aaagccaaag aaagaaaaaa 480
aaaaagaaac aggcggtggg aattgttaca acccacgcga acccgaaaat ggagcaatct 540
tccccggggc ctccaaatac caactcaccc gagagagaga aagagacacc acccaccacg 600
agacggagta tatccaccaa ggtaagtaac tcagggttaa tgatacaggt gtacacagct 660
ccttccctag ccattgagtg ggtatcacat gacactggta ggttacaacc acgtttagta 720
gttattttgt gcattccatg gggatcagga agtttggttt ggtgggtgcg tctactgatt 780
cccctttgtc tctgaaaatc ttttccctag tggaacactt tggctgaatg atataaattc 840
accttgattc ccaccctccc ttctttctct ctctctctgt tacacccaat tgaattttct 900
tttttttttt tactttccct ccttctttat catcaagata agtaagttta tcaattgcct 960
attcaga                                                            967

SEQ ID NO: 2           moltype = DNA   length = 4104
FEATURE                Location/Qualifiers
source                 1..4104
                       mol_type = other DNA
                       organism = synthetic construct
SEQUENCE: 2
atggataaaa agtatagtat tggtttagat attggtacta actctgtggg ttggcagtt   60
atcactgacg aatataaagt tccatcaaag aaatttaagg tgttaggtaa cactgacaga 120
cactcaataa aaaagaatct tatcggtgct cttttgttcg actccggtga aactgccgag 180
gctacacgtt taaaaagaac agcaagaaga agatataccc gtagaaaaaa tagaatatgt 240
tatttacaag aaatctttte taatgaaatg gctaaagttg atgattcctt tttccataga 300
ttggaagagt catttttggt tgaagaagac aaaaagcatg agagacatcc aatctttggg 360
aatatagttg atgaagtggc ttaccatgaa aaatatccta ccatttatca tttaagaaag 420
aaaattggta gattcaactg aaaagctgac cttagattaa tctatttagc acttgcccat 480
atgattaaat ttagaggtca ttttttgatt gaaggtgatt tgaacccgaa taattctgac 540
gtggataaat tatttattca attagtccaa acctacaacc aattatttga ggaaaatcca 600
attaatgcta gtggtgtcga tgccaaagct atattatcag ccagattatc aaaatctaga 660
cgtttggaaa atttgattgc ccaattgcca ggagaaaaaa agaatggatt atttggaaac 720
ttgatcgcat tatcattggg tttgacacca aattttaaat ctaattttga tttagctgaa 780
gatgctaaat tacaattatc aaaagacacc tatgacgacg atttggacaa tttacttgct 840
caaattggtg atcaatatgc agatttgttc ttagctgcta aaaacttatc tgatgctatt 900
ttgttgtctg atatttttga gagtgaacac agaaataacc aagctccatt atcagcatct 960
atgatcaaac gttatgatga acaccatcag gatttgactt tattgaaagc tttggtgaga 1020
caacaattgc cagagaagta taaagaaatc tttttcgatc aatctaaaaa cgggtatgca 1080
ggttatattg atggggggtgc ctcccaagag gaattttaca aatttataaa acctatttta 1140
gaaaagatgg atgggactga ggaacttttg gtcaaattga acagagaaga tttgttacgt 1200
aaacagagaa cttttgataa tggtagtata ccctcaccaa ttcatttggg tgagttgcat 1260
gcaattttaa gaagacaaga agatttttat ccatttttaa aagataatag agaaaaaatc 1320
gagaaaattt aacctttag aattccatac tatgttgggc ctttggctag aggtaattca 1380
agatttgcct ggatgacacg taaatcagaa gaaactatta cccctggaa ttttgaagag 1440
gttgttgata aaggagcatc agcacagagt tttattgaaa gaatgaccaa tttcgataaa 1500
aacttaccaa atgaaaaagt tttaccaaaa cattccttgt atacgaata ttttactgtt 1560
tacaatgaac ttacaaaggt taaatatgtt actgaaggta tgcgtaagcc agccttttta 1620
tctggagaac agaaaaggc aatagttgat ttattgttta aaacaaatag aaaagttact 1680
gttaaacaat taaagaaga ttactttaag aaaattgaat gttttgattc agttgaaatc 1740
agtggtgttg aagacagatt taatgctagt taggaactt accatgattt acttaaaatt 1800
atcaaagata aagatttctt ggataacgaa gaaatgaact acttagaga agacattgtt 1860
ttaaccttaa cttattcga agatagagag atgattgaag aacgtttgaa gacttatgca 1920
catttgtttg acgataaagt gatgaaacag ttgaaagaa gacgttatac tggatggggt 1980
agattgctc gtaaattgat caatgggatt agagataaag aaactatcttg 2040
gactttttga aatctgacgg atttgctaat gaaaatttca tgcaattgat ccacgacgat 2100
agtttgacat ttaaagaaga catccaaaag gcccaagtga gtgggcaagg tgattcatta 2160
catgaacata ttgcaaattt agccggatct cctgctatta gaaagggat attacaaact 2220
gttaaagttg tggatgaatt agtgaaagta atgggaagac ataaacctga aaacattgtg 2280
attgagatgg caagagaaaa tcaaactaca caaaagagac agaaaaatag tagaaacgt 2340
atgaaaagaa tagaagaggg tattaaagaa ttgggtagtc aaatattgaa agaacaccca 2400
gtggaaaata cccagttgca aaatgaaaaa ttatatctt actacttca aaatggacgt 2460
gatatgtatg ttgatcagga attagatata aatagacttt cagatatga tgtagatcat 2520
atagttccac aatcttttct gaaagatgat tccatagaca ataaagtatt aactagaagt 2580
gataaaaata gaggtaaaag tgataatgtc ccaagtgagg aagtcgtcaa aaagatgaaa 2640
aattactggc gtcaactttt gaatgctaaa ttaattactc aaagaaaatt tgataatttg 2700
actaaagcag aaagaggtgg gctttctgaa ttagataaag ccgggttcat taaaagacaa 2760
ttggtcgaaa ctagacaaat tactaaacat gttgcccaaa ttttagattc ccgtatgaac 2820
```

```
actaagtatg acgaaaatga taagttaata cgtgaggtta aagtcattac tttaaaatca 2880
aaacttgtct ctgatttcag aaaggatttc caattctata aagttagaga aattaataat 2940
tatcatcatg ctcatgatgc atatttgaat gctgtagttg gaactgcttt aatcaagaaa 3000
taccctaaat tagaatctga atttgtatat ggtgattaca aagtctatga tgttagaaag 3060
atgattgcta aatcagaaca agaaattggt aaagctacag ctaaatactt cttttactct 3120
aacattatga atttctttaa aacagaaatt actttggcaa acggtgaaat tagaaaagga 3180
cctcttattg aaacaaatgg tgagactgga gagatagttt gggacaaagg gcgtgatttc 3240
gctactgtta gaaaagtttt atcaatgcca caagttaaca ttgtaaagaa aacagaggtt 3300
caaactggtg gtttctcaaa agaaagtatt ttgcctaaaa gaaatagtga taaattgatt 3360
gccagaaaaa aggattggga tccaaagaaa tatggtggtt tcgactcacc aaccgtagcc 3420
tattctgttt tggttgtggc aaaggttgaa aagggtaaaa gtaaaaagct taaatcagta 3480
aaagaacttt tgggtattac aataatgaaa agaagttcct ttgaaaagaa ccctattgat 3540
ttttttggaag ctaaaggtta taaggaagta aagaaggact taataatcaa attgcctaaa 3600
tattctttat ttgaattaga aaatgggaaa aaaagaattc tggctctgc tggagaattg 3660
caaaagggta atgaattagc attgccttcc aaatatgtta acttcttgta tttagcttca 3720
cactatgaaa agttgaaagg gtcaccagaa gataacgagc aaaaacaatt atttgttgaa 3780
caacacaaac actacttaga tgagattata gaacaaatta gtgaattcag taaaagagtg 3840
atattagctg atgcaaattt agataaagtt ttgtcagcct ataacaaaca tagaagataag 3900
ccaattagag aacaagcaga aaacattatt cacttattta cccttaccaa tttaggagca 3960
cctgctgctt tcaagtattt tgatacaaca attgatcgta aaagatatac ctcaacaaaa 4020
gaagtcttag acgccacctt aattcatcaa tcaatcactg gattgtatga gacaagaatt 4080
gatttgtctc aattgggtgg tgat 4104

SEQ ID NO: 3        moltype = DNA   length = 69
FEATURE             Location/Qualifiers
source              1..69
                    mol_type = other DNA
                    organism = synthetic construct
misc_feature        1..69
                    note = This sequence was repeated three times for the same
                    SV40 NLS sequence
SEQUENCE: 3
cctaagaaga aaagaaaagt tgatccaaag aaaaagcgta aggtggatcc taagaaaaag 60
agaaaggtt                                                         69

SEQ ID NO: 4        moltype = DNA   length = 1455
FEATURE             Location/Qualifiers
source              1..1455
                    mol_type = other DNA
                    organism = synthetic construct
SEQUENCE: 4
aacgtggtat ggttgtaaga aacatattgc aactggagat agcgatcgtt caatttattc 60
cgattttgtg ggggaagtcg cccgctggtg ggcgtgcgcg aatgcaaaa gaaactcgac 120
catgcttttc atcatcccct aacagagcaa tcatattta aacgttcaag caaaagaaa 180
cgttggtttc ggctaatgat cacctgaaag gcaaaatcct tccatgtatg aacatgtagg 240
ttattccttt ttttttgcaac accctcgggc agttgttcat attcccggaa acaccacca 300
ctcggggcta agtggaagtt ctacaatccc ggggaaataa ggagcccgg tgagcacgcg 360
cacacaccac cttcacttca ttttgtccga gggaagcagc acgtgaagtc ggaacacgag 420
aggagcattt cttctatttt tctccttctct actgtgagtg catgattata tatgtaatca 480
aaagcgatca acttatggta gggtcgtgca cggcgcaccg ggttccaaaa tgatctgtga 540
gggacaaaat tcttttttttt ttccagcatg ccgctggtgg caaataccgt ggtggtatga 600
tgcaccctat gccattgatt cacaccacca ccattaatca acaattgaga gaggacaaaa 660
gtgaactatt ggtggtcgtc aggttatact cgtcagcttc ggaatattac gtcccttcag 720
tttgtgaaat gtcatcctgg cgatgttcga gagagatcag tccagagcg cgtggtagga 780
gaaacgggagc actgcagcaa caaaaaaaa atccaaaccc ggggggagg aagaagaaca 840
gccagggaaa ttgttcaccg acctgaccgt aaatttgctg ctgaaagaaa cgtgtcaaac 900
aagaccaatt ggctcaattg accctgaggg agtactttgt ctgccaccaa tgcttccacc 960
aaaacgctac ttttgtttttg caatcggatg gtgtgggtct ggggtccacc tgttttgtta 1020
agctacagaa ggtggcatat tcctctgatc aggtgctttt tttcggctgc tgctgctcgt 1080
ggtggtgtag tggtagtggt gtgtgtgcgt gtgcgtgagg gaggccgctt tttgctctct 1140
gactcctccc aatcagaagt tgctgtagca gtgaaacaac acaatggatg ataatgcccc 1200
gggcggtgcg tgtccgacac aaaaccactac attttttagc tgggagcata ctgccactac 1260
gacccaccca cccatggtca acaaaaaaat tctgacaaat tataaaataa cccttggatt 1320
cccccttgga aaaattttttg gtatttctct cttttcttttc cttttccttt ccctcttctt 1380
tttcccctcca tcaatcaatt gacgttcagt aactcaatta attcatcac atccctcaat 1440
taaagaattt aaaca                                                  1455

SEQ ID NO: 5        moltype = DNA   length = 522
FEATURE             Location/Qualifiers
source              1..522
                    mol_type = other DNA
                    organism = synthetic construct
SEQUENCE: 5
atgaaaattt cggtgatccc tgagcaggtg gcggaaacat tggatgctga gaaccatttc 60
attgttcgtg aagtgttcga tgtgcaccta tccgaccaag gctttgaact atctaccaga 120
agtgtgagcc cctaccggaa ggattacatc tcggatgatg actctgatga agactctgct 180
tgctatggcg cattcatcga ccaagagctt gtcgggaaga ttgaactcaa ctcaacatgg 240
aacgatctag cctctatcga acacattgtt gtgtcgcaca cgcaccgagg caaaggagtc 300
gcgcacagtc tcatcgaatt tgcgaaaaag tgggcactaa gcagacagct ccttggcata 360
```

```
cgattagaga cacaaacgaa caatgtacct gcctgcaatt tgtacgcaaa atgtggcttt    420
actctcggcg gcattgacct cttcacgtat aaaactagac ctcaagtctc gaacgaaaca    480
gcgatgtact ggtactggtt ctcgggagca caggatgacg cc                       522

SEQ ID NO: 6           moltype = DNA   length = 34
FEATURE                Location/Qualifiers
source                 1..34
                       mol_type = other DNA
                       organism = synthetic construct
SEQUENCE: 6
gaagttccta ttctctagaa agtataggaa cttc                                34

SEQ ID NO: 7           moltype = DNA   length = 1083
FEATURE                Location/Qualifiers
source                 1..1083
                       mol_type = genomic DNA
                       organism = Candida viswanathi
SEQUENCE: 7
cccacgatac acaaaagaat ttgagacaat gaatcaatga cgcagaacaa tttatttggc    60
cctctgtttt atatctttt gtgaaggcaa gttaaagcca acggtcgtgc tgtatgggcc    120
gctaagatag atattcccac tgcctgcatt gttctgcttt tctttctttt gctggagata    180
ggacctttga ggtcttgttg ttttgcggct ggaatgggtg gggcaaagac tgagccctgg    240
aagaaccatt gtaaccgcac tactattttg caaaacctcg tgccgtctga aaagcaataa    300
taacctaccc cttttgcaa tctttcattg tgcctacctt ggcgtttgtg tcaatgagca    360
ctatatggac tactccgctc aaccgtggac ggtaacatac cagcaccatc aactcatcga    420
cggtcatttc tcgtaacgaa tgcctaatgc cagtctatc catacaaggt tttatcactg    480
cgttgttttc ttgcccattt cagaaatggg tcaaaggtca tcgccactag ccacaaactc    540
aatatgctaa ttataaattt ccagatgggc actaaacacc acaatcctga agccattaac    600
tctacgttgc aactcgtctc ctcttttccc cctctagact ctagtctttg tccgattgag    660
cttttcttt agacaagttt agttatctaa aaagcacacc attattattt ttttagtatc    720
ctgcaagaag cgccggtttt gttgaagagt taaactctat gtgtgctgtg cttgtcggta    780
tgtgccgcaa ccatgtgtca cgtggactgc tcacgtggtt cgtctttcgc actgccagag    840
ttaattggtg gttattattt tggcagcact cattcggttt ttttttttctg actcctcccc    900
tttaagatgg gggaacaaaa aaaagaatc caagattctg aaaaatctta tcgggctac     960
atcgccatct catcacacag atatagagac atagatacac gatggacagc aaaactatag   1020
gtattttagg aggcggtcaa ttaggccgta tgattgttga agctgctcat agactcaaca    1080
tca                                                                  1083

SEQ ID NO: 8           moltype = DNA   length = 1001
FEATURE                Location/Qualifiers
source                 1..1001
                       mol_type = genomic DNA
                       organism = Candida viswanathi
SEQUENCE: 8
gcttccgttt acttgtacgg taagacaacc agaccagata gaaaaatggg acatatcaac    60
gtcactacgt cgtccatgga tgacgccgaa tcgagttgga agttcatctt gggcgagtct   120
gaagacatcc cggaatcctt aaccgctccc aaagaagaac cattggtggg tataataatg    180
ggttcggact ctgacttgcc agtgatggct gtcggtgcca gaatcttgaa gcagtttggt    240
gtcccatttg agctcacgat cgtcagcgcc cacagaaccc cacacagaat gtcagaatac    300
gccattgagg caccaaagag aggccttaaa tgtatcattg ccggtgctgg tggcgctgcc    360
catttgccag gtatggttgc cgccatgact ccattggcag tcattggtgt ccctgtgaa    420
ggatctactt tggacggtgt cgattcattg cactccatcg tgcagatgcc aagaggtatc    480
cccgtggcta cggtggctat caacaacagt accaatgctg cgcttttggc aattagaata    540
ttgggcgctt acgactccaa atggttgaca gaaatgaacc agtatatgtt gaacatggag    600
actgaagtgt tgggcaaggc tgaaacatta gaggaaatcg gctacgaaga ctacttgact    660
gataagttaa agaagtaggg tgtatatttc tatttgaagg atgatgcaat aataaaaaaa    720
aactaataaa tgataattga taaaaacgaa ttgaaacttg gtgtaataaa aaacctctat    780
tatacaaaaa cgctaaactt ccctgtccca gttacctcaa aatttaagtg cctttctctt    840
cttattctta agttgtcttt gtttatacgc ctgtgatctc gaatctctcc atccagaagt    900
gctcaccttc ttggtatctt taatttcgtc aacatccatg gtcttagtct catcctcatt    960
gtcttctttc ttctgctgtt tcttgagttc gtcctgcttc t                       1001

SEQ ID NO: 9           moltype = DNA   length = 76
FEATURE                Location/Qualifiers
source                 1..76
                       mol_type = other DNA
                       organism = synthetic construct
SEQUENCE: 9
gttttagagc tagaaatagc aagttaaaat aaggctagtc cgttatcaac ttgaaaaagt    60
ggcaccgagt cggtgc                                                    76

SEQ ID NO: 10          moltype = DNA   length = 43
FEATURE                Location/Qualifiers
source                 1..43
                       mol_type = other DNA
                       organism = synthetic construct
misc_feature           1..6
                       note = Complementary to the first 6 nucleotides of the
                       target sequence
```

-continued

```
SEQUENCE: 10
nnnnnnctga tgagtccgtg aggacgaaac gagtaagctc gtc                          43

SEQ ID NO: 11           moltype = DNA   length = 68
FEATURE                 Location/Qualifiers
source                  1..68
                        mol_type = other DNA
                        organism = synthetic construct
SEQUENCE: 11
ggccggcatg gtcccagcct cctcgctggc gccggctggg caacatgctt cggcatggcg        60
aatgggac                                                                 68

SEQ ID NO: 12           moltype = DNA   length = 79
FEATURE                 Location/Qualifiers
source                  1..79
                        mol_type = other DNA
                        organism = Candida parapsilosis
SEQUENCE: 12
taaaatgggc gtgtggcgta gttggtagcg cgttccctta gcatgggaaa ggtcatgagt        60
tcgattctta tctcgtcca                                                     79

SEQ ID NO: 13           moltype = DNA   length = 100
FEATURE                 Location/Qualifiers
source                  1..100
                        mol_type = other DNA
                        organism = Saccharomyces cerevisiae
SEQUENCE: 13
tttatttttt gtcactattg ttatgtaaaa tgccacctct gacagtatgg aacgcaaact        60
tctgtctagt ggataacaga attttttctat ggccaattta                            100

SEQ ID NO: 14           moltype = DNA   length = 20
FEATURE                 Location/Qualifiers
source                  1..20
                        mol_type = other DNA
                        organism = synthetic construct
SEQUENCE: 14
tcatagactc aacatcaaga                                                    20

SEQ ID NO: 15           moltype = DNA   length = 20
FEATURE                 Location/Qualifiers
source                  1..20
                        mol_type = other DNA
                        organism = synthetic construct
SEQUENCE: 15
tacaagtaaa cggaagcgtg                                                    20

SEQ ID NO: 16           moltype = DNA   length = 20
FEATURE                 Location/Qualifiers
source                  1..20
                        mol_type = other DNA
                        organism = synthetic construct
SEQUENCE: 16
gtgtaactag ggagagtgcc                                                    20

SEQ ID NO: 17           moltype = DNA   length = 19
FEATURE                 Location/Qualifiers
source                  1..19
                        mol_type = other DNA
                        organism = synthetic construct
SEQUENCE: 17
gagggcaact tcaccagat                                                     19

SEQ ID NO: 18           moltype = DNA   length = 20
FEATURE                 Location/Qualifiers
source                  1..20
                        mol_type = other DNA
                        organism = synthetic construct
SEQUENCE: 18
gggcgcctaa gaatatacgt                                                    20

SEQ ID NO: 19           moltype = DNA   length = 19
FEATURE                 Location/Qualifiers
source                  1..19
                        mol_type = other DNA
                        organism = synthetic construct
SEQUENCE: 19
aggcaaagtc cgtgaagag                                                     19

SEQ ID NO: 20           moltype = DNA   length = 1143
```

| FEATURE | Location/Qualifiers |
|---|---|
| source | 1..1143<br>mol_type = other DNA<br>organism = synthetic construct |

SEQUENCE: 20

```
atgaaaaagc ctgaactcac cgcgacgtct gtcgagaagt ttttgatcga aaagttcgac   60
agcgtctccg acttgatgca gctctcggag ggcgaagaat ctcgtgcttt cagcttcgat  120
gtaggagggc gtggatatgt cttgcgggta aatagctgcg ccgatggttt ctacaaagat  180
cgttatgttt atcggcactt tgcatcggcc gcgctcccga ttccggaagt gcttgacatt  240
ggggaattca gcgagagctt gacctattgc atctcccgcc gtgcacaggg tgtcacgttg  300
caagacttgc ctgaaaccga attgcccgct gtttttgcagc cggtcgcgga ggccatggat  360
gcgatcgctg cggccgatct tagccagacg agcgggttcg cccattcgg accgcaagga  420
atcggtcaat acactcatg gcgtgattc atatgcgcga ttgctgatcc ccatgtgtat  480
cactggcaaa ctgtgatgga ctacaccgtc agtgcgtccg tcgcgcaggc tctcgatgag  540
ttgatgcttt gggccgagga ctgccccgaa gtcggcacc tcgtgcacgc ggatttcggc  600
tccaacaatg tcttgacgga caatggccgc ataacagcgg tcattgactg gagcgaggcg  660
atgttcgggg attcccaata cgaggtcgcc aacatcttct tctggaggcc gtggttggct  720
tgtatggagc agcagacgcg ctacttcgag cggaggcatc cggagcttgc aggatcgccg  780
cggctccggg cgtatatgct ccgcattggt cttgaccaac tctatcagag cttggttgac  840
ggcaatttcg atgatgcagc ttgggcgcag ggtcgatgcg acgcaatcgt ccgatccgga  900
gccgggactg tcgggcgtac acaaatcgcc cgcagaagcg cggccgtctg accgatggc  960
tgtgtagaag tactccgcga tagtggaaac cgacgcgtcc gcactcgtcc ggaggcaaag  1020
gaattcggga gatggggag gctaactgaa acacggaagg agacaatacc ggaaggaacc  1080
cgcgctatga cggcaataaa aagacagaat aaaacgcacg ggtgttgggt cgtttgttca  1140
taa                                                                1143
```

| SEQ ID NO: 21 | moltype = DNA length = 1272 |
|---|---|
| FEATURE | Location/Qualifiers |
| source | 1..1272<br>mol_type = other DNA<br>organism = synthetic construct |

SEQUENCE: 21

```
atgccacaat ttgatatatt atgtaaaaca ccacctaagg tgcttgttcg tcagtttgtg   60
gaaaggtttg aaagaccttc aggtgagaaa atagcattat gtgctgctga actaacctat  120
ttatgttgga tgattacaca taacgaaca gcaatcaaga gagccacatt catgagctat  180
aatactatca taagcaattc gttgagtttc gatattgtca ataaatcact ccagtttaaa  240
tacaagacgc aaaaagcaac aattttggaa gcctcattaa agaaattgat tcctgcttgg  300
gaatttacaa ttattcctta ctatggacaa aaacatcaat ctgatatcac tgatattgta  360
agtagtttgc aattacagtt cgaatcatcg gaagaagcag ataagggaaa tagccacagt  420
aaaaaaatgc ttaaagcact tctaagtgag ggtgaaagca tctgggagat cactgagaaa  480
atactaaatt cgtttgagta tacttcgaga tttacaaaaa caaaaacttt ataccaattc  540
ctcttcctag ctactttcat caattgtgga agattcagcg atattaagaa cgttgatccg  600
aaatcattta aattagtcca aaataagtat ttgggagtaa taatccagtg tttagtgaca  660
gagacaaaga caagcgttag taggcacata tacttcttta gcgcaagggg taggatcgat  720
ccacttgtat atttggatga attttgagg aattctgaac cagtcctaaa acgagtaaat  780
aggaccggca attcttcaag caataaacag gaataccaat tattaaaaga taacttagtc  840
agatcgtaca ataaagcttt gaagaaaaat gcgccttatt caatcttgc tataaaaaat  900
ggcccaaaat ctcacattgg aagacatttg atgacctcat ttctttcaat gaagggccta  960
acggagttga ctaatgttgt gggaaattgg agcgataagc gtgcttctgc cgtggccagg  1020
acaacgtata ctcatcagat aacagcaata cctgatcact acttcgcact agtttctcgg  1080
tactatgcat atgatccaat tcaaaggaa atatagcat tgaaggatga gactaatcca  1140
attgaggagt ggcagcatat agaacagcta aagggtagtg ctgaaggaag catacgatac  1200
cccgcatgga atgggataat atcacaggag gtactagact accttcatc ctacataaat  1260
agacgcatat aa                                                     1272
```

| SEQ ID NO: 22 | moltype = DNA length = 695 |
|---|---|
| FEATURE | Location/Qualifiers |
| source | 1..695<br>mol_type = other DNA<br>organism = synthetic construct |

SEQUENCE: 22

```
aaaaatccgg ggtagcgatg aggtagtgca agttatacca gagagcctca atttgaacgt   60
ggtactgcac acaaaccgta gccctaaccc taattaaatg cacgtgaccc acacaatttt  120
caaccaccaa caacacacca aaaatgtatg tacactcgga gtggaaaata tttccccagg  180
cataattgtg gttgccaatt atagtggagt gtttgttatt agtataggag tactccttttt  240
atgtggaaaa atcgaaaaac ataaaacagt gcagctatac actaacaat ggtatacca  300
tggtcagaca cacccaaaca acacacccgt aatggttggt ttggctaaat agagcatctc  360
attttgtgta ttatttttatg ttttggatat ttttagcttg aaatttatat aaaaatattt  420
tactccaatt ttcttgccaa attttgtaca aaaagtaaaa aatagaactt ccaattttg  480
ttaaacaaac ttcaatctaa caaccggat agtgtttggg gggctgtgta acaccactgg  540
tgtaataaaa gtgccaatat ttggaaatta atttttggt ggtggacgtt tcttcctaaa  600
acacctagat gtgctagtat aattgcacaa ccagcacgca cactgcgtct ggccggtcct  660
ggactacatt ttgtctctaa cattcgtagc tgcag                             695
```

| SEQ ID NO: 23 | moltype = DNA length = 589 |
|---|---|
| FEATURE | Location/Qualifiers |
| source | 1..589<br>mol_type = other DNA<br>organism = synthetic construct |

```
SEQUENCE: 23
ttgagatcct ttttttctgc gcgtaatctg ctgcttgcaa acaaaaaaac caccgctacc    60
agcggtggtt tgtttgccgg atcaagagct accaactctt tttccgaagg taactggctt   120
cagcagagcg cagataccaa atactgttct tctagtgtag ccgtagttag gccaccactt   180
caagaactct gtagcaccgc ctacatacct cgctctgcta atcctgttac cagtggctgc   240
tgccagtggc gataagtcgt gtcttaccgg gttggactca agacgatagt taccggataa   300
ggcgcagcgg tcgggctgaa cggggggttc gtgcacacag cccagcttgg agcgaacgac   360
ctacaccgaa ctgagatacc tacagcgtga gctatgagaa agcgccacgc ttcccgaagg   420
gagaaaggcg gacaggtatc cggtaagcgg cagggtcgga acaggagagc gcacgaggga   480
gcttccaggg ggaaacgcct ggtatcttta tagtcctgtc gggtttcgcc acctctgact   540
tgagcgtcga tttttgtgat gctcgtcagg ggggcggagc ctatggaaa                589

SEQ ID NO: 24           moltype = DNA   length = 861
FEATURE                 Location/Qualifiers
source                  1..861
                        mol_type = other DNA
                        organism = synthetic construct
SEQUENCE: 24
atgagtattc aacatttccg tgtcgccctt attcccttttt tgcggcatt ttgccttcct    60
gttttttgctc acccagaaac gctggtgaaa gtaaaagatg ctgaagatca gttgggtgca   120
cgagtgggtt acatcgaact ggatctcaac agcggtaaga tccttgagag ttttcgcccc   180
gaagaacgtt ttccaatgat gagcactttt aaagttctgc tatgtggcgc ggtattatcc   240
cgtattgacg ccgggcaaga gcaactcggt cgccgcatac actattctca gaatgacttg   300
gttgagtact caccagtcac agaaaagcat cttacggatg gcatgacagt aagagaatta   360
tgcagtgctg ccataaccat gagtgataac actgcggcca acttacttct gacaacgatc   420
ggaggaccga aggagctaac cgcttttttg cacaacatgg gggatcatgt aactcgcctt   480
gatcgttggg aaccggagct gaatgaagcc ataccaaacg acgagcgtga ccacgacgatg   540
cctgtagcaa tggcaacaac gttgcgcaaa ctattaactg gcgaactact tactctagct   600
tcccggcaac aattaataga ctggatggag gcggataaag ttgcaggacc acttctgcgc   660
tcggcccttc cggctggctg gtttattgct gataaatctg gagccggtga gcgtgggtct   720
cgcggtatca ttgcagcact ggggccagat ggtaagccct cccgtatcgt agttatctac   780
acgacgggga gtcaggcaac tatggatgaa cgaaatagac agatcgctga gataggtgcc   840
tcactgatta agcattggta a                                             861

SEQ ID NO: 25           moltype = DNA   length = 1569
FEATURE                 Location/Qualifiers
source                  1..1569
                        mol_type = genomic DNA
                        organism = Candida viswanathi
SEQUENCE: 25
atgactgtac acgatattat cgccacatac ttcaccaaat ggtacgtgat agtaccactc    60
gctttgattg cttatagagt cctcgactac ttctatggca gatacttgat gtacaagctt   120
ggtgctaaac catttttcca gaaacagaca gacggctgtt tcggattcaa agctccgctt   180
gaattgttga agaagaagag cgacggtacc ctcatagact tcacactcca gcgtatccac   240
gatctcgatc gtcccgatat cccaactttc acattcccgg tcttttccat caaccttgtc   300
aatacccttg agcggagaa catcaaggcc atccttgcca ctcagttcaa cgatttctcc   360
ttgggtacca gacactcgca cttttgctcct tgttgggatg atggtatctt tacgttggat   420
ggcgccggct ggaagcacag cagatcctatg ttgagaccac agtttgccag agaacagatt   480
tcccacgtca gttgttgga gccacacgtt caggtgttct tcaaacacgt cagaaaggca   540
cagggcaaga cttttgacat ccaggaattg ttttttcagat tgaccgtcga ctccgccacc   600
gagtttttgt ttggtaatc cgttgagtcc ttgagagatg aatctatcgg catgtccatc   660
aatgcgcttg actttgacgg caaggctggc tttgctgatg cttttaacta ttcgcagaat   720
tatttggctt cgagagcgt tatgcaacaa ttgtactggg tgttgaacgg aaaaagttt   780
aaggagtgca acgctaaagt gcacaagttt gctgactact acgtcaacaa ggcttttggac   840
ttgacgcctg aacaattgga aaagcaggat ggttatgtgt ttttgtacga ttggtcaag   900
caaaccagag acaagcaagt gttgagagac caattgttga acatcatggt tgctggtaga   960
gacaccaccg ccggtttgtt gtcgtttgtt tcctttgaat tggccagaaa cccgaaagtt  1020
accaacaagt tgagagaaga aattgaggac aagtttggac tcggtgagaa tgctagtgtt  1080
gaagacatttt cctttgagtc gttgaagtcc tgtgaatact tgaaggctgt tctcaacgaa  1140
accttgagat tgtacccatc cgtgccacac aatttcagag ttgccaccaa gaacactacc  1200
ctcccaagag tggtggtaa ggacgggttg tctcctgttt tggtgagaaa gggtcagacc  1260
gttatttacg tgtctacgc agcccacaga aacccagctg tttacggtaa ggacgctctt  1320
gagtttagac cagagagatg gtttgagcca gagacaaaga agcttggctg gcccttcctc  1380
ccattcaacg gtggtccaag aatctgtttg ggacagcagt ttgccttgac agaagcttca  1440
tatgtcactg tcaggttgct ccaggagttt gcacacttgt ctatggaccc agacaccgaa  1500
tatccaccta agaaaatgtc gcatttgacc atgtcgcttt tcgacggtgc caatattgag  1560
atgtattag                                                          1569

SEQ ID NO: 26           moltype = DNA   length = 1623
FEATURE                 Location/Qualifiers
source                  1..1623
                        mol_type = genomic DNA
                        organism = Candida viswanathi
SEQUENCE: 26
atgtcgtctt ctccatcgtt tgcccaagag gttctcgcta ccactagtcc ttacatcgag    60
tactttcttg acaactacac cagatggtac tacttcatac ctttggtgct tctttcgttg   120
aactttataa gttgctcca cacaaggtac ttggaacgca ggttccacgc caagccactc   180
ggtaactttg tcagggaccc tacgtttggt atcgctactc cgttgctttt gatctacttg   240
aagtcgaaag gtacggtcat gaagtttgct tgggggcctct ggaacaacaa gtacatcgtc   300
```

```
agagacccaa agtacaagac aactgggctc aggattgttg gcctcccatt gattgaaacc   360
atggacccag agaacatcaa ggctgttttg gctactcagt tcaatgattt ctctttggga   420
accagacacg atttcttgta ctccttgttg ggtgacggta ttttcacctt ggacggtgct   480
ggctggaaac atagtagaac tatgttgaga ccacagtttg ctagaaaca ggtttctcac   540
gtcagttgt tggagccaca cgttcaggtg ttcttcaagc acgttagaaa gcaccgcgtt   600
caaacgttcg acatccaaga attgttcttc aggttgaccg tcgactccgc caccgagttc   660
ttgtttggtg agtctgctga atccttgagg gacgaatcta ttggattgac cccaaccacc   720
aaggatttcg atggcagaag agatttcgct gacgctttca actattcgca gacttaccag   780
gcctacagat ttttgttgca acaaatgtac tggatcttga atggctcgga attcagaaag   840
tcgattgctc tcgtgcacaa gtttgctgac cactatgtgc aaaaggcttt ggagttgacc   900
gacgatgact gcagaaaaca agacggctat gtgttcttgt acgagttggc taagcaaacc   960
agagacccaa aggtcttgag agaccagtta ttgaacattt tggttgccgg tagagacacg  1020
accgccggtt tgttgtcatt tgttttctac gagttgtcaa gaaaccctga ggtgtttgct  1080
aagttgagag aggaggtgga aaacagattt ggactcggtg aagaagctcg tgttgaagag  1140
atctcgtttg agtccttgaa gtcttgtgag tacttgaagg ctgtcatcaa tgaaaccttg  1200
agattgtacc catcggttcc acacaacttt agagttgcta ccagaaacac taccctccca  1260
agaggtggtg gtgaagatgg atactcgcca attgtcgtca agaagggtca agttgtcatg  1320
tacactgtta ttgctaccca cagagaccca agtatctacg gtgccgacgc tgacgtcttc  1380
agaccagaaa gatgggtttga accagaaact agaaagttgg gctgggcata cgttccattc  1440
aatggtggtc aagaatctg tttgggtcaa cagtttgcct tgaccgaagc ttcatacgtc  1500
actgtcagat tgctccagga gtttgcacac ttgtctatgg acccagacac cgaatatcca  1560
ccaaaattgc agaacacctt gacctgtcg ctctttgatg tgctgatgt tagaatgtac  1620
taa                                                              1623

SEQ ID NO: 27           moltype = DNA   length = 1554
FEATURE                 Location/Qualifiers
source                  1..1554
                        mol_type = genomic DNA
                        organism = Candida viswanathi
SEQUENCE: 27
atgattgaac aaatcctaga atattggtat attgttgtgc ctgtgttgta catcatcaaa    60
caactcattg cctacagcaa gactcgcgtc ttgatgaaac agtgggtgc tgctccaatc   120
acaaccagt tgtacgacaa cgttttcggt atcgtcaacg gatggaaggc tctccagttc   180
aagaaagagg gcagagctca agagtacaac gatcacaagt tgacagctca caagaaccca   240
agcgtcggca cctatgtcag tattctttc ggcaccaaga ttgtcgtgac caaggatcca   300
gagaatatca aagctatttt ggcaacccag tttggcgatt tttcttggg caagagacac   360
gctcttttta aacctttgtt aggtgatggg atcttcacct tggacggcga aggctggaag   420
catagcagat ccatgttaag accacagttt gccagaaaca aagttgctca tgtgacgtcg   480
ttggaaccac acttccagtt gttgaagaag catatcctta aacacaaggg tgagtacttt   540
gatatccagg aattgttctt tagatttact gtcgactcgg ccacgagtt cttatttggt   600
gagtccgtgc actccttaaa ggacgaaact atcggtatca accaagacga tatagattt   660
gctggtagaa aggactttgc tgagtcgttc aacaaagccc aggagtattt gtctattaga   720
attttggtgc agaccttcta ctggttgatc aacaacaagg agtttagaa tctgtaccaag   780
ctggtgcaca agtttaccaa ctactatgtt cagaaagctt tggatgctac cccagaggaa   840
cttgaaaagc aaggcgggta tgtgttcttg tatgagcttg tcaagcagac gagagaccc    900
aaggtgttgc gtgaccagtc tttgaacatc ttgttggcag aagagacac cactgctggg    960
ttgttgtcct ttgctgtgtt tgagtggcc agaaacccac acatctgggc caagttgaga   1020
gaggaaattg aacagcagtt tggtcttgga aagactctc gtgttgaaga gattacctt   1080
gagagcttga agatgtgaga gtacttgaaa gcgttcctta acgaaacctt gcgtgtttac   1140
ccaagtgtcc caagaaactt cagaatcgcc accaagaata caacattgcc aagggtggt   1200
ggtccagacg gtacccagcc aatcctgatc caaaaggagg aaggtgtgtc gtatgtatca   1260
aactctaccc acttagatcc tgtctattat ggccctgatg ctgctgagtt cagaccagag   1320
agatggtttg agccatcaac cagaaagctc ggctgggctt acttgccatt caacggtggg   1380
ccacgaatct gtttgggtca gcagtttgcc ttgaccgaag ctggtacgt tttggtcaga   1440
ttggtgcaag agttctccca cattaggctg gacccagatg aagtgtatcc accaaagagg   1500
ttgaccaact tgaccatgtg tttgcaggat ggtgctattg tcaagtttga ctag         1554

SEQ ID NO: 28           moltype = DNA   length = 1539
FEATURE                 Location/Qualifiers
source                  1..1539
                        mol_type = genomic DNA
                        organism = Candida viswanathi
SEQUENCE: 28
atgctcgatc agatcttaca ttactgggtac attgtcttgc cattgttggc cattatcaac    60
cagatcgtgg ctcatgtcag gaccaattat ttgatgaaga aattgggtgc taagccattc   120
acacacgtcc aacgtgacgg gtggttgggc ttcaaattcg gccgtgaatt cctcaaagca   180
aaaagtgctg gagactggt tgatttaatc atctcccgtt ccacgataa tgaggacact   240
ttctccagct atgcttttgg caaccatgtg gtgttcacca gggacccga gaatatcaag   300
gcgcttttgg caacccagtt tggtgatttt tcattgggca gcagggtcaa gttcttcaaa   360
ccattattgg ggtacggtat cttcacattg gacgccgaag gctggaagca cagcagagcc   420
atgttgagac acagtttgc cagagaacaa gttgctcatg tgacgtcgtt ggaaccacac   480
ttccagttgt gaagaagca tatccttaaa acacaggggt gagtacttgga tatccaggaa   540
ttgttcttta gatttactgt cgactcggcc acggagtct tatttggtga gtccgtgcac   600
tccttaaagg acgaaaat tggtatcgac aaagaagcga tgtctgaaga aagacgcaga   660
tttgccgacg cgttcaacaa gtcgcaagtc tacgtggcca ccagagttgc tttacagaac   720
ttgtactggt tggtcaacaa caagagttc aaggagtgca atgacattgt ccacaagttt   780
accaactact atgttcagaa agccttggat gctaccccag ggaacttga aaagcaaggc   840
gggtatgtgt tcttgtatga gcttgtcaag cagacgagag acccaaggt gttgcgtgac   900
cagtcttga acatcttgtt ggcaggaaga gacaccactg ctgggttgtt gtcctttgct   960
```

```
gtgtttgagt tggccagaaa cccacacatc tgggccaagt tgagagagga aattgaacag   1020
cagtttggtc ttggagaaga ctctcgtgtt gaagagatta cctttgagag cttgaagaga   1080
tgtgagtact tgaaggccgt gttgaacgaa actttgagat tacacccaag tgtcccaaga   1140
aacgcaagat ttgcgattaa agacacgact ttaccaagag gcggtggccc caacggcaag   1200
gatcctatct tgatcaggaa ggatgaggtg gtgcagtact ccatctcggc aactcagaca   1260
aatcctgctt attatggcgc cgatgctgct gattttagac cggaaagatg gtttgaacca   1320
tcaactagaa acttgggatg ggctttcttg ccattcaacg gtggtccaag aatctgtttg   1380
ggacaacagt ttgctttgac tgaagccggt tacgttttgg ttagacttgt tcaggagttt   1440
ccaaacttgt cacaagaccc cgaaaccaag taccccaccac ctagattggc acacttgacg   1500
atgtgcttgt tgacggtgc acacgtcaag atgtcatag                            1539

SEQ ID NO: 29          moltype = DNA   length = 2040
FEATURE                Location/Qualifiers
source                 1..2040
                       mol_type = genomic DNA
                       organism = Candida viswanathi
SEQUENCE: 29
atggctttag acaagttaga tttgtatgtc atcataacat tggtggtcgc tgtggccgcc    60
tattttgcta agaaccagtt ccttgatcag ccccaggaca ccgggttcct caacacggac   120
agcggaagca actccagaga cgtcttgctg acattgaaga agaataataa aaacacgttg   180
ttgttgtttg ggtcccagac cggtacggca gaagattacg ccaacaaatt gtcaagagaa   240
ttgcactcca gatttggctt gaaaaccatg gttgcagatt tcgctgatta cgattgggat   300
aacttcggag atataccga agatatcttg gtgtttttca tcgttgccac ctacggtgag   360
ggtgaaccta ccgacaatgc cgacgagttc acacctggt tgactgaaga agctgacact   420
ttgagtactt tgagatatac cgtgttcggg ttgggtaact ccacctacga gttcttcaat   480
gctattggta gaaagtttga cagattgttg agtgagaaag atggtgacag atttgctgaa   540
tatgctgaag gtgacgacgg cactggcacc ttggacgaag atttcatggc ctggaaggat   600
aatgtctttg acgccttgaa gaatgacttg aactttgaag aaaaggaatt gaagtacgaa   660
ccaaacgtga aattgactga gagagatgac ttgtctgctg ccgactccca gtttccttgg   720
ggtgagccaa acaagaagta catcaactcc gagggcatcg acttgaccaa gggtccattc   780
gaccacaccc acccatactt ggccaggatc accgagacca gagagttgtt cagctccaag   840
gaaagacact gtattcacgt tgaatttgac atttctgaat cgaacttgaa atacaccacc   900
ggtgaccatc tagccatctg gccatccaac tccgacgaaa acatcaagca atttgccaag   960
tgtttcggat tggaagataa actcgacact gttattgaat tgaaggcatt ggactccatt   1020
tacaccattc cattcccaac tccaattact tacggtgctg tcattagaca ccatttagaa   1080
atctccggtc cagtctcgag acaattcttt ttgtcgattg ctgggtttgc tcctgatgaa   1140
gaaacaaaga agactttcac cagacttggt ggtgacaaac aagaattcgc caccaaggtt   1200
acccgcagaa agttcaacat tgccgatgcc ttgttatatt cctccaacaa cactccatgg   1260
tccgatgttc cttttgagtt ccttattgaa aacatccaac acttgactcc acgttactac   1320
tccatttctt cttcgtcgtt gagtgaaaaa caactcatca atgttactgc agtcgttgag   1380
gccgaagaag aagccgatgg cagaccagtc actggtgttg ttaccaactt gttgaagaac   1440
attgaaattg cgcaaaacaa gactggcgaa agcccacttg ttcactacga tttgagcggc   1500
ccaagaggca agttcaacaa gttcaagttg ccagtgcagg tgagaagatc caactttaag   1560
ttgccaaaga actccaccac cccagttatc ttgattggtc caggtactgg tgttgcccca   1620
ttgagaggtt tcgttagaga aagagttcaa caagtcaaga atggtgtcaa tgttggcaag   1680
actttgttgt tttatggttg cagaaactcc aacgaggact ttttgtacaa gcaagaatgg   1740
gccgagtacg cttctgtttt gggtgaaaac tttgagatgt tcaatgcctt ctctagacaa   1800
gacccatcca agaaggttta cgtccaggat aagatttttag aaaacagcca acttgtgcac   1860
gaattgttga ccgaaggtgc cattatctac gtctgtggtg acgccagtag aatgccagaa   1920
gacgtccaga ccacgatctc caagattgtt gccaaaagca gagaaatcag tgaagacaag   1980
gccgctgaat tggtcaagtc ctggaaagtc caaaatagat accaagaaga tgtttggtag   2040

SEQ ID NO: 30          moltype = DNA   length = 1018
FEATURE                Location/Qualifiers
source                 1..1018
                       mol_type = genomic DNA
                       organism = Candida viswanathi
SEQUENCE: 30
gttgcactct tgccataggc atgaaaatag gccgttatag tactatattt aataagcgta    60
ggagtatagg atgcatatga ccggttttc tatattttta agataatctc tagtaaattt   120
tgtattctca gtaggatttc atcaaatttc gcaaccaatt ctggcgaaaa aatgattctt   180
ttacgtcaaa agctgaatag tgcagtttaa agcacctaaa atcacatata cagcctctag   240
atacgacaga gaagctcttt atgatctgaa gaagcattag aatagctact atgagccact   300
attggtgtat atattaggga ttggtgcaat taagtacgta ctaataaaca gaagaaaata   360
cttaaccaat ttctggtgta tacttagtgg tgagggacct tttctgaaca ttcgggtcaa   420
actttttttt ggagtcgac atcgatttt cgtttgtgta ataatagtga acctttgtgt   480
aataaatctt catgcaagac ttgcataatt cgagcttggg agttcacgcc aatttgacct   540
cgttcatgtg ataaaagaaa agccaaaagg taattagcaa acgcaatggg aacatggagt   600
ggaaagcaat ggaagcacgc ccaggacgga gtaatttagt ccacactaca tctgggggtt   660
ttttttttgt gcgcaagtac acacctggac tttagtttt gccccataaa gttaacaatc   720
taacctttgg ctctccaact ctcctccgccc ccaaatattc gtttttacac cctcaagcta   780
gcgacagcac aacacccatt agaggaatgg ggcaaagtta aacactttg gcttcaatga   840
ttcctattcg ctactacatt cttctcttgt tttgtgcttt gaattgcacc atgtgaaata   900
aacgcaaatt atataaccct tttcatccct cctcctatat ctcttttttgc tacatttgt   960
tttttacgtt tcttgctttt gcactctccc actcccacaa agaaaaaaaa actacact    1018

SEQ ID NO: 31          moltype = DNA   length = 739
FEATURE                Location/Qualifiers
source                 1..739
```

```
                        mol_type = genomic DNA
                        organism = Candida viswanathi
SEQUENCE: 31
cccggacttg tttggggcag cagtacactt tgattgaagc gagctatttg ctagtcaggt    60
tggcgcagac ctaccgggta atcgatttgc tgccaggagtc ggcgtaccca ccaagaaaga   120
agtcgttgat caatatgagt gctgccgatg gggtggttgt aaagtttcac aaggatctag   180
atggatatgt aaggtgtgta ggaggagcgg agataaatta gatttgattt tgtgtaaggt   240
ttagcacgtc aagctactcc gcactttgtg tgtagggagc acatactccg tctgcgcctg   300
tgccaagaga cggcccaggg gtagtgtgtg gtggtgaaag tgcatgtgac acaataccct   360
ggttctggcc aattggggat ttagtgtagg taagctgaca cctgaaacac tcctcaacgc   420
ttgagacact ggtgggtaga gatgcgggcc aggaggctat tcttgtcgtg ctacccgtgc   480
acggaaaatc gattgaggga agaacaaatt tatccgtgaa atccacagag cggataaatt   540
tgtcacattg ctgcgttgcc cacccacagc attctctttt ctctctcttt gtcttactcc   600
gctcctgttt ccttatccag aaatacacac caactcatat aaagatacgc tagcccagct   660
gtctttcttt ttcttcactt ttttttggtgt gttgcttttt tggctgctac tttctacaac   720
caccaccacc accaccacc                                                 739

SEQ ID NO: 32          moltype = DNA   length = 558
FEATURE                Location/Qualifiers
source                 1..558
                       mol_type = genomic DNA
                       organism = Candida viswanathi
SEQUENCE: 32
tgccacagct gtctgatgc tggccgacac actttcaacg gtctggattt ggtctagaat    60
tcttgcacat gcacaacaag gaaactctta caatgacaac acttatgatc taattccagc   120
tgatcttgct aatccttatc aacgtagttg tgatcattgt ttgtctgaat tatacacacc   180
agtggaagaa tatggtctaa tttgcacgtc ccactggcat tgtgtgtttg tgggggggg    240
ggggggtgcac acatttttag tgccattctt tgttgattac ccctccccc tatcattcat    300
tcccacagga ttagttttttt cctcactgga attcgctgtc cacctgtcaa ccccccccc   360
ccccccccac tgcctaccc tgccctgccc tgcacgtcct gtgttttgtg ctgtgtcttt   420
cccacgctat aaaagccctg gcgtccggcc aaggttttc cacccagcca aaaaaacagt   480
ctaaaaaatt tggttgatcc ttttggttg caaggtttc caccaccact tccaccacct   540
caactattcg aacaaaag                                                 558

SEQ ID NO: 33          moltype = DNA   length = 754
FEATURE                Location/Qualifiers
source                 1..754
                       mol_type = genomic DNA
                       organism = Candida viswanathi
SEQUENCE: 33
tgggggggggg atcaactgat tagcggaaga ttggtgttgc ctgtgggtt ctttttatttt   60
tcatatgatt tctttgcgcg agtaacatgt gccaatctag tttatgatta gcgtaccctc   120
acaattggca tcttggacgg gcgtgttttg tcttacccca agccttattt agttccacag   180
tctcgacggt gtctgccga tgtcttctcc cacccctcgc aggaatcatt cgaagttgtt   240
gggggatctc ctccgcagtt tatgttcatg tcttccccac tttggttgtg attggggtag   300
cgtagtgagt tggtgatttt cttttttcgc aggtgtctcc gatatcgaag tttgatgaat   360
ataggagcca gatcagcatg gtatattgcc tttgtagata gagatgttga acaacaacta   420
gctgaattac acaccaccgc taaacgatgc gcacagggtg tcaccgccaa ctgacgttga   480
gtggagttgt tgttggcagg gccatattgc taaacgaaga gaagtagcac aaaacccaag   540
gttaagaaca attaaaaaaa ttcatacgac aattccacag ccatttacat aatcaacagc   600
gacaaatgag acagaaaaaa ctttcaacat ttcaaagttc cctttttcct attacttctt   660
tttttcttttc cttccttca tttccttttcc ttctgcttttt attactttac cagtctttgg   720
cttgttttg caattcctca tcctcctcct cacc                                754

SEQ ID NO: 34          moltype = DNA   length = 638
FEATURE                Location/Qualifiers
source                 1..638
                       mol_type = genomic DNA
                       organism = Candida viswanathi
SEQUENCE: 34
agatatttat tcattatta gtttgcctat ttatttctca ttaccccatca tcattcaaca    60
ctatatataa agttacttcg gatatcattg taatcgtgcg tgtcgcaatt ggatgatttg   120
gaactgcgct tgaaacggat tcatgcacga agcggagata aaagattacg taatttatct   180
cctgagacaa tttttagccgt gttcacacgc ccttcttttg tctgagcgaa ggataaataa   240
ttagacttcc acagctcatt ctaatttccg tcacgcgaat attgaagggg ggtacatgtg   300
gccgctgaat gtggggcag taaacgcagt ctctcctctc caggaatag tgcaacggag    360
gaaggataac ggatagaaag cggaatgcga ggaaaatttt gaacgcgcaa gaaaagcaat   420
atccgggcta ccaggttttg agccaggaa cacactccta tttctgctca atgactgaac   480
atagaaaaaa caccaagacg caatgaaacg cacatgaca tttagacctc cccacatgtc   540
atagtttgtc ttaacagaaa agtataataa gaacccatgc cgtccctttt ctttcgccgc   600
ttcaactttt ttttttttat cttacacaca tcacgacc                           638

SEQ ID NO: 35          moltype = DNA   length = 1003
FEATURE                Location/Qualifiers
source                 1..1003
                       mol_type = genomic DNA
                       organism = Candida viswanathi
SEQUENCE: 35
gtccaggtgt gcacctgcgc acaaaaaaaa aaaagaatac tagatgtgtt gtgggctaaa    60
```

```
tggcactgtc atgggcgtgt ttccattgct ttctactccg tgttcccctt ggggggtctg    120
ccaattacct tttggctctt cttttatcac atgaatgagg ataaattgag ttgatatggt    180
gcaacgttat gtggaaacct tcaactgtgc ccttgcattg tagaaaccaa caccatcacc    240
accccgtgta acacacttca ctgcaatgaa agttaacgga aaaataaaa aaagtcaca     300
atagtcaata attctggcgc cccccattgt tttgttggtt cggagtgctg cggagttttt    360
ttatttttc tgttggagtt tctcatcttt tgcattgttt gcaaatgtt tgaaattctg     420
gctgccattt attttttatt acccctctaa ataatatgga ttacgtaatc gactgtcgat    480
catttgtcgt gcaaacaggt tgcaaaaacc acaatcacat gcttgcataa cgtctaggct    540
ttacagatta cataatcaga gtagcagtca aacaatcaca tggagatcga ccttctatct    600
aagacatcgt ccggagttac aaaacaaaac tccttttgac tcaacaggat ggaaggaaac    660
aacaacctgg aacgtcccca tgtgaatgca acacacacac acacgcac ccctatcaa     720
taaataacaa tccgtgaatt aacctaatca atagctacaa acagactaaa ccaatcaaaa    780
ataacacatg atcctctaat acatctcaat gttggcaccg tcgaaaaggg acatggtcaa    840
atgcgacatt ttcctaggtg gatattcggt gttggggtcc atagacaagt gtccaaactc    900
ttggagcaat ctgacagtga catacgaagc ttctgtcaag gcaaactgct gtcccaagca    960
aattcttgga ccaccgttga atggaaggaa ggcccagcca agc                     1003

SEQ ID NO: 36          moltype = DNA   length = 1048
FEATURE                Location/Qualifiers
source                 1..1048
                       mol_type = genomic DNA
                       organism = Candida viswanathi
SEQUENCE: 36
tgttctccgg ctcaagggtg ctgataaggt tgatggaaaa gattgggaat gtaaaagttg     60
ggatatctgg acgattgagc gcttggatac gctcgagagt gaagtctatg agggtaccgt    120
cactcttctt ttttaacaat tcaagtggag cttttgaatcc gaaataaccg tctgtttgtt    180
tctggaaaaa cggtttagca ccaagcttgt acatcaagta tctgccgtaa agtagtcga    240
ggacccctata agcaatcaaa gcgagtggta ctatcacgta ccatttggtg atgtatgtgg    300
cgataatatc ctgtgcagtc atggtcgtga ggtgtgtgtg tgttgataga caagaaaaa     360
gaaaaagttg aaacggccca ggaagaggga aggcatgggt ccttattata ctttttttgc    420
tttcgccaga gaagctttca catgtgggga ggtctaaatg tccatgtgcg attcattgtg    480
tcttggtgga gttttttttt tttgtctacg ttaagttttt gtgcagaaga ggagtgtgtc    540
ccctggctca aaacctgata gcccggatat tgctttcctt gcgcattcaa attttcctc    600
gcattccact tgctatccgt tatccttccc ccgttgtact attcctgggg ggggggggg    660
gggagagaga gactgcgtt actggcaccc cacattcatc ggctacgtct acccccccct    720
tccttattgt tgcagttttc gcgtgacgga tattttaatg aacttgtgaa gtctaattat    780
ttatccttag ctcagaagaa gggcgtgtga atgaggccaa aattgtctta ggagataatc    840
tcgtgttatc tccgcatcgt gcatgaatcc gttccaacta cagtttcaaa ttacccaatt    900
gcaacacgca cgattacaat gatatatgag ttccgaaata actttatata tattgttgaa    960
tgatgatggg tgatgagaaa taaataggca aactaaatag tgaataaata tctttaagct   1020
tctgaccctg cagctctaac ttcagcgg                                      1048

SEQ ID NO: 37          moltype = DNA   length = 971
FEATURE                Location/Qualifiers
source                 1..971
                       mol_type = genomic DNA
                       organism = Candida viswanathi
SEQUENCE: 37
caaacaacgc gttgttgtcg gtgactatca catccaatcg ctgcttcgaa ataaagtacc     60
caagtatgtt caagatgtag tttgctctca aatagtaaga caatctggca ctgtcggcaa    120
ttgatgtgcc cttcttgtag gatatgtcgc cggcgtagta taacaactcg gccgcgttca    180
attggtccaa gtcaaactcg ttcgacaata atgtggtaac ttctaggaac gcttggttca    240
actccacttc gtctccattg ggcaaggcca caggcttgga tccatcgcct agtttctggc    300
gcgattcttc cagtggtgtt ggggttgtca aaatgtggac aaggtcattc ttgatgccgc    360
tgaaatctat ggtgtctaaa tcaatgtctt cctcaaactt aagggtgttg tagatatccg    420
cgaatgcctc cagtgaccag ttgaaagcgc cgctcatttg gttataatgg ttcacgttgg    480
gtaagtttgg gcaatgttgt ttacaaaaaa ttttctttt cgttttcaaa cagtgctgat    540
gagcgagcaa cgaaggtagg ggaagaaaaa aaaaaaaaa gtttgaacgg ttttggtcaa    600
aacccactac agttattagt accagaaaaa tcaatcgccg attcaattta aatacacaaa    660
ctataaataa cactagcaag gataagcaac cttagaacat tctaacgtca gccaatcaca    720
agagtgacaa ggtcaaggtg ttctgcaatt ttggtgggta ctcagcgttt ggatccagga    780
caagtttcca aactcttgga gcaatctgac agtgacgtat gaagcttcag tcaaggcaaa    840
ctgctgaccc aaacagattc ttggaccacc attgaatgga acatatgccc agcccaactt    900
tctagttttct ggctcgaacc atctttctgg tctgaagacg tcggcgtcgg caccgtagat    960
acttgggtct c                                                        971

SEQ ID NO: 38          moltype = DNA   length = 1039
FEATURE                Location/Qualifiers
source                 1..1039
                       mol_type = genomic DNA
                       organism = Candida viswanathi
SEQUENCE: 38
cgtaggatcc aacacgacgt taccgagcgg cttggcgtgg aacctgcgtt ccaagtactt     60
tgtgtggagc aagctgtga agttcaacga aagaagcacc aaagggatga agtagtacca    120
tctggtgtag ttgtcaagaa agtactcgat gtaaggacta gtggtagcga gaacctcctg    180
agcaaacgat ggagaagacg acatagtgta ggttttttta ttttcttct ttgtgtgttg    240
ctgcactgat tgtgggagtg ggagagagtg caaaagcaaa aagcaaaaag caaaatggca    300
gcaaaaagag acattggagg acagacgaaa aggtatatat aattgtcgtt tatttcacat    360
ggtgcaaatc aaaacacaaa acaagagagt agcaaatagg aatcattgaa accaaaagtg    420
```

```
tttaactttg cccattcccc tcatgggtgt tgtgttgtcg ttagctcgag ggtgtaaaac   480
gagcatctgg aggcgagac  actgggagag ccaaaggtga gattgttaac tttatggggc   540
aataactaaa gtccaggtgt gcacctgcgc acaaaaaaaa aaaagaatac tagatgtgtt   600
gtgggctaaa tggcactgtc atgggcgtgt ttccattgct ttctactccg tgttcccctt   660
ggggggtctg ccaattacct tttggctctt cttttatcac atgaatgagg ataaattgag   720
ttgatatggt gcaacgttat gtggaaacct tcaactgtgc ccttgcattg tagaaaccaa   780
caccatcacc accccgtgta acacacttca ctgcaatgaa agttaacgga aaaaataaaa   840
aaaagtcaca atagtcaata attctggcgc cccccattgt tttgttggtt cggagtgctg   900
cggagttttt ttattttttc tgttggagtt tctcatcttt tgcattgttt gcaaaatgtt   960
tgaaattctg gctgccattt atttttttatt accccctcaa ataatatgga ttacgtaatc  1020
gactgtcgat catttgtcg                                                1039
```

SEQ ID NO: 39  moltype = DNA  length = 960
FEATURE    Location/Qualifiers
source     1..960
       mol_type = genomic DNA
       organism = Candida viswanathi
SEQUENCE: 39

```
tgaatccaca atccccacct ccaccgcggt ggaaaaacct ggaaaaaaca aaccaccatc    60
aacaaccacc cacctccact ccactcccca aacaacaacc acacacacac ctcatggcac   120
gtcaaggact aatcagcatc ctctccctcg tgtacttcat ctacggtctc acgaaatgcg   180
tcacgcagcc gctcccacca cacctcatcc aaggcgggca cttccaattc ctcaccaacg   240
ttctgcttgt cctcaccatt ctctacgtgc tccagacgat cgtcacgccg acgagccggc   300
acctccggac gcaacacaac gtcgtcgcga gtttggagtt caccgtcacg gtgacctact   360
ggacgttgtt cttgttggtg ccgtcgtggc taaaccccgc ggacgagtgg ggccgcgact   420
gggtgcttga cgtcgcgatc cacctctggc cgttcgtcta cttggtcgtg ttcgacaacc   480
aggacagaat cccccgaag agggcctggg gtttgactgg ggccgtgatt gttgtgtact   540
ggtgctacct tgaaagagtc gttctgtgat atgccgggga tggggtcacg aggttttgcgt   600
acccttttt gaatgatagg acgttgacgc agcggtttgg gtggatggtg ttgatttggg   660
ttgtgagttg tttgaactat tacgttattg gattgagaaa tatgctatag atatgtggat   720
gataaatact tgtttattca cagaaataat ataaacttta actagagaca aaattccatg   780
gggaggctct acttggataa gatggcagcg gctgctttag ctctctcgga tctttctctg   840
ttctcgagtc cagaacggtt caacatggct tccaaggctt cagagtatgg tgccttgtag   900
ttgaatgggt cgttgacgtc cttgacggat tccaagtagt tggtgtagat gttacgtcg    960
```

SEQ ID NO: 40  moltype = DNA  length = 940
FEATURE    Location/Qualifiers
source     1..940
       mol_type = genomic DNA
       organism = Candida viswanathi
SEQUENCE: 40

```
cgtcggtctt ttcgtcaaaa gtagcagtgg tttcacaacc agcaacgttg gaaccgtgac    60
ccaattcggt cataccgaaa caaccataaa gctgcttgac aataccggct tccttcttgt   120
tggaccaaaa gtcgaattgc ttttgggtac cgttacctct aacacagttc aagaacaacc   180
caatgttgac caacattctg atacccaagg aagggtcaat gacagtcatc aactgcaatc   240
ttcttctaaa cttaccgtaa ggttcggttt ccaagaattt ggacatctgg ttgattctgt   300
tagcaaccaa ctctctttct tgcttttggg tgtagtcaaa ctgttctgat ctggtttgca   360
agattgggtc acgttcaatg gactggtaca agcgcaagat ttgttcagac tttccctcgt   420
caccttccaa gaactcgtgc atttctttca agtcccagtc ggtgcgtgct ctttcttcag   480
caacgtcctt ggctgggtgt ggtgggtcct ggaggaaat gacatcagca acttgctttg   540
gagttgtgtc tgggtccttc ttttgttggt ggtcgtgacc gtcgtgtgat tgactgagca   600
tagccattgt gttaaagtag tattcagttt tattaaagag gtgctaatta actgtgaatg   660
gttaatcaaa ggtaaaacta tacttgaaga agaggtaaaa caaggggggtt ttagaaaaaa   720
atcattcggt aaatcaagct ggttttaaat aattgacggg aatgaaccaa agtgtaagcc   780
cccccaccc gccaccacca ccttcaccac tacgaacact atgatttttt tttattaagc   840
gtgcatgcca aaaatcaaat gttttagta tcctccattt tttctttctc tctcccttg     900
tttccttcgt ccgctcccca cctttcggca tcaccatcgg                         940
```

SEQ ID NO: 41  moltype = DNA  length = 20
FEATURE    Location/Qualifiers
source     1..20
       mol_type = other DNA
       organism = synthetic construct
SEQUENCE: 41

```
ccttgagccg gagaacatca                                                20
```

SEQ ID NO: 42  moltype = DNA  length = 20
FEATURE    Location/Qualifiers
source     1..20
       mol_type = other DNA
       organism = synthetic construct
SEQUENCE: 42

```
ggagtagcga taccaaacgt                                                20
```

SEQ ID NO: 43  moltype = DNA  length = 20
FEATURE    Location/Qualifiers
source     1..20
       mol_type = other DNA
       organism = synthetic construct

```
SEQUENCE: 43
tcgttgattg gtaagtacga                                                 20

SEQ ID NO: 44           moltype = DNA   length = 3561
FEATURE                 Location/Qualifiers
source                  1..3561
                        mol_type = other DNA
                        organism = synthetic construct
SEQUENCE: 44
atgattgaac aaatcctaga atattggtat attgttgtgc ctgtgttgta catcatcaaa     60
caactcattg cctacagcaa gactcgcgtc ttgatgaaac agtgggtgc tgctccaatc     120
acaaccagt tgtacgacaa cgttttcggt atcgtcaacg gatggaaggc tctccagttc     180
aagaaagagg gcagagctca agagtacaac gatcacaagt tgacagctc caagaaccca     240
agcgtcggca cctatgtcag tattcttttt ggcaccaaga ttgtcgtgac caaggatcca     300
gagaatatca aagctatttt ggcaacccag tttggcgatt tttctttggg caagagacac     360
gctcttttta aacctttgtt aggtgatggg atcttcacct tggacggcga aggctggaag     420
catagcagat ccatgttaag accacagttt gccagagaac aagttgctca tgtgacgtcg     480
ttggaaccac acttccagtt gttgaagaag catatcctta aacacaaggg tgagtacttt     540
gatatccagg aattgttctt tagatttact gtcgactcgg ccacggagtt cttatttggt     600
gagtccgtgc actccttaaa ggacgaaact atcggtatca accaagacga tatagatttt     660
gctggtagaa aggactttgc tgagtcgttc aacaaagccc aggagtattt gtctattaga     720
attttggtgc agacctcta ctggttgatc aacaacaaga agtttagaga ctgtaccaag     780
ctggtgcaca agtttaccaa ctactatgtt cagaaagctt tggatgctac cccagaggaa     840
cttgaaaagc aaggcgggta tgtgttcttg tatgagcttg tcaagcagac gagagacccc     900
aaggtgttgc gtgaccagtc tttgaacatc ttgttggcag aagagacac cactgctggg    960
ttgttgtcct ttgctgtgtt tgagttggcc agaaacccac acatctggcc caagttgaga   1020
gaggaaattg aacagcagtt tggtcttgga agactctc gtgttgaaga gattacctttt   1080
gagagcttga agagatgtga gtacttgaaa gcgttcctta acgaaacctt gcgtgtttac   1140
ccaagtgtcc caagaaactt cagaatcgcc accaagaata caacattgcc aaggggtggt   1200
ggtccagacg gtacccagcc aatcttgatc caaaggggag aaggtgtgtc gtatggtatc   1260
aactctaccc acttagatcc tgtctattat ggccctgatg ctgctgagtt cagaccagag   1320
agatggtttg agccatcaac cagaaagctc ggctgggctt acttgccatt caacggtggg   1380
ccacgaatct gtttgggtca gcagtttgcc ttgaccgaag ctggttacgt tttggtcaga   1440
ttggtgcaag agttctccca cattaggctg gacccagatg aagtgtatcc accaaagagg   1500
ttgaccaact tgaccatgtg tttgcaggat ggtgctattg tcaagtttga cggatccgct   1560
ggctccgctg ctggttctgg cgaattcgct aagaaccagt tccttgatca gccccaggac   1620
accgggttcc tcaacacgga cagcggaagc aactccagag acgtcttgct gacattgaag   1680
aagaataata aaaacacgtt gttgttgttt gggtcccaga ccggtacggc agaagattac   1740
gccaacaaat tgtcaagaga attgcactcc agatttgact tgaaaaccat ggttgcagat   1800
ttcgctgatt acgattggga taacttcgga gatatcaccg aagatatctt ggtgttttttc   1860
atcgttgcca cctacggtga gggtgaacct ccgacaatgc ccgacgagtt ccacacctgg   1920
ttgactgaag aagctgacac tttgagtact ttgagatata ccgtgttcgg gttgggtaac   1980
tccacctacg agttcttcaa tgctattggt gaaaagttta acagattgtt gagtgagaaa   2040
ggtggtgaca gatttgctga atatgctgaa ggtgacgacg gcactggcac cttgacgaa   2100
gatttcatgc cctggaagga taatgtcttt gacgccttga agaatgactt gaactttgaa   2160
gaaaaggaat tgaagtacga accaaacgtg aaattgactg agagagatga cttgtctgct   2220
gccgactccc aagttccttt gggtgagcca aacaagaagt acatcaactc cgagggcatc   2280
gacttgacca agggtccatt cgaccacacc caccccatact tggccaggat caccgagacc   2340
agagagttgt tcagctccaa ggaaagacac tgtattcacg ttgaatttga catttctgaa   2400
tcgaacttga aatacaccac cggtgaccat ctagccatct ggccatccaa ctccgacgaa   2460
aacatcaagc aatttgccaa cgtgtttcgga ttggaagata aactcgacac tgttattgaa   2520
ttgaaggcat tggactccac ttacaccatt ccattcccaa ctccaattac ttacggtgct   2580
gtcattagac accattaga aatctccggt ccagtctcga acaattctt tttgtcgatt   2640
gctgggtttg ctcctgatga agaaacaaag aagactttca ccagacttgg tggtgacaaa   2700
caagaattcg ccaccaaggt tacccgcaga aagttcaaca ttgccgatgc cttgttatat   2760
tcctccaaca cactccatg gtccgatgtt ccttttgagt tccttattga aaacatccaa   2820
cacttgactc cacgttacta ctccattttct cttcgtcgt tgagtgaaaa acaactcatc   2880
aatgttactg cagtcgttga ggccgaagaa gaagccgatg cagaccagt cactggtgtt   2940
gttaccaact tgttgaagaa cattgaaatt gcgcaaaaca agctggcga agccactt   3000
gttcactacg atttgagcgg cccaagagcc aagttcaaca agttcaagtt gccagtgcac   3060
gtgagaagat ccaactttaa gttgccaaag aactccacca cccagttat cttgattggt   3120
ccaggtactg gtgttgcccc attgagaggt tcgttagag aaagagttca acaagtcaag   3180
aatggtgtca atgttggcaa gactttgttg ttttatggtt gcagaaactc caacgaggac   3240
tttttgtaca agcaagaatg ggccgagtac gcttctgttt tgggtgaaaa cttttgagatg   3300
ttcaatgcct tctctagaca agacccatcc aagaaggttt acgtccagga taagattta   3360
gaaaacagcc aacttgtgca cgaattgttg accgaaggtg ccattatcta cgtctgtggt   3420
gacgccagta gaatggccag agacgtccag accacgatct ccaagattgt tgccaaaagc   3480
agagaaatca gtgaagacaa ggccgctgaa ttggtcaagt cctggaaagt ccaaaataga   3540
taccaagaag atgttttggta g                                             3561

SEQ ID NO: 45           moltype = DNA   length = 3546
FEATURE                 Location/Qualifiers
source                  1..3546
                        mol_type = other DNA
                        organism = synthetic construct
SEQUENCE: 45
atgctcgatc agatcttaca ttactggtac attgtcttgc cattgttggc cattatcaac     60
cagatcgtgg ctcatgtcag gaccaattat ttgatgaaga aattgggtgc taagccattc    120
acacacgtcc aacgtgacgg gtggttgggc ttcaaattcg ccgtgaatt cctcaaagca    180
```

```
aaaagtgctg ggagactggt tgatttaatc atctcccgtt tccacgataa tgaggacact    240
ttctccagct atgcttttgg caaccatgtg gtgttcacca gggaccccga gaatatcaag    300
gcgcttttgg caacccagtt tggtgatttt tcattgggca gcagggtcaa gttcttcaaa    360
ccattattgg ggtacggtat cttcacattg gacgccgaag ctggaagcaa cagcagagcc    420
atgttgagac cacagtttgc cagagaacaa gttgctcatg tgacgtcgtt ggaaccacac    480
ttccagttgt tgaagaagca tatccttaaa cacaagggtg agtactttga tatccaggaa    540
ttgttcttta gatttactgt cgactcggcc acggagttct tatttggtga gtccgtgcac    600
tccttaaagg acgaggaaat tggctacgac acgaaagaca tgtctgaaga agacgcagaa    660
tttgccgacg cgttcaacaa gtcgcaagtc tacgtggcca ccagagttgc tttacagaac    720
ttgtactggt tggtcaacaa caaagagttc aaggagtgca atgacattgt ccacaagttt    780
accaactact atgttcagaa agccttggat gctaccccag aggaacttga aaagcaaggc    840
gggtatgtgt tcttgtatga gcttgtcaag cagacgagag accccaaggt gttgcgtgac    900
cagtcttttga acatcttgtt ggcaggaaga gacaccactg ctgggttgtt gtcctttgct    960
gtgtttgagt tggccagaaa cccacacatc tgggcaagt tgagagagga aattgaacag   1020
cagtttggtc ttggaagaa ctctcgtgtt gaagagatta cctttgagag cttgaagaga   1080
tgtgagtact tgaaggccgt gttgaacgaa actttgagat tacacccaag tgtcccaaga   1140
aacgcaagat ttgcgattaa agacacgact ttaccaagag gcggtggccc caacggcaag   1200
gatcctatct tgatcaggaa ggatgaggtg gtgcagtcat ccatctcggc aactcagaca   1260
aatcctgctt attatggcgc cgatgctgct gattttagac cggaaagatg gtttgaacca   1320
tcaactagaa acttgggatg ggcttttctt ccattcaacg gtggtccaag aatctgtttg   1380
ggacaacagt ttgctttgac tgaagccggt tacgttttgg ttagacttgt tcaggagttt   1440
ccaaacttgt cacaagaccc cgaaaccaag taccaccaa ctagattggc acacttgacg   1500
atgtgcttgt ttgacggtgc acacgtcaag atgtcaggat ccgctggctc cgctgctggt   1560
tctggcgaat cgctaagaa ccagttcctt gatcagcccc aggacaccgg gttcctcaac   1620
acggacagcg gaagcaactc cagagacgtc ttgctgacat tgaagaagaa taataaaaac   1680
acgttgttgt tgtttgggtc ccagaccggt acggcagaag attacgccaa caaattgtca   1740
agagaattgc actccagatt tggcttgaaa accatggttg cagatttcgc tgattacgat   1800
tgggataact tcggagatat caccgaagat atcttggtgt ttttcatcgt tgccacctac   1860
ggtgagggtg aacctaccga caatgccgac gagttccaca cctggttgac tgaagaagct   1920
gacactttga gtactttgag atataccgtg ttcgggttgc gtaactccac ctacgagttc   1980
ttcaatgcta ttggtagaaa gtttgacaga ttgttgagtg agaaaggtgg tgacagattt   2040
gctgaatatg ctgaaggtga cgacggcact ggcaccttgg acgaagattt catggcctgg   2100
aaggataatg tctttgacgc cttgaagaat gacttgaact tgaagaaaa ggaattgaag   2160
tacgaaccaa acgtgaaatt gactgagga gatgacttgt ctgctgccga ctcccaagtt   2220
tccttgggtg agccaaacaa gaagtacatc aactccgagg gcatcgactt gaccaagggt   2280
ccattcgacc acaccaccc atacttggcc aggatcaccg agaccagaga gttgttcagc   2340
tccaaggaaa gacactgtat tcacgttgaa tttgacattt ctgaatcgaa cttgaaatac   2400
accaccggtg accatctagc catctggcca tccaactccg acgaaaacat caagcaattt   2460
gccaagtgtt tcggattgga agataaactc gacactgtta ttgaattgaa ggcattggac   2520
tccacttaca ccattccatt cccaactcca attacttacg gtgctgtcat tagacaccat   2580
ttagaaatct ccggtccagt ctcgagacaa ttctttttgt cgattgctgg gtttgctcct   2640
gatgaagaaa caaagaagac tttccaccaga cttggtggtg acaaacaaga attcgccacc   2700
aaggttaccc gcagaaagtt caacattgcc gatgccttgt tatattccct caacaacact   2760
ccatggtccg atgttccttt tgagttcctt attgaaaaca tccaactt gactccacgt   2820
tactactcca tttctttcttc gtcgttgagt gaaaaacaac tcatcaatgt tactgcagtc   2880
gttgaggccg aagaagaagc cgatggcaga ccagtcactg tgttgttac caacttgttg   2940
aagaagactg aaattgcgca aaacaagact ggcgaaaagc cacttgttca ctacgatttg   3000
agcggcccaa gaggcaagtt caacaagttc aagttgccag tgcacgtgag aagatccaac   3060
tttaagttgc caaagaactc caccaccca gttatcttga ttggtccagg tactggtgtt   3120
gccccattga gaggtttcgt tagagaaaga gttcaacaag tcaagaatgg tgtcaatgtt   3180
ggcaagcttt tgttgttta tggttgcaga aactccaacg aggactttt gtacaagcaa   3240
gaatgggccg agtacgcttc tgttttgggt gaaaactttg agatgttcaa tgccttctct   3300
agacaagacc catccaagaa ggtttacgtc caggataaga ttttagaaaaa cagccaactt   3360
gtgcacgaat tgttgaccga aggtgccatt atctacgtct gtggtgacgc cagtagaatg   3420
gccagagacg tccagaccac gatctccaag attgttgcca aaagcagaga aatcagtgaa   3480
gacaaggccg ctgaattggt caagtcctgg aaagtccaaa atagatacca agaagatgtt   3540
tggtag                                                             3546

SEQ ID NO: 46           moltype = DNA  length = 2115
FEATURE                 Location/Qualifiers
source                  1..2115
                        mol_type = genomic DNA
                        organism = Candida viswanathi
SEQUENCE: 46
atggctccat ttttgcccga ccaggtcgac tacaaacacg tcgacaccct tatgttatta     60
tgtgacggga tcatccacga aaccaccgtg gacgaaatca aagacgtcat tgcccctgac    120
ttccccgccg acaaatacga ggagtacgtc aggacattca ccaaaccctc cgaaacccca    180
gggttcaggg aaaccgtcta caaccacgtc aacgcaaaca ccatggatgc aatccaccag    240
tcattatctc tgaccaatgt tttgggatca agggtcttgg caccagtctt gaccaactcg    300
ttgactccta tcaaggacat gagcttgaa gaccgtgaaa agttgttagc ctcgtggcgt    360
gactccccta ttgctgctaa aaggaagttg ttcaggttgg tttctacgct taccttggtc    420
acgttccacga gattggccaa tgagttgcat ttgaaagcca ttcattatcc aggaagagaa    480
gaccgtgaaa aggcttatga aaccccagag attgacccct taagtacca gttttttgaa    540
aaaccgaagt tttacgtcgc tgagttgtac ttgccagata ttgatgtgat cattattgga    600
tctggggccg gtgctggtgt cgtgcccac actttgacca acgacggctt caagagtttg    660
gttttgaaaa agggcagata ctttagcaac tccgagttga actttgatga caaggacggg    720
gttcaagaat tatacccaaag tggaggtact ttgaccaccg tcaaccagca gttgtttgtt    780
cttgctggtt ccacttttgg tggtggtacc actgtcaatt ggtcggcctg tcttaaaacg    840
ccattcaagg tgcgtaagga atggtatgat gagtttggcg ttgactttgc tgccgatgaa    900
```

```
gcctacgaca aagcacagga ttatgtttgg cagcaaatgg gagcttctac cgaaggcatc    960
acccactctt tggctaacga gattattatt gaaggtggca agaaattagg ttacaaggcc   1020
aaggtattag accaaaacag cggtggtcat cctcatcaca gatgcggttt ctgttatttg   1080
ggttgtaagc acggtatcaa gcagggctct gttaataact ggtttagaga cgcagctgcc   1140
cacggttctc agttcatgca acaggttaga gttttgcaaa tccttaacaa gaagggcatc   1200
gcttatggta tcttgtgtga ggatgttgta accggtgcca agttcaccat tactggcccc   1260
aaaaagtttg ttgttgccgc cggcgcctta aacactccat ctgtgttggt caactccgga   1320
ttcaagaaca agaacatcgg taagaactta actttgcatc cagtttctgt cgtgtttggt   1380
gattttggca agacgttca agcagatcac ttccacaact ccatcatgac tgctctttgt   1440
tcagaagccg ctgatttaga cggcaagggt catggatgca gaattgaaac catcttgaac   1500
gctccattca tccaggcttc attcttacca tggagaggta gtaacgaggc tagacgagac   1560
ttgttgcgtt acaacaacat ggtggccatg ttacttctta gtcgtgatac caccagtggt   1620
tccgtttcgt cccatccaac taaacctgaa gcattagttg tcgagtacga cgtgaacaag   1680
tttgacagaa actccatctt gcaggcattg ttggtcactg ctgacttgtt gtacattcaa   1740
ggtgccaaga gaatccttag tccccaacca tgggtgccaa tttttgaatc cgacaagcca   1800
aaggataaga gatcaatcaa ggacgaggac tatgtcgaat ggagagccaa ggttgccaag   1860
attccttttg acacctacgg ctcgcttat ggttcggcgc atcaaatgtc ttcttgtcgt   1920
atgtcaggta agggtcctaa atacggtgct gttgatacg gtggtagatt gtttgaatgt   1980
tcgaatgttt atgttgctga cgctagtctt ttgccaactg ctagcggtgc taatcctatg   2040
gtcaccacca tgactcttgc aagacatgtt gcgttaggtt tggcagactc cttgaagacc   2100
aaggccaagt tgtag                                                   2115

SEQ ID NO: 47          moltype = DNA    length = 516
FEATURE                Location/Qualifiers
source                 1..516
                       mol_type = genomic DNA
                       organism = Candida viswanathi
SEQUENCE: 47
tatttcggga gaaatatcgt tggggtaaaa caacagagag agagagggag agatggttct    60
ggtagaatta taatctggtt gttgcaaatg ctactgatcg actctggcaa tgtctgtagc   120
tcgctagttg tatgcaactt aggtgttatg catacacacg gttattcggt tgaattgtgg   180
agtaaaaatt gtctgagttg tgtcttagct actggctggc ccccgcgaa agataatcaa   240
aattacactt gtgaatttt gcacacacac cgattaacat ttccttttt tgtccaccga   300
tacacgcttg cctcttcttt tttttctctg tgcttccccc tcctgtgact tttccacca   360
ttgatataaa atcaactcca tttccctaaa atctccccag attctaaaaa caacttcttc   420
tcttctgctt ttcctttttt tttgttatat ttatttacca tccctttttt ttgaatagtt   480
attccccact aacattgttc aaatcttcac gacata                             516

SEQ ID NO: 48          moltype = DNA    length = 581
FEATURE                Location/Qualifiers
source                 1..581
                       mol_type = genomic DNA
                       organism = Candida viswanathi
SEQUENCE: 48
ttgtgtagga ggagcggaga taaattagat ttgattttgt gtaaggtttt ggatgtcaac    60
ctactccgca cttcatgcag tgtgtgtgac acaaggtgt actacgtgtg cgtgtgcgcc   120
aagagacagc ccaaggggt ggtagtgtgt gttggcggaa gtgcatgtga cacaacgcgt   180
gggttctggc caatggtgga ctaagtgcag gtaagcagcg acctgaaaca ttcctcaacg   240
cttaagacac tggtggtaga gatgcggacc aggctattct tgtcgtgcta cccggcgcat   300
ggaaaatcaa ctgcgggaag aataaattta tccgtagaat ccacagagcg gataaatttg   360
cccacctcca tcatcaacca cgccgccact aactacatca ctcccctatt ttctctctgt   420
ctcttgtct tactccgctc ccgtttcctt agccacagat acacacccac tgcaaacagc   480
agcaacaatt ataagatac gccaggccca ccttctttct tttttctcac tttttttgact   540
gcaactttct acaatccacc acagccacca ccacagccgc t                       581

SEQ ID NO: 49          moltype = DNA    length = 645
FEATURE                Location/Qualifiers
source                 1..645
                       mol_type = genomic DNA
                       organism = Candida viswanathi
SEQUENCE: 49
gtcggcgaac ttgacaaggt gttcaaggat gaaaagtttg ccgtcaacga caagattaga    60
ttggttgaga tcatgttaga cactttcgat gctccagaga acttggttaa gcaagctgag   120
agatctgcca acaccaacaa gtagagtttg tctatgtttt ccgtttgcct tttctttcta   180
gtacagacg ttattgaacg aagttttat atatctagat ctaatacata ttccatgtct   240
gttcattttt gacggagttt cataaggtgg cagtttctaa tcaaggtcc gtcattggcg   300
tcgtggcatt ggcggctcgc atcaactcgt atgtcaatat tttctgttaa ctccgccaga   360
catacgatca aaacctacaa gcaaaaaaat tccacatgct ttgtttgaa tctccacaga   420
caacaacggg gtaagaaaat catgggggcga ttaatcatgc catctttgta aatttctttg   480
tttcaacatc accctcttta gtcaaacctt cacaggactg tctgctctac tttgccaccc   540
agttcatata taaattacca acttccaccg agcaccacca acacctcacc ccactctctc   600
ccccccctt ttttttccag cttagacaca cacttcaaac tcgac                    645

SEQ ID NO: 50          moltype = DNA    length = 1500
FEATURE                Location/Qualifiers
source                 1..1500
                       mol_type = genomic DNA
                       organism = Candida viswanathi
SEQUENCE: 50
```

```
atgtcttatg attcattcgg tgactacgtc actatcgtcg ttttcggtgc ttccggtgac    60
ttggccagca aaaaaacctt ccctgccttg tttggcttgt ttagagaaaa gcaattgccc   120
ccaaccgtcc agatcattgg ctatgccaga tcccatttgt ccgacaagga cttcaaaacc   180
aagatctcct cccacttcaa gggcggcgac gaaaaaacca agcaagactt cttgaacttg   240
tgtacttata tcagcgaccc atacgacact gacgatggtt acaagagatt ggaagccgcc   300
gctcaagaat acgaatccaa gcacaacgtc aaggtccctg aaagattgtt ttacttggcc   360
ttgcctcctt ctgtcttcca caccgtctgt gagcaagtca agaagatcgt ctaccctaag   420
gacggtaagc tcagaatcat cattgaaaag ccgttcggac gtgatttggc cacctaccgt   480
gaattgcaaa agcaaatctc cccattgttc accgaagacg aactctacag aattgaccac   540
tacttgggta aagaaatggt caagaacttg ttggttttga gattcggtaa cgaattgttc   600
agtgggatct ggaacaacaa gcacatcacc tcggtgcaaa tctccttcaa ggaacccttc   660
ggtaccgaag gtagaggtgg ctactttgac aacattggta tcatcagaga tgtcatgcaa   720
aaccactgt tgcaagtctt gaccttgttg accatgaaa gaccagtctc ttttgaccca   780
gaagctgtca gagacgaaaa ggtcaaggtt ttgaaagctt ttgacaagat tgacgtcaac   840
gacgttcttt tgggacaata cgccaagtct gaggatggcc ccaagccagg ttacttggat   900
gactccaccg tcaagccaaa ctccaaggct gtcacctacg ccgctttcag agtcaacatc   960
cacaacgaaa gatgggacgg tgttccaatt gttttgagag ccggtaaggc tttagacgaa  1020
ggtaaagttg aaattagaat ccaattcaag ccagttgcca aagtatgtt taaggagatc  1080
caaagaaacg aattggttat tagaatccaa ccagacgaag ccatctactt gaagatcaac  1140
tccaagatcc caggtatctc caccgaaact tccttgaccg acttggactt gacttactcc  1200
aagcgttact ccaaggactt ctggatccca gaagcatacg aagccttgat cagagactgt  1260
tacttgggca accactccaa cttttgtcaga gacgatgaat tggaagttgc ttggaagctc  1320
ttcaccccat tgttgaagc cgttgaaaaa gaagacgaag tcagcttggg aacctaccca  1380
tacggatcca agggtcctaa agaattgaga aagtacttgg tcgaccacgg ttacgtcttc  1440
aacgacccag gtacttacca atggccattg accaacaccg atgtcaaggg taagatctaa  1500
```

SEQ ID NO: 51          moltype = DNA   length = 2010
FEATURE                Location/Qualifiers
source                 1..2010
                       mol_type = genomic DNA
                       organism = Candida viswanathi
SEQUENCE: 51
```
atgtcttcag ctccaaagta tgtacctcaa ttcgttttta tcaattggaa caagagagat    60
aggacggcag aattccagag attggacagg aacaagaaca attaggcaat gggcgagcgg   120
aaatcaattg gatctactca attgatattt ttaaccagaa cccacccact tggcaatata   180
ctcaacatgt ccgttccacc ccctcctag aaattttcac attggctgga atttttttt    240
aggaggagat gaaatcgttg agaaccgagc gttcctcgcc cccaaatttt tttctgttc    300
ggctcacacg cccaagggat caaggataat cagctgcaag gaaaaaaat aaagtataaa    360
gagaatgccg tttttccccc acattgaaag tttttcaga ttttgcaac ccaacgtta    420
tcaagttctt tttttttgg caacacgtct tcccaaatgt ccaatcccaa agctgtcttt   480
aggttatctg ctctatccaa gcaaatcgcg accaacaata ctaacaatct gattgctaga   540
ggtgatatcg gtttgattgg tttagccgtc atgggtcaaa acttgatcct taacatggct   600
gaccacggtt acactgttgt tgcttacaac agaaccacct ccaaggttga ccacttcttg   660
gccaacgaag ctaagggcaa gtctatcctc ggtgctcact ccatccaaga attggttgac   720
caattgaaga gaccaagaag aattatgctt tggtcaagg ccggtgctcc cgttgacagt   780
ttcattgacc aattggtccc atacttgaa gaaggtgaca tcatcattga cggtggtaac   840
tcccacttcc cagacaccaa cagaagatac gacgacttga agaagaaggg tatcttgttt   900
gtcggttccg tgtctctgg tggtgaagaa ggtgccagaa ctggtccatc tttgatgcca   960
ggtggtaacg aagctgcttg gccacacatc aaggacatct ccaagacat ctccgccaag  1020
gctgacggta accatgttg tgactgggtt ggtccagcgg gtgccggtca ctacgtcaag  1080
atggtccaca acgtattga atacggtgac atgcaattga tttgtgaagc tacgacctc  1140
atgaagagag ttggtaagtt ctccaacaag gaaatgggtg acgttttcgc caagtggaac  1200
aagggtgttt tggactcttt cttgattgaa atcaccagag acattatgta ctacgacgac  1260
ccaactgacg gtaccccatt ggttgaaaag atcttggaca cagccggtca aaagggtact  1320
ggtaagtgga ctgctgtcaa cgcccttgac ttgggtatcc ctcttacctt ggttggtaa   1380
gccgtcttct ccagatgttt gtctgctttg aagaacgaaa gagttgaagc ctccaagcac  1440
ttgccaggtc caaagattga tgaacttcct ccaatcacca caaggaaga attcattgac  1500
cacttggaac aagccttgta cgcctccaag attatctcct acaccaaggg tttcatgttg  1560
atgaaccaag ctgccaagga ctacgttgg aagttgaaca atgctggtat tgccttgatg  1620
tggagaggtg gttgtatcat cagatccgtc ttcttgggtg agatcactgc tgcttacaga  1680
aagaagccag acttggaaaa cttgttgctc tacccattct tcaacgaagc catcaccaag  1740
gcccaaaagg gatggagaac ctctgtttct agagctgttg aatacggtgt cccaccccca  1800
gctttcagca ctgccttggc cttctacgat ggtttgagat ccgcacaatt gccagccaac  1860
ttgttgcaag cccaaagaga ctacttcggt cccacacct tccaagtctt gccaggtaag  1920
gaaaactcct tgttgaagaa gggtgaatgg atccacatca actggaccgg taagggtggt  1980
aacgtctcct cttcatctta tgacgcttag                                   2010
```

SEQ ID NO: 52          moltype = DNA   length = 1221
FEATURE                Location/Qualifiers
source                 1..1221
                       mol_type = genomic DNA
                       organism = Candida viswanathi
SEQUENCE: 52
```
atgtctttaa caccacaagg agcacagctc ctttcaatca agcagtgttc ggaattacca    60
aaggctcgct tacccgaata catcaagtca tccaaaagca gactatacaa cgtgatatgg   120
agggcttctc caccgaccaa cgtctacatt gccaagaaac cgtgggaacc atcggtgcac   180
agggcgatga ttgagttcat caaccacttg cacaggagt atccgtcgat caacatcatc   240
gtgaacgagg acgtggcaga ggagctccgt gaagaatacg aggaccccca ggaggaaacc   300
aggttttgaca ccagcgtcca ccatgtgata tacacgggaa agaaccagga cattgtggac   360
```

```
aagaccgagt tgatggttac gttaggtggg gacgggacga tcttgcatgg cgcgagcttg    420
ttcctgaacg tcaatgtccc acccgtgttg tcgttcgcta tgggaacgtt ggggttcttg    480
ttgcctttca atttcaagaa cttccagctg agtttcaaag aggtttatga gagtaggagc    540
aaggcattgc atagaaaccg attggagtgt catgttatta gaaagaacgg gaatgggaaa    600
caagacaacg atgaactgca cccaaagaaa aagtacaagg tggatcaagg acgtgttgtt    660
gatgttcctg atactgataa taactcaagg gagatgatcc atgccatgaa tgacgtcacg    720
atccatagag ccagcttacc gaacttgaca tcattggaca tctacattga caacgagttt    780
ttcaccacga cgtttgccga tggtgtgatc ttagccaccc caactggatc gaccgcgtat    840
tcattatcag caggcgggtc catcacccac ccagcagtgc catgcatatt gctcaccccg    900
atctgcccaa gatcattatc attcagacct ttgatcctcc ccagtctgtc agacatcatg    960
gtgaagttat ctgagaacaa cagaaacaac atgatcgaat tgactatcga cggtatcgca   1020
caacctgact tgcatcctgg tgatgagttg cacatcacct ctgaagatat cgtcccggt    1080
gctgatcttt ccaaaacaaa cgcgaagaac gggatatggt gtgtcgcgac acatcagaac   1140
cagtgggcca aagacttgaa cagcttgtta gggttcaaca gcctgttcag ggaccagaag   1200
ggtaagaagt tgcatttgta a                                             1221

SEQ ID NO: 53           moltype = DNA  length = 1071
FEATURE                 Location/Qualifiers
source                  1..1071
                        mol_type = genomic DNA
                        organism = Kluyveromyces lactis
SEQUENCE: 53
atgccagata tgacaaacga atcttcttct aagccagctc aaattaacat tggtatcaat     60
ggttttggta gaatcggtag attggttttg cgtgctgctt tgacccaccc agaagttaag    120
gtcagattaa tcaataatcc atccacaaca ccagaatacg ctgcttattt gttcaaatac    180
gattctactc acggcaagta tcgtggtgaa gttgaatttg acgatgaacg tatcatcatt    240
caaaatgacc atgtttccgc tcatatccct ttgtctcatt ttagagaacc agagcgtatc    300
ccatgggctt cctacaacgt cgattatgtt attgactcaa ctggtgtttt caaggaagtc    360
gatacagcct ccagacataa aggtgtcaaa aaagttatca ttactgctcc atcaaagacc    420
gctccaatgt acgtctatgg tgttaaccac gttaaataca acccattgac cgatcacgtt    480
gtctctaatg cctcctgtac taccaactgt ttggctccat tggttaaggc tttgacgat     540
gagttcggta tcgaagaagc cttgatgaca actattcatg caactactgc ttctcaaaag    600
actgtcgatg gtacttcctc tggtggtaag gactggagag gcggtagatc ctgccaggga    660
aatatcattc cttcatctac tggtgcagct aaggctgttg gtaaatcttc gcctgaattg    720
aatggtaaga tcactggtat gtctattaga gtcccaacaa ttaatatctc tttggttgac    780
ttgacattcc gtacagcaaa gaaaacttct tacgatgaca ttatgaaggc tttgaacaa     840
agatccagat ccgatatgaa gggtgttttg ggtgttacca agacgccgt tgtgtcctct    900
gacttcacat ccgattcacg ttcatctatt gttgatgcta aggccggtat tgaattgaac    960
gaccattttt tcaaggtctt tgtcttggtat gataatgaat atggttactc ttcaagagtg   1020
gttgatttat ccatttcat ggctcaaaag gactttgaag ctggtgttta a              1071

SEQ ID NO: 54           moltype = DNA  length = 1530
FEATURE                 Location/Qualifiers
source                  1..1530
                        mol_type = other DNA
                        organism = synthetic construct
SEQUENCE: 54
atgagaattg gcattccaag agaaagatta accaatgaaa cccgtgttgc agcaacccca     60
aaaacagtgg aacagttgtt gaaattgggt tttaccgtcg ctgttgagtc cggcgctggt    120
cagttggcaa gttttgacga taaagccttt gtgcaagctg cgctgaaat tgttgaaggt    180
aattccgtct ggcagtcaga gatcattttg aaggtcaatg ctccattaga tgatgaaatt    240
gctttattga atcctggtac aaccttggtg agttttatct ggcctgctca gaatccagaa    300
ttaatgcaaa aattggctga acgtaacgtg accgtgatgg ctatggactc tgtgccacgt    360
atctcaagag cacaatcctt ggacgcattg tcctctatgg ctaacatcgc cggttataga    420
gccattgttg aagctgcaca tgaatttggt agattcttta ctggtcaaat tactgctgcc    480
ggtaaagtgc caccagcaaa agtgatggtg attggtgctg tgttgcagg tttggccgcc    540
attggcgcag caacagtttt gggcgctatt gtgcgtgcat tcgacaccag accagaagtg    600
aaagaacaag ttcaaagtat gggcgctgaa ttttggagt tggattttaa agaggaagct    660
ggctccggcg atggctatgc caaagtgatg tccgacgctt tcatcaaagc tgaaatggaa    720
ttgtttgccg cccaggcaaa agaggtcgat attattgtca ccaccgcttt gattccaggc    780
aaaccagctc caaagttgat tacccgtgaa atggttgact ccatgaaggc tggcagtgtg    840
attgttgact ggcagcccca aaacggcggc aactgtgaat acaccgtgcc aggtgaaatc    900
ttcactaccg aaaatggtgt caaagtgatt ggttatacccg atttgccagg ccgtttgcca    960
acccaatcct cacagttgta cggcacaaac ttggttaatt tgttgaaatt gttgtgcaaa   1020
gagaagacg gcaatatcac tgttgatttt gatgatgtgt gattagagg cgtgaccgtg   1080
atccgtgctg gcgaaattac ctggccagca ccaccaattc aggtttcagc tcagccacag   1140
gctgcacaaa aagctgcacc agaagtgaaa actgaggaaa aatgtacctg ctcaccatgg   1200
cgtaaatacg ctttgatggc tttggcaatc attttgtttg gctggatggc atccgttgct   1260
ccaaaagaat ttttgggtca cttcaccgtt tcgctgcttg cggttattac              1320
gtggtgtgga atgtttccca cgctttgcat acaccattga tgtccgtcac caacgctatt   1380
tcaggtatta tgttgtcgg agcattgttg cagattggcc agggcggctg ggtttccttc   1440
ttgagtttta tcgctgtgtt gattgcctcc attaatattt tcggtggctt caccgtgact   1500
cagagaatgt tgaaatgtt cagaaaaaat                                     1530

SEQ ID NO: 55           moltype = DNA  length = 1389
FEATURE                 Location/Qualifiers
source                  1..1389
                        mol_type = other DNA
                        organism = synthetic construct
```

-continued

```
SEQUENCE: 55
atgtctggag gattagttac agctgcatac attgttgccg ctatcttgtt tatcttcagt    60
ttggccggtt tgtccaaaca tgaaacctcc agacagggta acaacttcgg tatcgccggt   120
atggctattg ctttaatcgc aaccattttt ggaccagata ctggtaatgt tggctggatc   180
ttgttggcta tggtcattgg tggtgctatt ggtatccgtt tggctaagaa agttgaaatg   240
accgaaatgc cagaattggt ggctatcttg cattccttcg tgggtttggc tgccgtcttg   300
gttggcttta actcctattt gcatcatgac gctggaatgg caccaattt ggtcaatatt    360
cacttgaccg aagtgttctt gggtatcttc atcggtgctg ttaccttcac tggttccgtg   420
gtggctttcg gcaaattgtg tggcaagatt tcctctaaac cattgatgtt gccaaaccgt   480
cacaaaatga acttggctgc tttggtcgtt tccttcttgt tgttgattgt ttttgttaga   540
accgactccg tcggcttgca agtgttggca ttgttgatta tgaccgctat tgctttggtt   600
ttcggctggc atttagtcgc ctccatcggt ggtgcagata tgccagtggt ggtgtccatg   660
ttgaactcct actccggctg ggctgccgcc gctgccggct ttatgttgtc caacgacttg   720
ttgattgtga ctggtgcttt ggtcggttct tccggtgcta tcttgtctta cattatgtgt   780
aaggctatga accgttcctt tatctccgtt attgctggtg gtttcggcac cgacggctcc   840
tctactggcg atgatcagga agtgggtgag cacagagaaa tcaccgcaga agagacagct   900
gaattgttga aaaactccca ttcagtgatc attactccag gttacggcat ggcagtcgct   960
caggctcaat atcctgtcgc tgaaattact gagaaattga gagctagagg tattaatgtg  1020
cgtttcggta tccacccagt cgctggtcgt ttgcctggac acatgaacgt tttgttggct  1080
gaagcaaaag ttccatacga catcgtgttg gaaatggacg agatcaatga tgactttgct  1140
gataccgata ccgttttggt gattggtgct aacgataccg ttaacccagc tgctcaggat  1200
gatccaaaga gtccaatcgc tggtatgcct gtgttggaag tgtggaaagc tcagaacgtg  1260
attgtcttta aacgttccat gaacactggc tatgctggtg tgcaaaaccc attgttcttc  1320
aaggaaaaca cccacatgtt gtttggtgac gccaaagcct ccgtggatgc aatcttgaag  1380
gctttgtaa                                                          1389
```

TRANSFORMANT FOR PRODUCING DODECANEDIOIC ACID AND METHOD FOR PRODUCING DODECANEDIOIC ACID

RELATED APPLICATIONS

This application claims priority to Taiwan Application Serial Number 111137112, filed Sep. 29, 2022, which is herein incorporated by reference.

SEQUENCE LISTING XML

A sequence listing XML submitted as an xml file via EFS-WEB is incorporated herein by reference. The sequence listing XML file submitted via EFS-WEB with the name "CP-5702-US_SEQ_LIST" was created on Mar. 21, 2023, which is 101,547 bytes in size.

BACKGROUND

Technical Field

The present disclosure relates to a gene editing technology of a microorganism. More particularly, the present disclosure relates to a gene editing system of *Candida viswanathii* and uses thereof.

Description of Related Art

*Candida viswanathii* is a budding yeast that can spontaneously convert long-chain alkanes to the corresponding acids/diacids and consume them as carbon sources for growth via the β-oxidation pathway. Gene-edited strains improved by metabolic engineering are promising cell factories for industrial applications. For example, enzymes involved in related oxidative metabolic pathways can be blocked, while the key enzymes that convert alkanes to acids/diacids can be retained and/or enhanced, so that the gene-engineered strains can consume alkanes stably and continuously, and use the carbon flux in the body for the production of acid/diacid chemicals.

However, most of the current gene engineering of *Candida viswanathii* is performed by high-pressure selective homologous recombination, which is not only has a low probability of recombination, but also can only edit one gene in one gene editing process. The high-pressure selective homologous recombination is very limited by the size and editing site of the deleted/inserted edited fragment, which is laborious and time-consuming. In addition, *Candida viswanathii* is one of *Candida* species having diploid genomes with multiple homologous chromosomes. Due to the characteristic of the parasexual cycle, *Candida viswanathii* may not undergo meiosis during reproduction, but gradually lose some chromosomes in multiple mitosis and then restore to the original ploidy, resulting in deletion or recombination of edited fragments, greatly increasing the instability of the strain and operational difficulty of gene editing engineering.

CRISPR-Cas9 gene editing technology has been widely used in various organisms in recent years, which can precisely and seamlessly target editing of chromosomes, overcoming the bottlenecks of editing efficiency and editing technology faced by biology-related fields. Although the CRISPR-Cas9 gene editing technology has excellent cutting ability, DNA sizes of the expression cassette of the Cas9 protein and the sgRNA used to guide the cleavage of the Cas9 protein are quite large. In addition, the DNA size of the entire editing system also will be too large due to the insertion of the expression cassettes of other exogenous genes that need to be integrated, which will affect the editing effect. Although the CRISPR-Cas9 system has been available for many years and has been improved many times, it has not yet been successfully established in *Candida viswanathii*. Therefore, establishing a gene editing technology in *Candida viswanathii* that can perform gene editing with high efficiency and enable the edited target to stably exist in a transformant is an important issue faced by fields at present.

SUMMARY

According to one aspect of the present disclosure, a gene editing system of *Candida viswanathii* includes a *Candida viswanathii*, a first gene editing fragment and a second gene editing fragment. The first gene editing fragment successively includes a first homology arm and a screening gene. The second gene editing fragment is connected to a C-terminus of the first gene editing fragment, and successively includes a second homology arm, a Cas9 expression cassette and a sgRNA cassette. The Cas9 expression cassette successively includes a Cas9 promoter, a Cas9 gene and three nuclear localization sequences. The sgRNA cassette successively includes a sgRNA promoter, a first ribozyme, a targeting sequence, a scaffold and a second ribozyme. The first gene editing fragment and the second gene editing fragment are constructed as a linear fragment for gene editing of a chromosome of the *Candida viswanathii*. The first homology arm and the second homology arm respectively correspond to a specific fragment of a gene on the chromosome of the *Candida viswanathii*, and the targeting sequence corresponds to a specific sequence of the gene on the chromosome of the *Candida viswanathii*.

According to another aspect of the present disclosure, a gene editing method of *Candida viswanathii* includes steps as follows. A first gene editing fragment is constructed, wherein the first gene editing fragment successively includes a first homology arm and a screening gene. A second gene editing fragment is constructed, wherein the second gene editing fragment is connected to a C-terminus of the first gene editing fragment, and successively includes a second homology arm, a Cas9 expression cassette and a sgRNA cassette. The Cas9 expression cassette successively includes a Cas9 promoter, a Cas9 gene and three nuclear localization sequences. The sgRNA cassette successively includes a sgRNA promoter, a first ribozyme, a targeting sequence, a scaffold and a second ribozyme. The first gene editing fragment and the second gene editing fragment are constructed as a linear fragment for gene editing of a chromosome of a *Candida viswanathii*. The first homology arm and the second homology arm respectively correspond to a specific fragment of a gene on the chromosome of the *Candida viswanathii*, and the targeting sequence corresponds to a specific sequence of the gene on the chromosome of the *Candida viswanathii*. A transformation step is performed, wherein the first gene editing fragment and the second gene editing fragment are transformed into the *Candida viswanathii* to obtain a transformant. A transformant cultivation step is performed, wherein the transformant is cultivated in a selection medium at an editing temperature for an editing time, the Cas9 expression cassette expresses the Cas9 gene, the sgRNA cassette expresses the targeting sequence, the first homology arm and the second homology arm are respectively homologously recombined with the specific fragment, and the first gene editing fragment and the second gene editing fragment located between the first homology arm and the second homology arm are integrated into the gene of the transformant.

According to still another aspect of the present disclosure, a transformant for producing dodecanedioic acid includes a host cell and at least two exogenous genes. The host cell is *Candida viswanathii*. The at least two exogenous genes includes CYP52A19 gene and CPRb gene, and the at least two exogenous genes are integrated into a chromosome of the host cell by the gene editing system of *Candida viswanathii* according to the aforementioned aspect.

According to yet another aspect of the present disclosure, a method for producing dodecanedioic acid includes steps as follows. A reaction substrate is provided, wherein the reaction substrate includes dodecane. A fermentation step is performed, wherein the reaction substrate is inoculated with the transformant for producing dodecanedioic acid according to the aforementioned aspect, and then is cultured at a fermentation condition for a fermentation time to obtain a fermented substance, and the fermented substance includes dodecanedioic acid.

BRIEF DESCRIPTION OF THE DRAWINGS

The present disclosure can be more fully understood by reading the following detailed description of the embodiment, with reference made to the accompanying drawings as follows:

FIG. 14A shows Table 2 listing SEQ ID NOs and their corresponding genes and primers referred in FIG. 5A, FIG. 5D, FIG. 6C, FIG. 7 and FIG. 9A.

FIG. 14B shows Table 3 listing SEQ ID NOs and their corresponding genes and primers referred in FIG. 10A, FIG. 10C, FIG. 11B and FIG. 12A.

DETAILED DESCRIPTION

[Gene Editing System of *Candida viswanathii*]

A gene editing system of *Candida viswanathii* of the present disclosure includes a *Candida viswanathii*, a first gene editing fragment 110 and a second gene editing fragment 120. The second gene editing fragment 120 is connected to a C-terminus of the first gene editing fragment 110, and the first gene editing fragment 110 and the second gene editing fragment 120 are constructed as a linear fragment 100 for gene editing of a chromosome of the *Candida viswanathii*.

Figure 1:
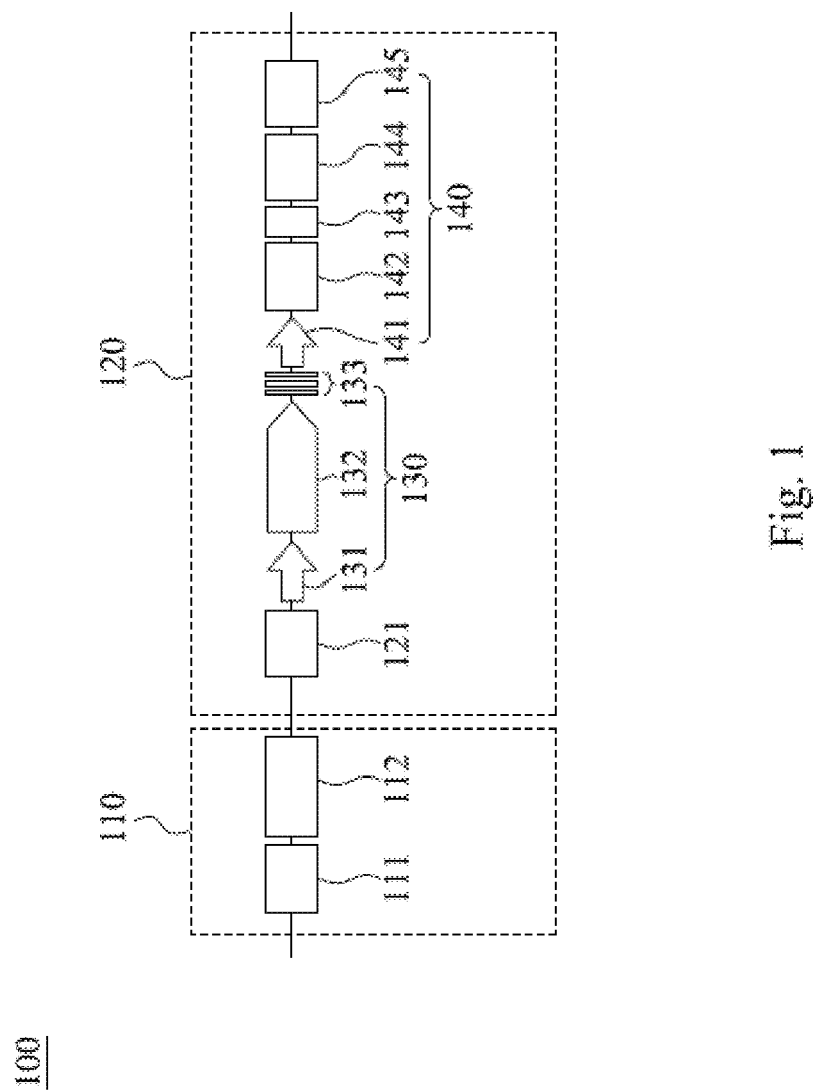
FIG. 1 is a schematic view showing a linear fragment of a gene editing system of *Candida viswanathii* according to one embodiment of one aspect of the present disclosure.

Reference is made to FIG. 1, which is a schematic view showing a linear fragment 100 of the gene editing system of *Candida viswanathii* according to one embodiment of one aspect of the present disclosure. In FIG. 1, the linear fragment 100 includes the first gene editing fragment 110 and the second gene editing fragment 120. The first gene editing fragment 110 successively includes a first homology arm 111 and a screening gene 112. The second gene editing fragment 120 is connected to a C-terminus of the first gene editing fragment 110, and the second gene editing fragment 120 successively includes a second homology arm 121, a Cas9 expression cassette 130 and a sgRNA cassette 140. The Cas9 expression cassette 130 successively includes a Cas9 promoter 131, a Cas9 gene 132 and three nuclear localization sequences 133. The sgRNA cassette 140 successively includes a sgRNA promoter 141, a first ribozyme 142, a targeting sequence 143, a scaffold 144 and a second ribozyme 145. The first gene editing fragment 110 and the second gene editing fragment 120 are constructed as a linear fragment 100 for gene editing of the chromosome of the *Candida viswanathii*. The first homology arm 111 and the second homology arm 121 respectively correspond to a specific fragment of a gene on the chromosome of the *Candida viswanathii*, and the targeting sequence 143 corresponds to a specific sequence of the gene on the chromosome of the *Candida viswanathii*.

Figure 2A:
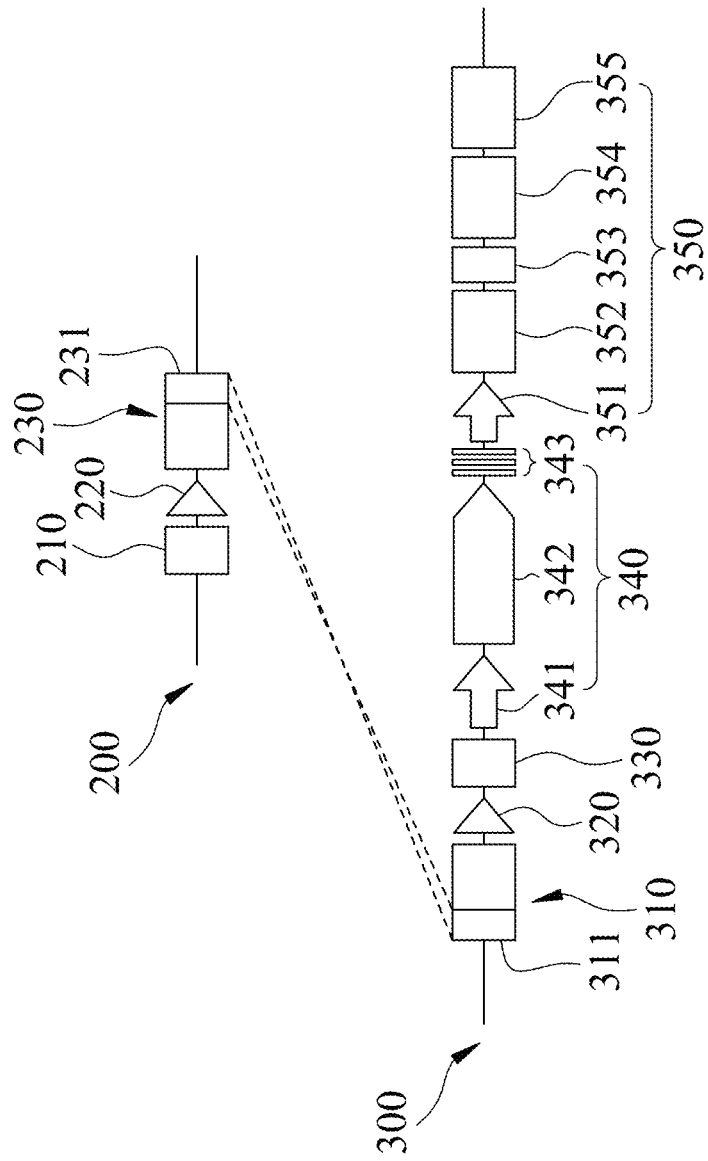
FIG. 2A is a schematic view showing a first gene editing fragment and a second gene editing fragment of a gene editing system of *Candida viswanathii* according to another embodiment of one aspect of the present disclosure.

Reference is made to FIG. 2A, which is a schematic view showing a first gene editing fragment 200 and a second gene editing fragment 300 of a gene editing system of *Candida viswanathii* according to another embodiment of one aspect of the present disclosure. The first gene editing fragment 200 successively includes a first homology arm 210 and a first screening gene fragment 230 of a screening gene (not numbered). The second gene editing fragment 300 successively includes a second screening gene fragment 310 of the screening gene, a second homology arm 330, a Cas9 expression cassette 340 and a sgRNA cassette 350. The Cas9 expression cassette 340 successively includes a Cas9 promoter 341, a Cas9 gene 342 and three nuclear localization sequences 343. The sgRNA cassette 350 successively includes a sgRNA promoter 351, a first ribozyme 352, a targeting sequence 353, a scaffold 354 and a second ribozyme 355. The first gene editing fragment 200 and the second gene editing fragment 300 are constructed as a linear fragment (not numbered) for gene editing of the chromosome of the *Candida viswanathii*. The first homology arm 210 and the second homology arm 330 respectively correspond to a specific fragment of a gene on the chromosome of the *Candida viswanathii*, and the targeting sequence 353 corresponds to a specific sequence of the gene on the chromosome of the *Candida viswanathii*.

Specifically, the screening gene (not numbered) of the first gene editing fragment 200 further includes the first screening gene fragment 230. The second gene editing fragment 300 further includes the second screening gene fragment 310 at an N-terminus of the second homology arm 330. The first screening gene fragment 230 has a homologous fragment 231, and the second screening gene fragment 310 has a homologous fragment 311. The first gene editing fragment 200 and the second gene editing fragment 300 are recombined into the linear fragment by the homologous fragment 231 and the homologous fragment 311.

In greater detail, the homologous fragment 231 and the homologous fragment 311 can be a homologous sequence with a size of about 400 bp, thereby improving the success rate and accuracy of recombination between the first gene editing fragment 200 and the second gene editing fragment 300, but the present disclosure is not limited thereto. The sgRNA promoter 351 and the Cas9 promoter 341 can be TDH1 promoter ($P_{TDH1}$), PGK1 promoter ($P_{PGK1}$), ACT1 promoter ($P_{ACT1}$) or ADH1 promoter ($P_{ADH1}$). Preferably, sgRNA promoter 351 can be $P_{TDH1}$, and the Cas9 promoter 341 can be $P_{PGK1}$, but the present disclosure is not limited thereto. The first ribozyme 352 can be Hammerhead (Ham) or tRNA$^{Ala}$ (derived from *Candida parapsilosis*). Preferably, the first ribozyme 352 can be tRNA$^{Ala}$, but the present disclosure is not limited thereto. The second ribozyme 355 can be selected from hepatitis delta virus (HDV) or tRNA$^{Gly}$ (derived from *Saccharomyces cerevisiae*). Preferably, the second ribozyme 355 can be HDV, but the disclosure is not limited thereto. The three nuclear localization sequences can be SV40 NLS (nuclear localization signal), but the disclosure is not limited thereto. The screening gene can be an antibiotic resistance gene, preferably, the screening gene can be a nourseothricin resistance (Nrs$^R$) gene, but the present disclosure is not limited thereto.

In addition, the Frt sequence 220 can be inserted upstream of the first screening gene fragment 230, and the Frt sequence 320 can be inserted downstream of the second screening gene fragment 310, so as to facilitate subsequent demarking engineering to delete the screening gene as required. Therefore, a gene editing technology of *Candida viswanathii* with high-efficiency that is not limited by the gene editing site and the size of the gene editing fragment can be achieved.

Figure 2B:
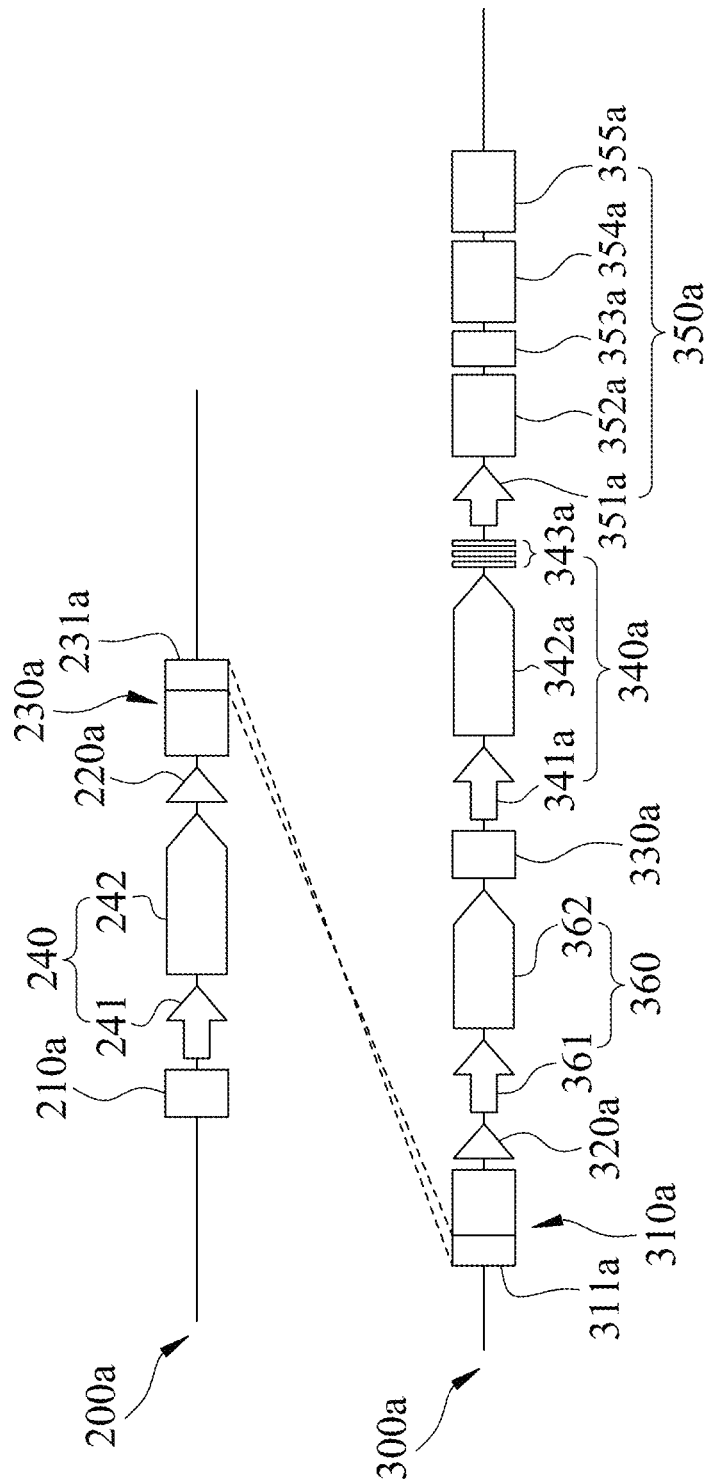
FIG. 2B is a schematic view showing a first gene editing fragment and a second gene editing fragment of a gene editing system of *Candida viswanathii* according to still another embodiment of one aspect of the present disclosure.

Reference is made to FIG. 2B, which is a schematic view showing a first gene editing fragment 200a and a second gene editing fragment 300a of a gene editing system of *Candida viswanathii* according to still another embodiment of one aspect of the present disclosure. In FIG. 2B, the first gene editing fragment 200a and the second gene editing fragment 300a are similar to the first gene editing fragment 200 and the second gene editing fragment 300. The difference is that the first gene editing fragment 200a includes at least one expression cassette 240, and the second gene editing fragment 300a includes at least one expression cassette 360. Other identical technical details will not be repeated here.

The first gene editing fragment 200a successively includes a first homology arm 210a, the at least one expression cassette 240 and a first screening gene fragment 230a of a screening gene (not numbered). The at least one expression cassette 240 includes an exogenous gene promoter 241 and an exogenous gene 242.

The second gene editing fragment 300a successively includes a second screening gene fragment 310a of the screening gene, the at least one expression cassette 360, a second homology arm 330a, a Cas9 expression cassette 340a and a sgRNA cassette 350a. The at least one expression cassette 360 includes an exogenous gene promoter 361 and an exogenous gene 362. The Cas9 expression cassette 340a successively includes a Cas9 promoter 341a, a Cas9 gene 342a and three nuclear localization sequences 343a. The sgRNA cassette 350a successively includes a sgRNA promoter 351a, a first ribozyme 352a, a targeting sequence 353a, a scaffold 354a and a second ribozyme 355a. The first gene editing fragment 200a and the second gene editing fragment 300a are constructed as a linear fragment (not numbered) for gene editing of the chromosome of the *Candida viswanathii*. The first homology arm 210a and the second homology arm 330a respectively correspond to a specific fragment of a gene on the chromosome of the *Candida viswanathii*, and the targeting sequence 353a corresponds to a specific sequence of the gene on the chromosome of the *Candida viswanathii*.

Specifically, the screening gene (not numbered) of the first gene editing fragment 200a further includes the first screening gene fragment 230a. The second gene editing fragment 300a further includes the second screening gene fragment 310a at an N-terminus of the second homology arm 330a. The first screening gene fragment 230a has a homologous fragment 231a, and the second screening gene fragment 310a has a homologous fragment 311a. The first gene editing fragment 200a and the second gene editing fragment 300a are recombined into the linear fragment by the homologous fragment 231a and the homologous fragment 311a.

Although the number of the at least one expression cassette in FIG. 2B is two, and they are respectively located in the first gene editing fragment 200a and the second gene editing fragment 300a. The number and location of the at least one expression cassette can be adjusted according to needs of editing, and the disclosure is not limited thereto.

In addition, a Frt sequence 220a can be inserted upstream of the first screening gene fragment 230a, and the a Frt sequence 320a can be inserted downstream of the second screening gene fragment 310a, so as to facilitate subsequent demarking engineering to delete the screening gene as required.

[Gene Editing Method of *Candida viswanathii*]

Figure 3:
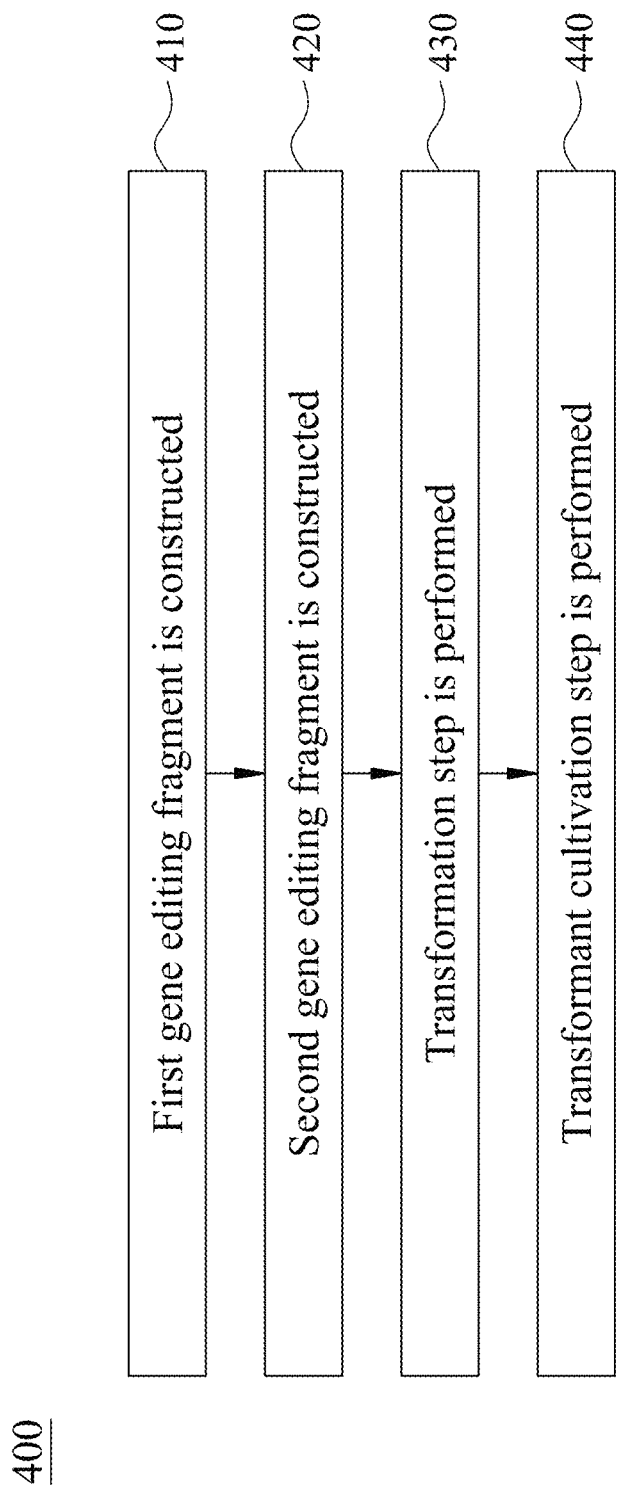
FIG. 3 is a flow diagram showing a gene editing method of *Candida viswanathii* according to another aspect of the present disclosure.

Reference is made to FIG. 3, which is a flow diagram showing a gene editing method of *Candida viswanathii* 400 according to another aspect of the present disclosure. The gene editing method of *Candida viswanathii* 400 includes Step 410, Step 420, Step 430 and Step 440.

In Step 410, a first gene editing fragment is constructed. The first gene editing fragment successively includes a first homology arm and a screening gene.

In Step 420, a second gene editing fragment is constructed. The second gene editing fragment is connected to the C-terminus of the first gene editing fragment, and successively includes a second homology arm, a Cas9 expression cassette and a sgRNA cassette. The Cas9 expression cassette successively includes a Cas9 promoter, a Cas9 gene and three nuclear localization sequences. The sgRNA cassette successively includes a sgRNA promoter, a first ribozyme, a targeting sequence, a scaffold and a second ribozyme. The first gene editing fragment and the second gene editing fragment are constructed as a linear fragment for gene editing of a chromosome of a *Candida viswanathii*. The first homology arm and the second homology arm respectively correspond to a specific fragment of a gene on the chromosome of the *Candida viswanathii*, and the targeting sequence corresponds to a specific sequence of the gene on the chromosome of the *Candida viswanathii*.

In greater detail, the first gene editing fragment and/or the second gene editing fragment can include at least one expression cassette, and the at least one expression cassette includes an exogenous gene promoter and an exogenous gene. In practical applications, the number and site of the at least one expression cassette can be adjusted according to editing needs. In addition, a Frt sequence can be inserted into the upstream of the first screening gene fragment and downstream of the second screening gene fragment, so as to facilitate subsequent demarking engineering to delete the screening gene as required.

In Step 430, a transformation step is performed. The first gene editing fragment and the second gene editing fragment are transformed into the *Candida viswanathii* to obtain a transformant.

In greater detail, when the first homology arm and the second homology arm perform homologous recombination on the specific fragment of *Candida viswanathii*, a fragment of about 1 kb can be deleted at the same time to improve the efficiency of complete insertion, but the disclosure is not limited thereto.

In Step 440, a transformant cultivation step is performed. The transformant is cultivated in a selection medium at an editing temperature for an editing time, the Cas9 expression cassette expresses the Cas9 gene, the sgRNA cassette expresses the targeting sequence, the first homology arm and the second homology arm are respectively homologously recombined with the specific fragment, and the first gene editing fragment and the second gene editing fragment located between the first homology arm and the second homology arm are integrated into the gene of the transformant.

Specifically, the screening gene of the first gene editing fragment can further include a first screening gene fragment, and the second gene editing fragment can further includes a second screening gene fragment at an N-terminus of the second homology arm. The first screening gene fragment has a homologous fragment, and the second screening gene fragment has a homologous fragment. The first gene editing fragment and the second gene editing fragment are recombined into the linear fragment by the homologous fragment of the first screening gene fragment and the homologous fragment of the second screening gene fragment. That is, the first gene editing fragment and the second gene editing fragment can be the same linear fragment and transformed into the cell of *Candida viswanathii* for gene editing, or can be recombined after co-transformation into the cell of *Candida viswanathii*, the timing of recombination can be adjusted according to editing needs, and the disclosure is not limited thereto. Therefore, a gene editing technology of *Candida viswanathii* with high-efficiency that is not limited by the gene editing site and the size of the gene editing fragment can be achieved.

[Transformant for Producing Dodecanedioic Acid]

A transformant for producing dodecanedioic acid of the present disclosure includes a host cell and at least two exogenous genes. The host cell is *Candida viswanathii*. The at least two exogenous genes includes CYP52A19 gene and CPRb gene, and the at least two exogenous genes are integrated into a chromosome of the host cell by the gene editing system of *Candida viswanathii* of the present disclosure. Specifically, the at least two exogenous genes are integrated into a chromosome of the host cell by the gene editing system of *Candida viswanathii* of the present disclosure shown in FIG. 2B.

In greater detail, the at least two exogenous genes can include CYP52A18 gene, FAO2 gene and POS5 gene. Therefore, productivity, purity and molar conversion of dodecanedioic acid can be improved. In addition, the at least two exogenous genes can be integrated into POX2 gene of the chromosome of the host cell.

[Method for Producing Dodecanedioic Acid]

Figure 4:
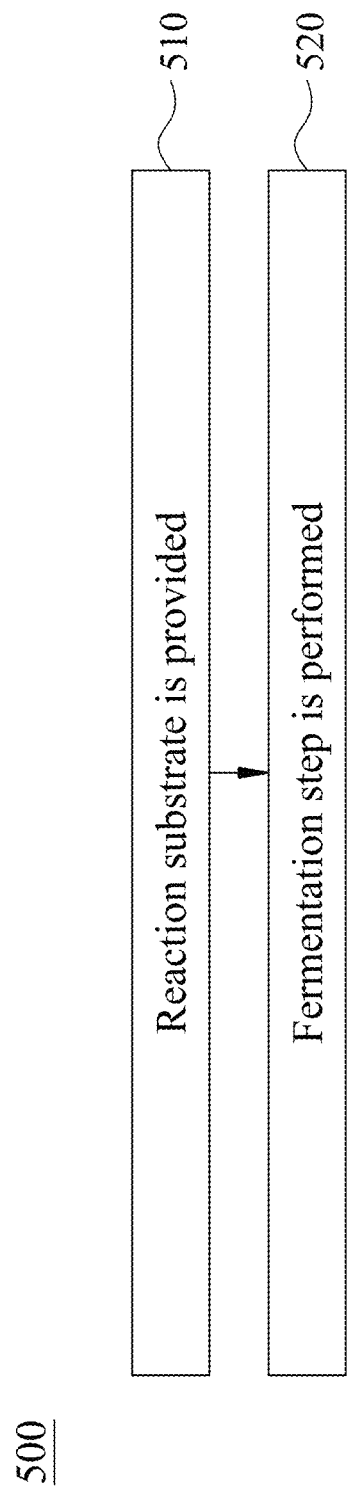
FIG. 4 is a flow diagram showing a method for producing dodecanedioic acid according to still another aspect of the present disclosure.

Reference is made to FIG. 4, which is a flow diagram showing a method for producing dodecanedioic acid 500 according to still another aspect of the present disclosure. In FIG. 4, the method for producing dodecanedioic acid 500 include Step 510 and Step 520.

In Step 510, a reaction substrate is provided. The reaction substrate includes dodecane.

In Step 520, a fermentation step is performed. The reaction substrate is inoculated with the transformant for producing dodecanedioic acid according to the aforementioned aspect, and then is cultured at a fermentation condition for a fermentation time to obtain a fermented substance, and the fermented substance includes dodecanedioic acid.

Reference will now be made in detail to the present embodiments of the present disclosure, examples of which are illustrated in the accompanying drawings.

Example

I. Assessing the Editing Capacity of the CRISPR-Cas9 System in *Candida viswanathii*

Figure 5A:
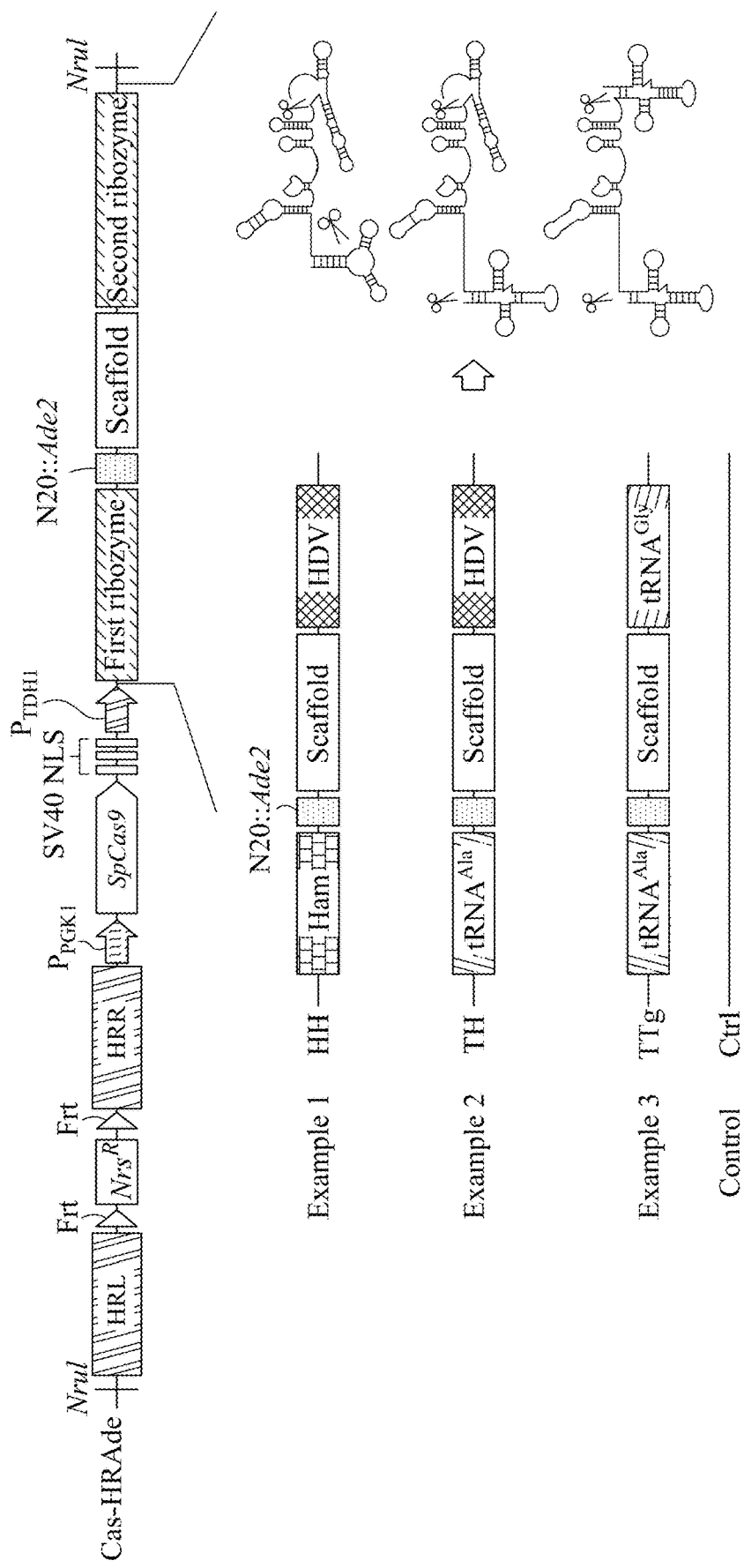
FIG. 5A is a schematic view showing constructions of sgRNA cassettes of Example 1 to Example 3 of the present disclosure for screening combinations of a first ribozyme and a second ribozyme.

Reference is made to FIG. 5A and FIG. 14A, FIG. 5A is a schematic view showing constructions of sgRNA cassettes of Example 1 to Example 3 of the present disclosure for screening combinations of a first ribozyme and a second ribozyme, and FIG. 14A shows Table 2 listing SEQ ID NOs and their corresponding genes referred in FIG. 5A. There is no report on the application of CRISPR-Cas9 system to *Candida viswanathii*, in order to confirm the ability of CRISPR-Cas9 system to integrate exogenous genes into the genome of *Candida viswanathii*, a linear fragment (represented as Cas-HRAde in FIG. 5A) is constructed experimentally for gene editing ability assessment of CRISPR-Cas9 system to *Candida viswanathii*. The Cas9 promoter is $P_{PGK1}$ with the sequence referenced as SEQ ID NO: 1 for driving the Cas9 gene (represented as SpCas9 in FIG. 5A) with the sequence referenced as SEQ ID NO: 2 in the Cas9 expression cassette and three nuclear localization sequences (represented as SV40 NLS in FIG. 5A) with the sequence referenced as SEQ ID NO: 3. The sgRNA promoter is $P_{TDH1}$ with the sequence referenced as SEQ ID NO: 4 for driving the sgRNA cassette, and Cas-HRAde includes a $Nrs^R$ gene with the sequence referenced as SEQ ID NO: 5 used as a screening gene, and the upstream and downstream of the $Nrs^R$ gene are respectively inserted a Frt sequence (represented as Frt in FIG. 5A) with the sequence referenced as SEQ ID NO: 6. The constructed Cas-HRAde is transformed into the cells of wild type *Candida viswanathii* ATCC 20962 (hereinafter referred as "*Candida viswanathii*") by electroporation. A first homology arm (represented as HRL in FIG. 5A) with the sequence referenced as SEQ ID NO: 7 and a second homology arm with the sequence referenced as SEQ ID NO: 8 (represented as HRR in FIG. 5A) are designed to correspond to a specific fragment of the Ade2 gene on the chromosome of *Candida viswanathii*, and a targeting sequence (represented as N20::Ade2 in FIG. 5A) can correspond to a specific sequence of the Ade2 gene on the chromosome of *Candida viswanathii*. The Ade2 gene is a reporter gene. When the $Nrs^R$ gene is integrated into the Ade2 gene on the chromosome of *Candida viswanathii*, the colony on the Yeast-Peptone-Dextrose (YPD) plate appears pink. The sgRNA is composed of the targeting sequence (N20::Ade2) and a scaffold with the sequence referenced as SEQ ID NO: 9, and the $P_{TDH1}$ driving the sgRNA cassette is a Pol II promoter, which requires in cis cleavage by the first ribozyme and the second ribozyme on the targeting sequence and the scaffold. Therefore, three different combinations of the first ribozyme expressed upstream of the targeting sequence and the second ribozyme expressed downstream of the scaffold including Hammerhead (Ham) of sequence referenced as SEQ ID NO: 10, hepatitis delta virus (HDV) of sequence referenced as SEQ ID NO: 11, tRNA$^{Ala}$ derived from *Candida parapsilosis* of sequence referenced as SEQ ID NO: 12 and tRNA$^{Gly}$ derived from *Saccharomyces cerevisiae* of the sequence referenced as SEQ ID NO: 13 are constructed experimentally as Examples, which are Ham-HDV (Example 1, HH), tRNA$^{Ala}$-HDV (Example 2, TH) and tRNA$^{Ala}$-tRNA$^{Gly}$ (Example 3, TTg) respectively. In addition, two sgRNAs, namely sgRNA1 and sgRNA2, are designed in the experiment for targeting different specific sequences on the Ade2 gene, wherein the targeting sequence of sgRNA1 is N20::Ade2-1 of sequence referenced as SEQ ID NO: 14, and the targeting sequence of sgRNA2 is N20::Ade2-2 of sequence referenced as SEQ ID NO: 15. A linear fragment (represented as Ctrl in FIG. 5A) that can only express the SpCas9 gene but has no targeting sequence, scaffold, first ribozyme and second ribozyme is used as a control.

Figure 5B:
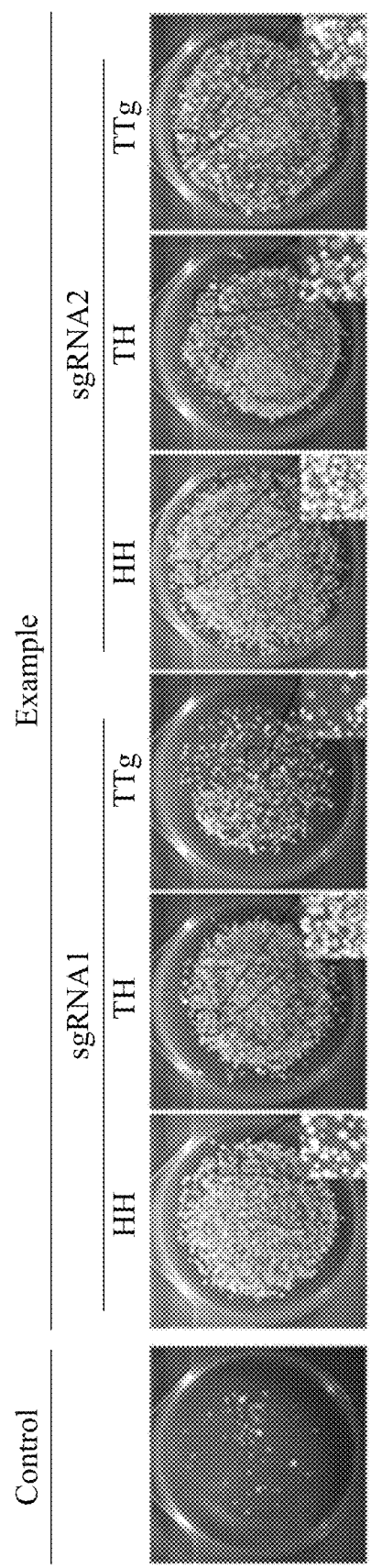
FIG. 5B shows analytical results of a colony formation of Example 1 to Example 3 of the present disclosure.
Figure 5C:
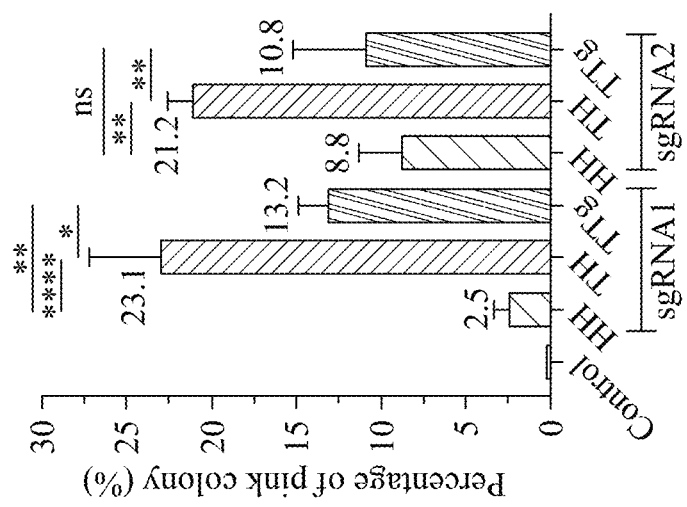
FIG. 5C is a quantitative diagram showing a colony phenotype ratio in FIG. 5B.

Reference is made to FIG. 5B and FIG. 5C. FIG. 5B shows analytical results of a colony formation of Example 1 to Example 3 of the present disclosure, and FIG. 5C is a quantitative diagram showing a colony phenotype ratio in FIG. 5B. Following nourseothricin (Nrs) selection, Example 1 (HH) to Example 3 (TTg) using sgRNA1 and sgRNA2 yield pink colonies, which indicate that the $Nrs^R$ gene can be successfully integrated into the Ade2 gene using the CRISPR-Cas9 system. Specifically, the percentage of pink colony of Example 1 (HH) is about 2.5-8.8%, and the percentage of pink colony of Example 3 (TTg) is about 10.8-13.2%. The percentage of pink colony of Example 2 (TH) is 21.2-23.1%, higher than that of Example 3 (TTg) and Example 1 (HH) at least one time, which indicates that flanking sgRNA with tRNA$^{Ala}$ and HDV as the first ribozyme and the second ribozyme respectively in Example 2 (TH) can more effectively process and cut the sgRNA in *Candida viswanathii*.

The aforementioned results indicates that the gene editing system of *Candida viswanathii* of the present disclosure and the use thereof verify that the CRISPR-Cas9 system can indeed edit the genes of *Candida viswanathii*, and can be modified by adjusting the first ribozyme and the second ribozyme combination to increase the success rate of gene editing.

II. Optimizing the Editing Capacity of the CRISPR-Cas9 System in *Candida viswanathii*

Although the CRISPR-Cas9 system has been proven experimentally to be effective in gene editing of *Candida viswanathii*, there are still some white colonies in the colonies in Example 2 (TH). Therefore, four primers (P1 of the sequence referenced as SEQ ID NO: 16, P2 of the sequence referenced as SEQ ID NO: 17, P3 of the sequence referenced as SEQ ID NO: 18 and P4 of the sequence referenced as SEQ ID NO: 19) are designed to detect the endogenous genome on the chromosome of *Candida viswa-*

*nathii*. 6 pink colonies and 2 white colonies are randomly selected, and colony PCR is used to confirm the edited genome of the colonies.

Figure 5D:
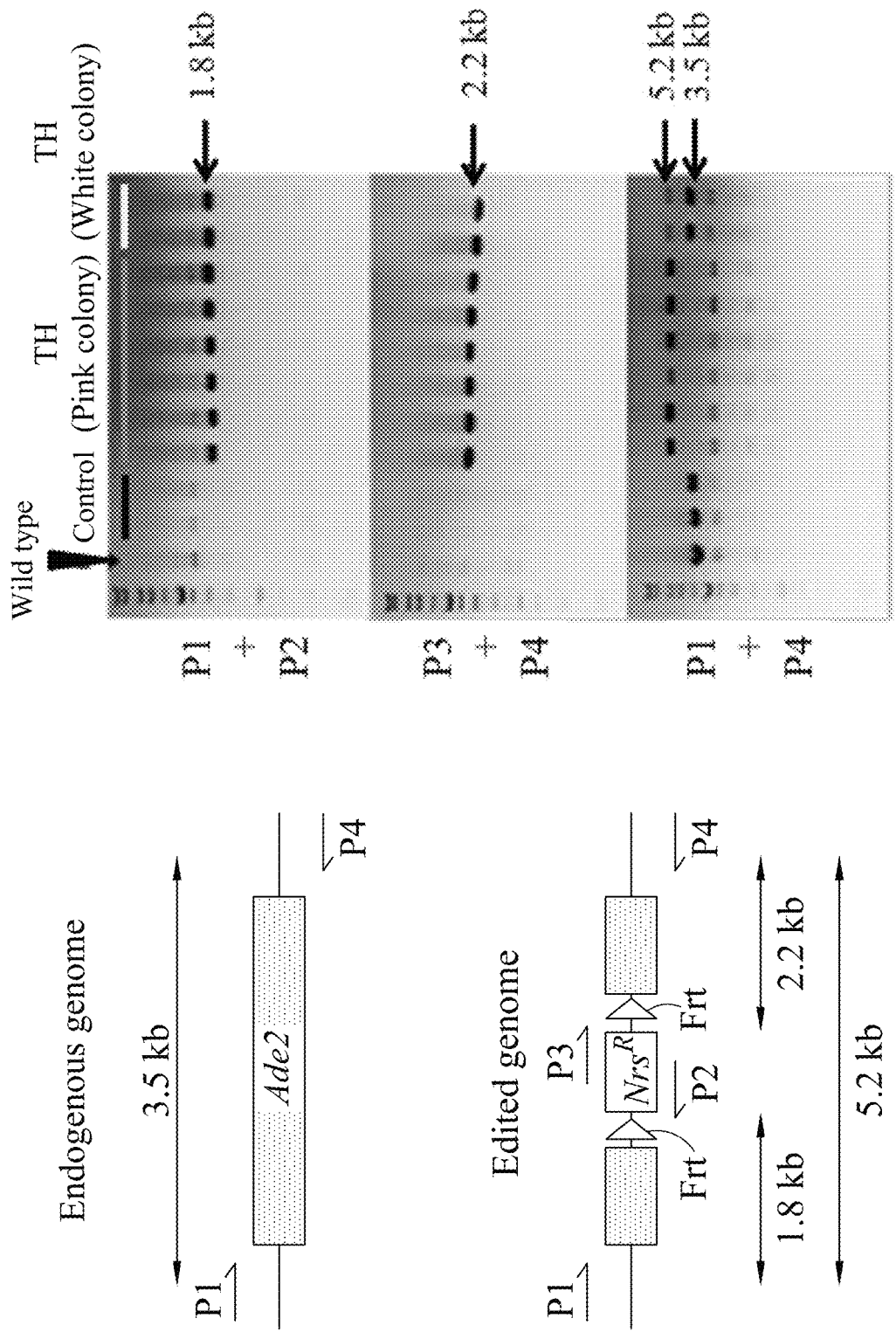
FIG. 5D shows analytical results of Example 2 of the present disclosure verified by colony PCR.
Figure 5E:
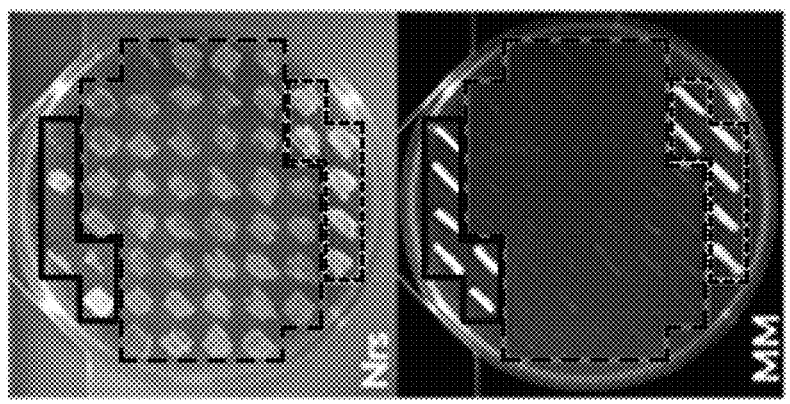
FIG. 5E shows analytical results of a colony formation of a nutrient deficiency test of Example 2 of the present disclosure.

Reference is made to FIG. 5D and FIG. 14A, FIG. 5D shows analytical results of Example 2 of the present disclosure verified by colony PCR, and FIG. 14A shows Table 2 listing SEQ ID NOs and their corresponding genes and primers referred in FIG. 5D. P1 and P4 are respectively designed on the upstream forward sequence and downstream reverse sequence of the Ade2 gene on the endogenous genome, and P2 and P3 are respectively designed on the front reverse sequence and terminal forward sequence of the Nrs$^R$ gene. For the endogenous genome of *Candida viswanathii* or Control, a PCR product with an expected size of about 3.5 kb can be obtained after PCR with primers P1+P4. For the edited genome successfully integrated the Nrs$^R$ gene into the Ade2 gene, a PCR product with an expected size of about 1.8 kb can be obtained after PCR with primers P1+P2, a PCR product with an expected size of about 2.2 kb can be obtained after PCR with primers P3+P4, and a PCR product with an expected size of about 5.2 kb can be obtained after PCR with primers P1+P4. In FIG. 5D, the PCR products of the pink colonies obtained through each set of primers are consistent with the expected size of the PCR products of the edited genome, indicating that the Nrs$^R$ gene has been successfully integrated into the Ade2 gene. The PCR products of the white colonies include the expected size of the PCR products of both the endogenous genome and the edited genome, indicating that the white colonies include not only the edited genome that successfully integrated the Nrs$^R$ gene into the Ade2 gene, but also the unedited endogenous genome. Reference is made to FIG. 5E, which shows analytical results of a colony formation of a nutrient deficiency test of Example 2 of the present disclosure. White colonies and pink colonies from Example 2 and Control are re-streaked onto the YPD plate containing Nrs (Nrs plate) and the mineral medium plate (MM plate) at the same time. The selected 40 pink colonies all grow well on the Nrs plate but not on the MM plate, while the white colonies from Example 2 grow well on the Nrs plate and the MM plate the same as Control. The results indicate that the pink colonies are homozygous edited transformants (Ade2$^{-/-}$) that have successfully integrated the Nrs$^R$ gene into the two copies of the Ade2 genes of *Candida viswanathii*, while the white colonies are heterozygous edited transformant (Ade2$^{+/-}$) that have failed to integrate the Nrs$^R$ gene into the two copies of the Ade2 genes of *Candida viswanathii*.

Figure 6B:
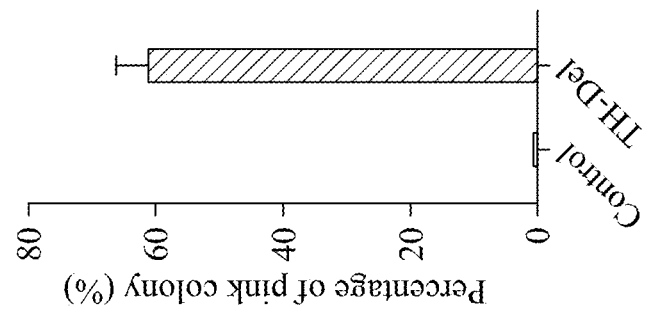
FIG. 6B is a quantitative diagram showing colony phenotype ratio in FIG. 6A.
Figure 6A:
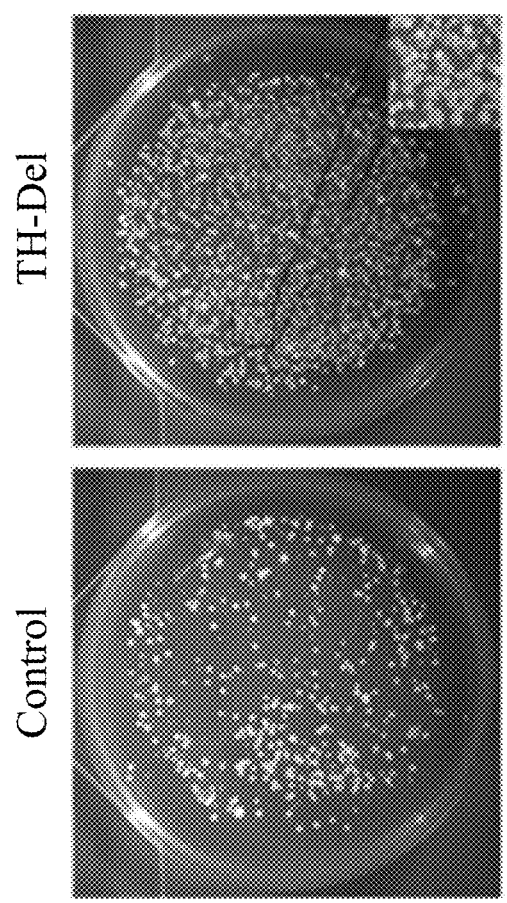
FIG. 6A shows analytical results of a colony formation for verifying the optimized homologous recombination strategy of the present disclosure.
Figure 6C:
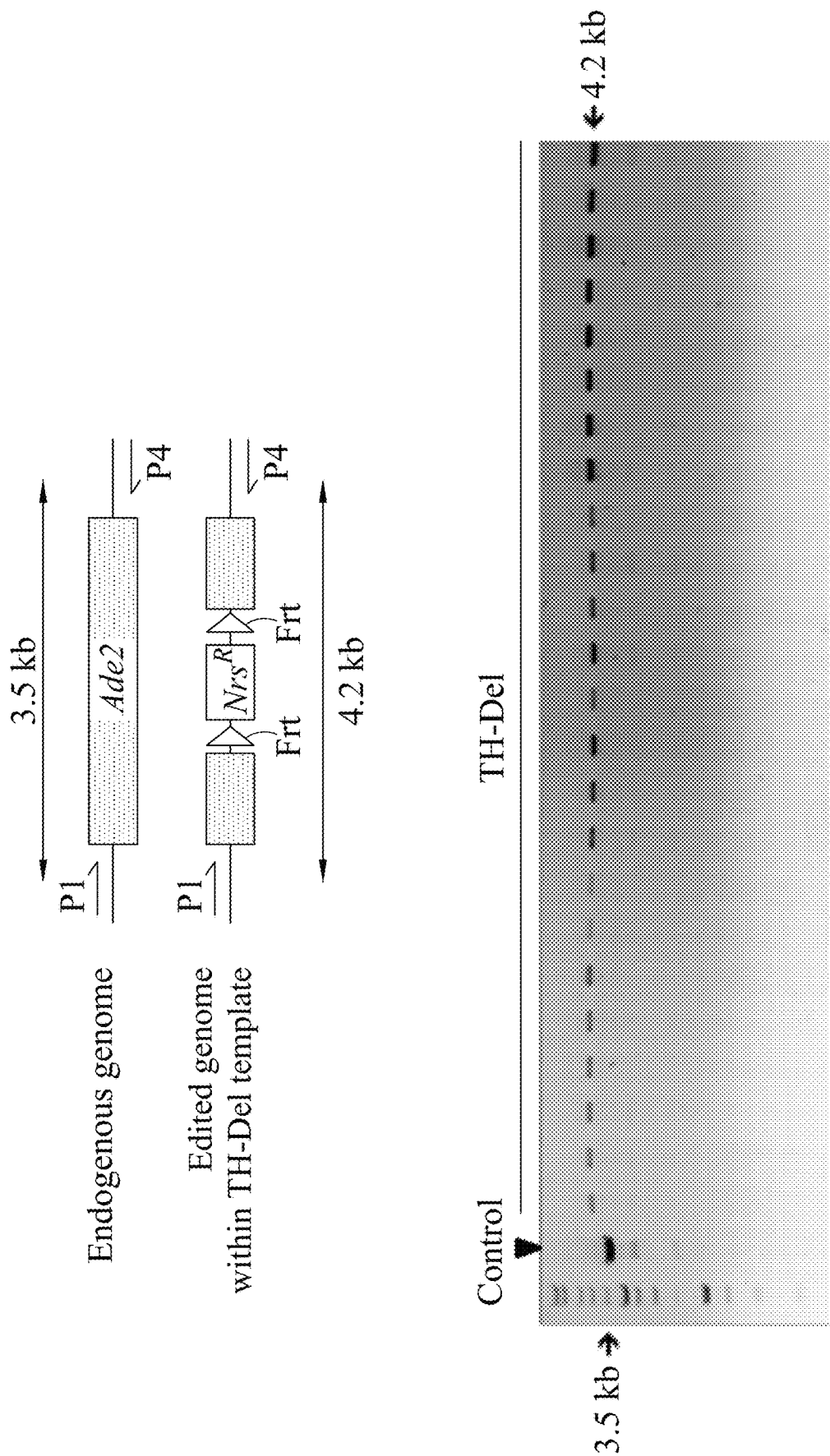
FIG. 6C shows analytical results of a colony formation of the optimized homologous recombination strategy of the present disclosure verified by colony PCR.

Reference is made to FIG. 6A to 6C and FIG. 14A. FIG. 6A shows analytical results of a colony formation for verifying the optimized homologous recombination strategy of the present disclosure, FIG. 6B is a quantitative diagram showing colony phenotype ratio in FIG. 6A, FIG. 6C shows analytical results of a colony formation of the optimized homologous recombination strategy of the present disclosure verified by colony PCR, and FIG. 14A shows Table 2 listing SEQ ID NOs and their corresponding genes and primers referred in FIG. 6C. To enhance homozygous integration frequency, a linear fragment (represented as TH-Del in FIG. 6A to FIG. 6C, and its structure diagram is not show) adjusting the site of the specific fragment on the Ade2 gene corresponding to the first homology arm and the second homology arm is constructed experimentally, and other structures of TH-Del is the same as that of Example 2 (TH). When the first homology arm and the second homology arm undergo homologous recombination with the Ade2 gene through the above-mentioned specific fragment, a fragment of about 1 kb will be deleted to increase the efficiency of integration. The electroporated *Candida viswanathii* is recovered in 2×YPD medium supplemented with essential amino acids and 40 mg/L adenine under a culture condition (30° C., 250 rpm) to slow down the growth stress and promote stress. After 4 hours recovery, additional 25 mg/L Nrs is added to induce gene editing, and the culture is continued for another 20 hours before streaking the cells onto YPD plates containing Nrs and adenine. The results show that through the above-mentioned optimization of the design of the first homology arm and the second homology arm and the electroporation recovery process, more than 60% of pink colonies Ade2$^{-/-}$ are produced on the Nrs plate, compared to Example 2 (TH) has a nearly three-fold increase in the percentage of pink colony. Furthermore, 24 randomly selected pink colonies edited by TH-Del are performed colony PCR, and all obtained PCR products of 4.2 kb, confirming that their genomes are all homozygous (Ade2$^{-/-}$). Although *Candida viswanathii* has polyploid chromosomes, the gene editing system of *Candida viswanathii* of the present disclosure can successfully integrate the exogenous gene into the target gene and permanently integrate the exogenous gene into the polyploid chromosomes of *Candida viswanathii*. Therefore, the results indicate that the gene editing system of *Candida viswanathii* of the present disclosure and uses thereof are highly efficient in completely editing of *Candida viswanathii*.

Figure 6D:
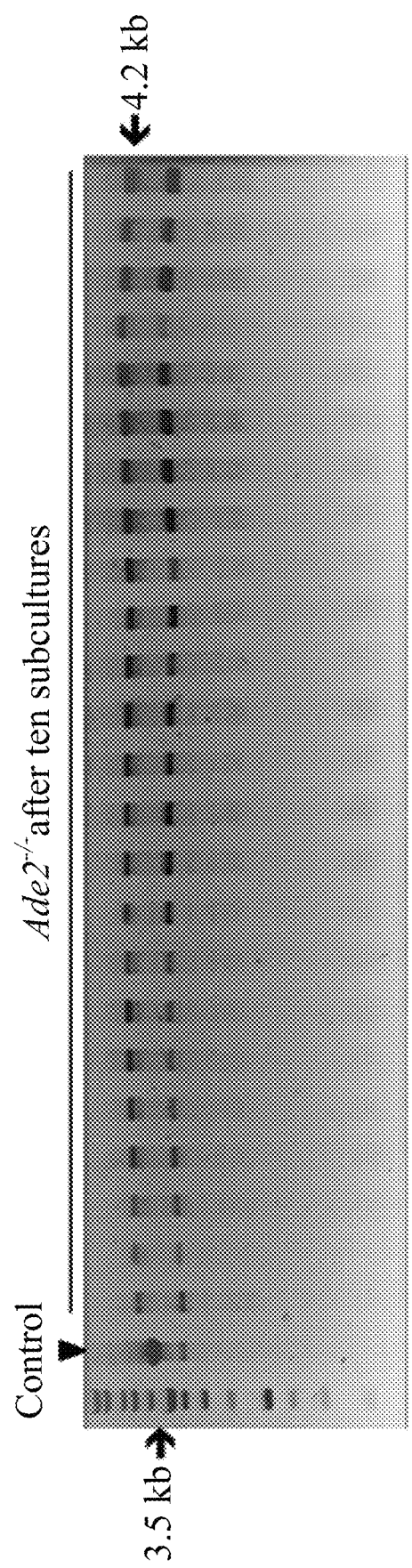
FIG. 6D shows analytical results of a stability of a transformant of the present disclosure verified by colony PCR.

Reference is made to FIG. 6D, which shows analytical results of a stability of a transformant of the present disclosure verified by colony PCR. After ten subcultures of the 24 pink colonies Ade2$^{-/-}$, each colony can still obtain a PCR product of 4.2 kb after colony PCR, which indicates that the gene editing of *Candida viswanathii* of the present disclosure and the transformant edited by the gene editing of *Candida viswanathii* of the present disclosure has extremely high genome stability.

Figure 7:
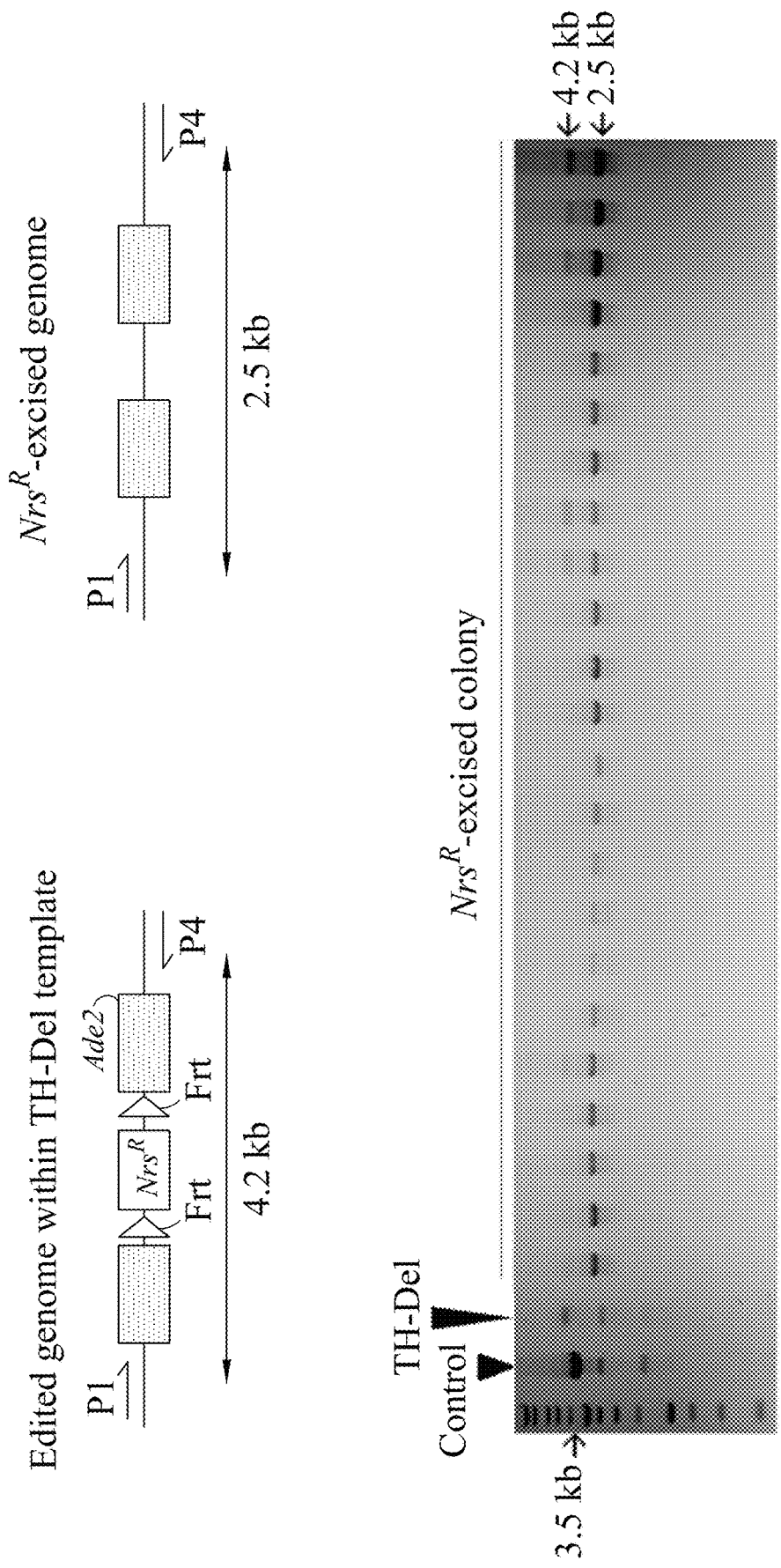
FIG. 7 shows analytical results of marker-free transformant of the present disclosure verified by colony PCR.

It is worth mentioning that, in order to reduce the cost and considerations required for practical application, such as adding antibiotics to maintain the stability of the strain, replacing the screening gene in response to research and development needs, etc., another plasmid pHyg-Flp (not shown) can be constructed. The plasmid pHyg-Flp includes the Hyg$^R$ gene of the sequence referenced as SEQ ID NO: 20 and the Flp gene of the sequence referenced as SEQ ID NO: 21, which can recognize and excise the Frt sequence on the DNA (represented as Frt in FIG. 6C and FIG. 7). Reference is made to FIG. 7 and FIG. 14A, FIG. 7 shows analytical results of marker-free transformant of the present disclosure verified by colony PCR, and FIG. 14A shows Table 2 listing SEQ ID NOs and their corresponding genes and primers referred in FIG. 7. The results show that after transforming the plasmid pHyg-Flp into Ade2$^{+/-}$ or Ade2$^{-/-}$ and then cultured, all randomly selected colonies obtained a 2.5 kb PCR product confirmed by colony PCR, indicating that the Nrs$^R$ gene in the genome had been successfully remove. The results indicate that the CRISPR-Cas9 system established by the gene editing system of *Candida viswanathii* of the present disclosure can successfully perform marker-free gene editing in *Candida viswanathii*.

The above results indicate that the gene editing system of *Candida viswanathii* of the present disclosure and uses thereof not only has the high efficiency of completely editing of *Candida viswanathii*, but also can use to edit the transformant having extremely high genome stability. Therefore, the gene editing system of *Candida viswanathii* of the present disclosure also can be used to construct marker-free transformant in response to the needs of practical applications.

III. Establishing of a Transformant for Producing Dodecanedioic Acid Stably and a Method for Producing Dodecanedioic Acid to Verify the Application Feasibility of the Gene Editing System of *Candida viswanathii*

3.1 Screening of Enzymes for Producing Dodecanedioic Acid

Figure 8:
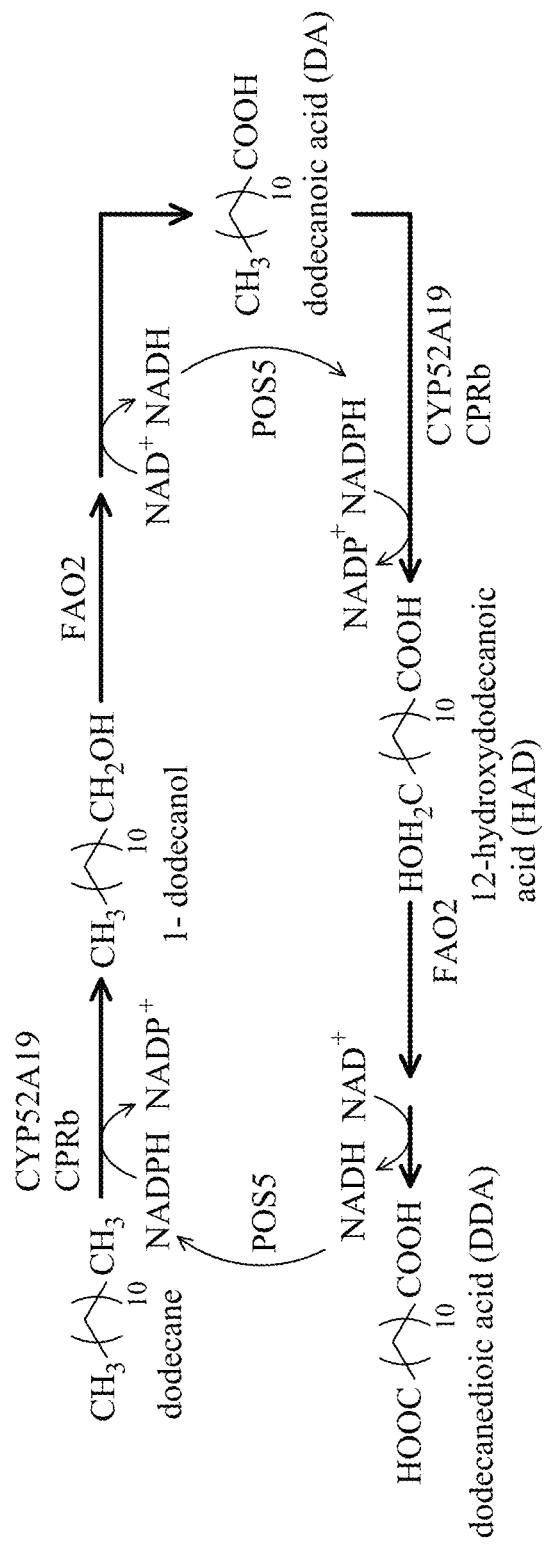
FIG. 8 is a schematic view showing pathway for dodecane conversion to dodecanedioic acid in *Candida viswanathii*.

Reference is made to FIG. 8, which is a schematic view showing pathway for dodecane conversion to dodecanedioic acid in *Candida viswanathii*. Cytochrome P450 monooxygenase (CYP) and nicotinamide adenine dinucleotide phosphate (NADPH) cytochrome reductase (CPR) are a family of enzymes that can catalyze the formation of dicarboxylic acids from various long-chain alkanes, such as CYP52A13, CYP52A15, CYP52A18, CYP52A19 and CPRb. Dodecane can be uptaken into the cell of *Candida viswanathii*, converted into 1-dodecanol, dodecanoic acid (DA), 12-hydroxydodecanoic acid (HDA) through a series of oxidation pathways, and finally converted to dodecanedioic acid (DDA) by CYP, CPR and other enzymes.

Figure 9A:
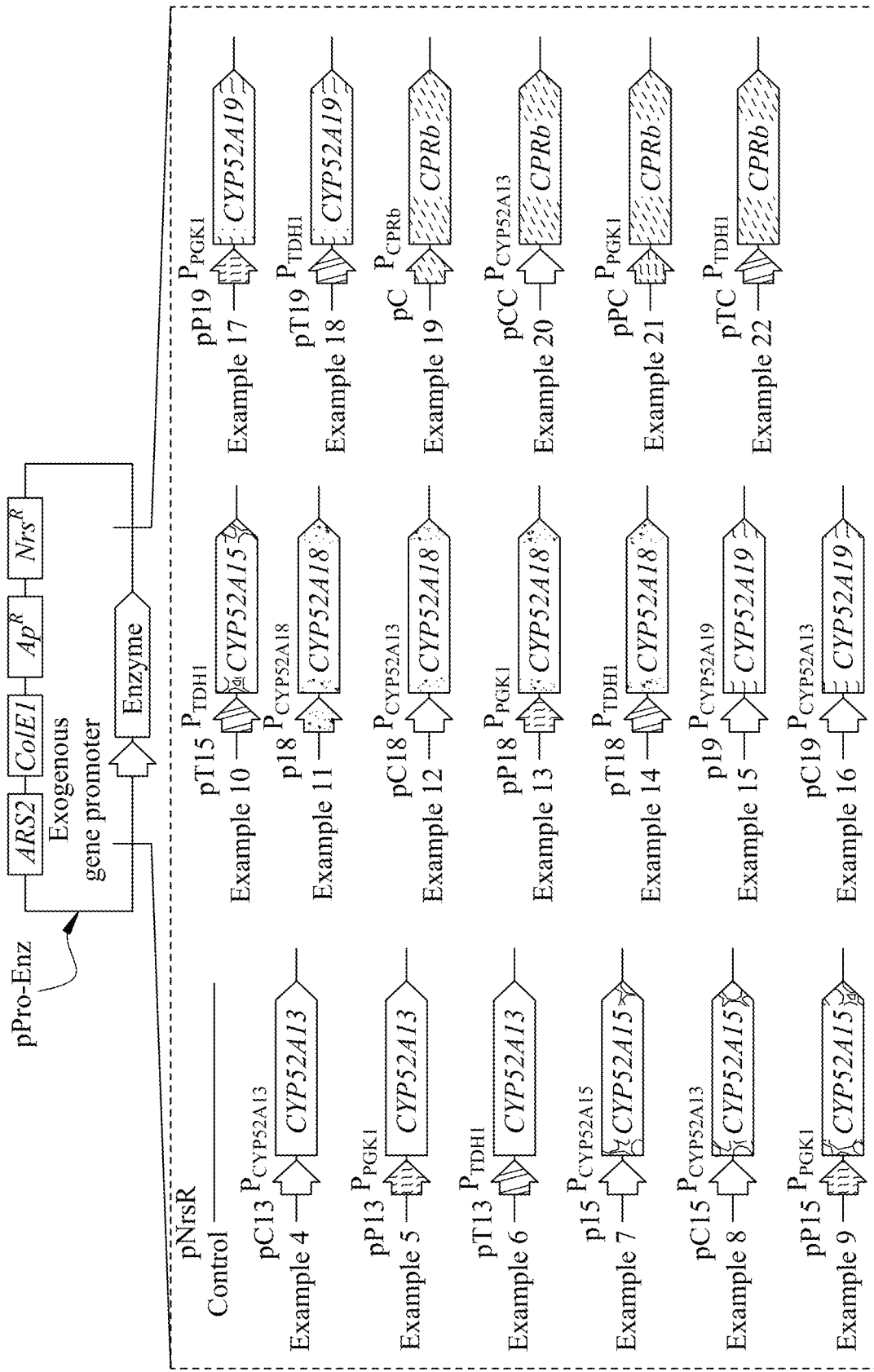
FIG. 9A is a schematic view showing constructions of expression cassettes of Example 4 to Example 22 of the present disclosure for screening enzymes producing dodecanedioic acid.

Reference is made to FIG. 9A and FIG. 14A. FIG. 9A is a schematic view showing constructions of expression cassettes of Example 4 (pC13), Example 5 (pP13), Example 6 (pT13), Example 7 (p15), Example 8 (pC15), Example 9 (pP15), Example 10 (pT15), Example 11 (p18), Example 12 (pC18), Example 13 (pP18), Example 14 (pT18), Example 15 (p19), Example 16 (pC19), Example 17 (pP19), Example 18 (pT19), Example 19 (pC), Example 20 (pCC), Example 21 (pPC) and Example 22 (pTC) of the present disclosure for screening enzymes producing dodecanedioic acid, wherein the dotted line shows the exogenous gene promoter and the exogenous gene of the enzyme producing dodecanedioic acid in the expression cassette of Example 4 to Example 22. FIG. 14A shows Table 2 listing SEQ ID NOs and their corresponding genes referred in FIG. 9A. In order to construct the transformant for producing dodecanedioic acid stably producing dodecanedioic acid, plasmids pPro-Enz including the Nrs$^R$ gene of Example 4 to Example 22 are experimentally constructed. The plasmid pPro-Enz includes the ARS2 gene of the sequence referenced as SEQ ID NO: 22, the ColE1 gene of the sequence referenced as SEQ ID NO: 23, the Ap$^R$ gene of the sequence referenced as SEQ ID NO: 24, the Nrs$^R$ gene and an expression cassette for screening the enzymes suitable for the conversion of dodecane to DDA in the metabolic pathway of *Candida viswanathii*. The expression cassette includes an exogenous gene promoter and the exogenous gene of the enzyme to be expressed. The enzyme encoded by the exogenous gene is selected from endogenous CYP or CPRb of *Candida viswanathii*, such as the CYP52A13 gene of the sequence referenced as SEQ ID NO: 25 (represented as CYP52A13 in FIG. 9A), the CYP52A15 gene of the sequence referenced as SEQ ID NO: 26 (represented as CYP52A15 in FIG. 9A), the CYP52A18 gene of the sequence referenced as SEQ ID NO: 27 (represented as CYP52A18 in FIG. 9A), the CYP52A19 gene of the sequence referenced as SEQ ID NO: 28 (represented as CYP52A19 in FIG. 9A) and the CPRb gene of the sequence referenced as SEQ ID NO: 29 (represented as CPRb in FIG. 9A). The exogenous gene promoter is selected from the endogenous promoter of the above-mentioned endogenous CYP/CPRb (such as $P_{CYP52A15}$ of sequence referenced as SEQ ID NO: 30, $P_{CYP52A18}$ of sequence referenced as SEQ ID NO: 31, $P_{CYP52A19}$ of the sequence referenced as SEQ ID NO: 32 and $P_{CPRb}$ of the sequence referenced as SEQ ID NO: 33), dodecane-inducible promoter (PCYP52A13 of the sequence referenced as SEQ ID NO: 34) or $P_{TDH1}$ and $P_{PGK1}$. In addition, a pNrsR that does not express the expression cassette is used as Control. After electroporating the plasmids pPro-Enz of Example 4 to Example 22 into *Candida viswanathii* respectively, *Candida viswanathii* containing Example 4 to Example 22 are cultured in shake flasks to produce DDA, and then the titer of DDA in the culture supernatants is analyzed by gas chromatography-flame ionization detector (GC-FID).

Figure 9B:
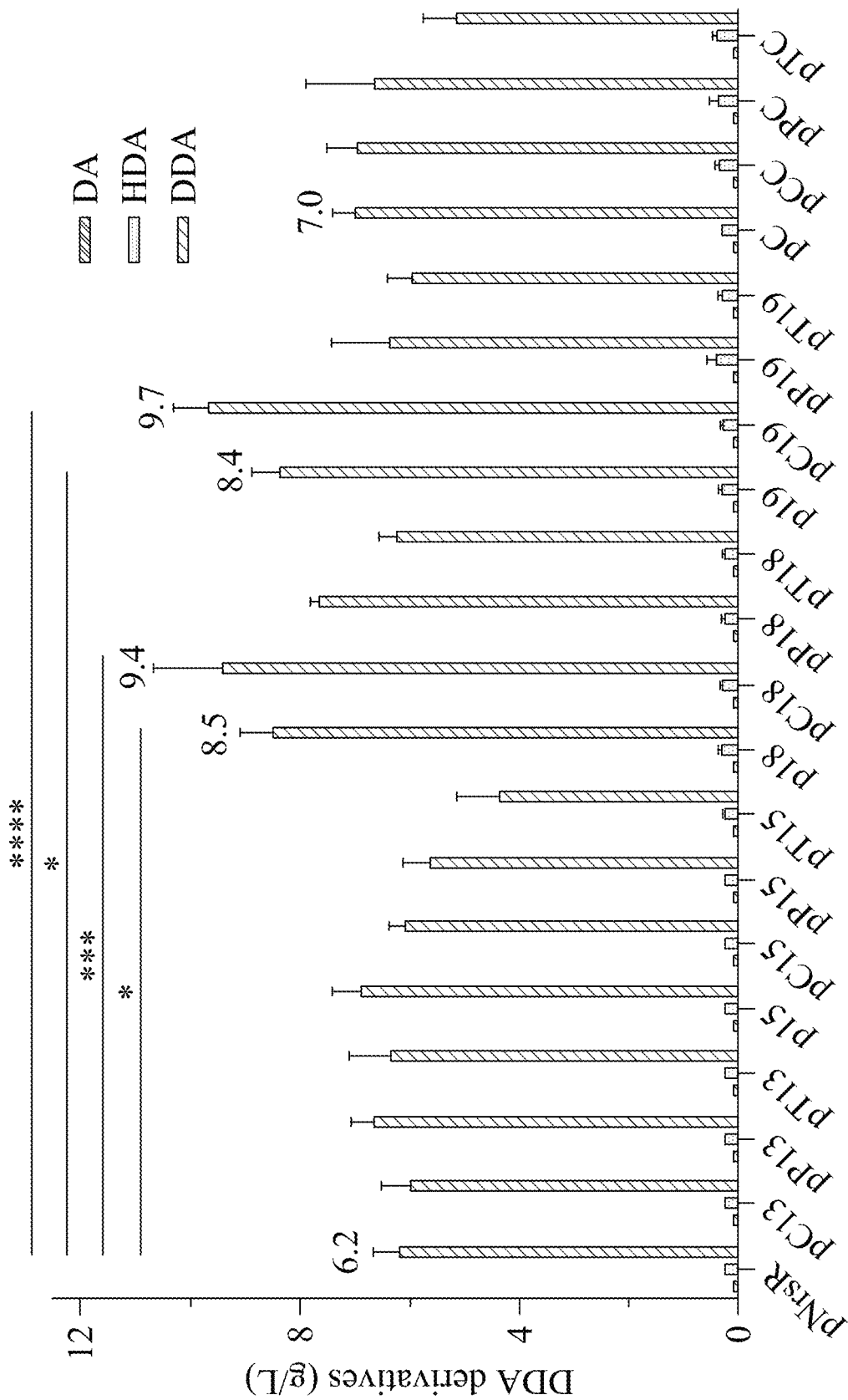
FIG. 9B shows analytical results of titer of dodecanedioic acid from culture supernatants of Example 4 to Example 22 of the present disclosure cultured in shake flasks.

Reference is made to FIG. 9B, which shows analytical results of titer of dodecanedioic acid from culture supernatants of Example 4 to Example 22 of the present disclosure cultured in shake flasks. Examples 4 to 22 can produce DDA and only accompanied by a very small amount of by-products HDA and DA. Specifically, the titers of DDA in Example 4 (pC13), Example 5 (pP13), Example 6 (pT13), Example 7 (p15), Example 8 (pC15), Example 9 (pP15) and Example 10 (pT15) expressing the CYP52A13 gene and the CYP52A15 gene are only equivalent to or even lower than that of Control. The titers of DDA in Example 19 (pC), Example 20 (pCC), Example 21 (pPC) and Example 22 (pTC) expressing the CPRb gene, and Example 19 (pC) only using $P_{CPRb}$ are slightly higher than that of Control. In contrast, the titers of DDA of Example 11 (p18), Example 12 (pC18), Example 15 (p19) and Example 16 (pC19) are all significantly improved compared to that of Control.

The results indicate that the gene editing system of *Candida viswanathii* of the present disclosure and uses thereof can effectively increase the titer of DDA by using the endogenous promoter or $P_{CYP52A13}$ to drive the expression of the CYP52A18 gene, the CYP52A19 gene or the CPRb gene.

Figure 10A:
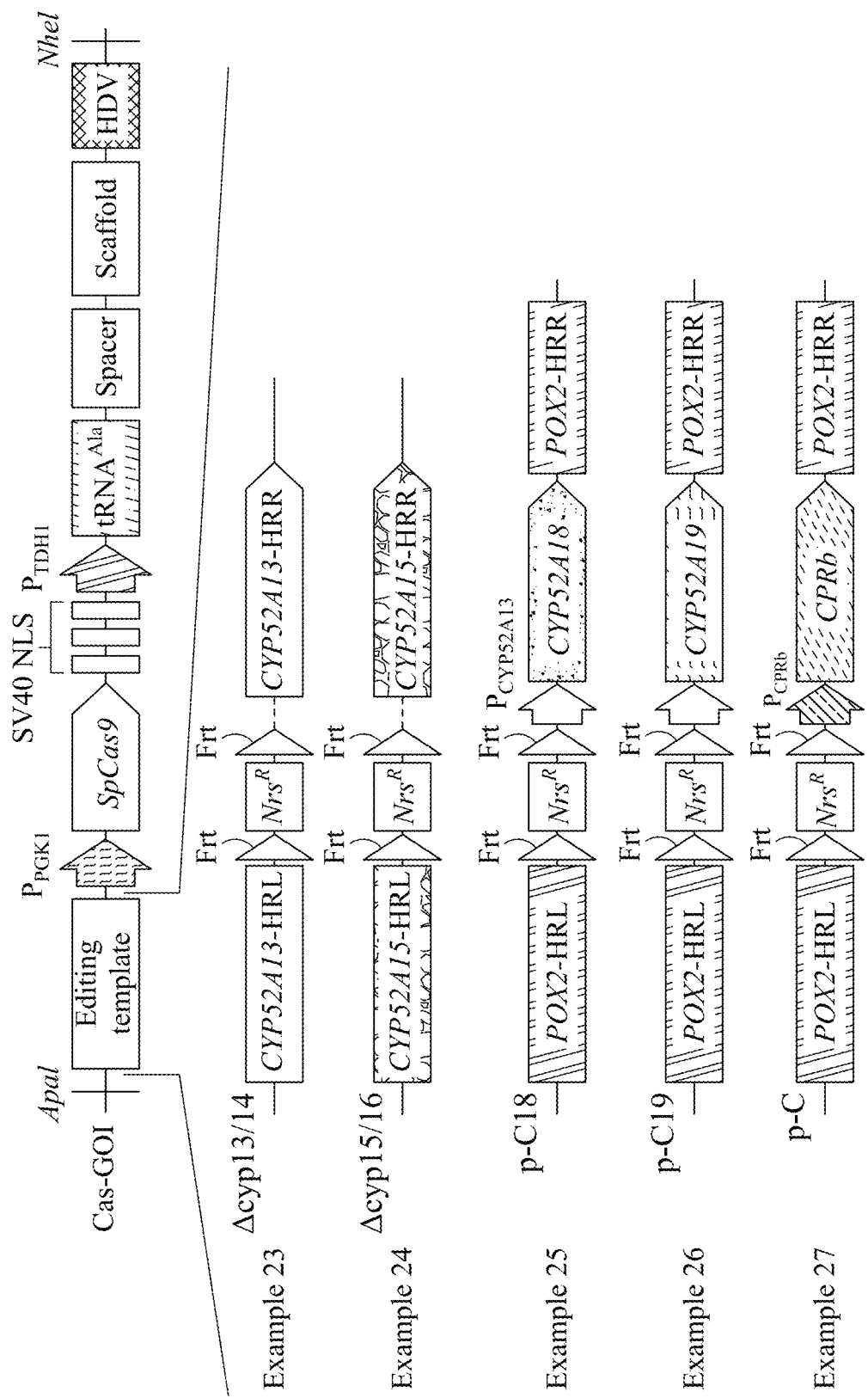
FIG. 10A is a schematic view showing constructions of Example 23 to Example 27 of the present disclosure for screening integrated site.
Figure 10B:
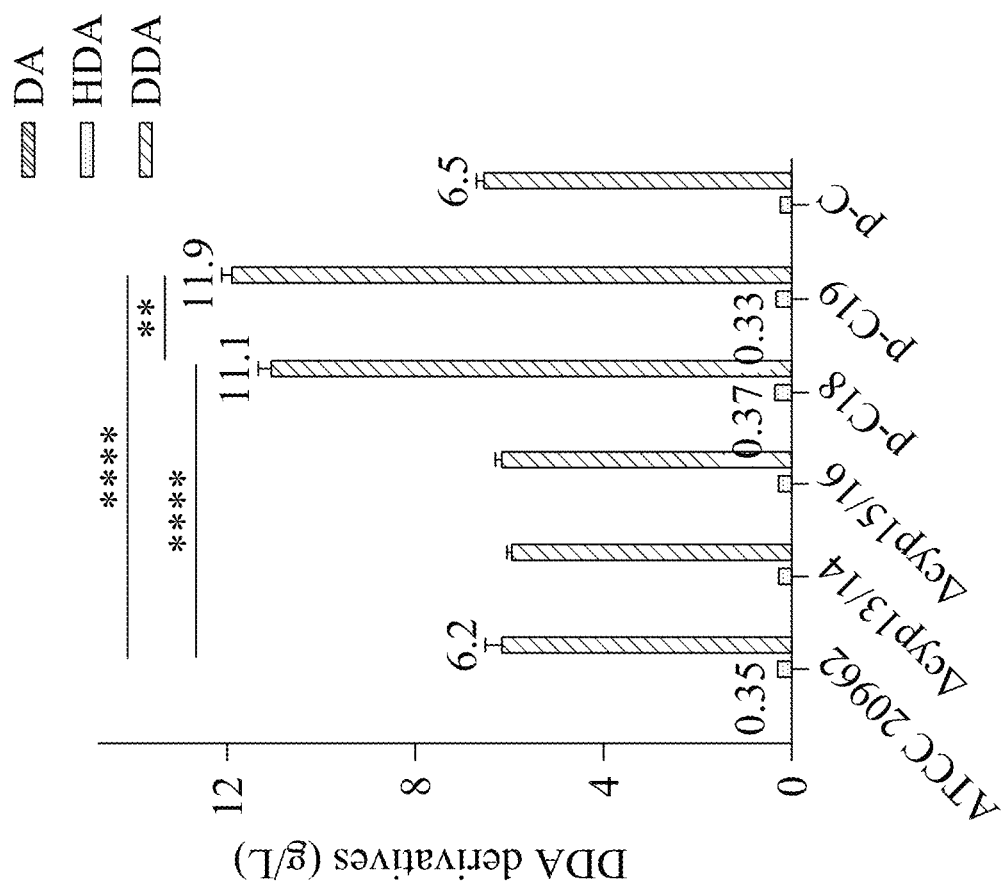
FIG. 10B shows analytical results of titer of dodecanedioic acid from culture supernatants of Example 23 to Example 27 of the present disclosure cultured in shake flasks.

Reference is made to FIG. 10A, FIG. 10B and FIG. 14B. FIG. 10A is a schematic view showing constructions of Example 23 (Δcyp13/14), Example 24 (Δcyp15/16), Example 25 (p-C18), Example 26 (p-C19) and Example 27 (p-C) of the present disclosure for screening integrated site. FIG. 10B shows analytical results of titer of dodecanedioic acid from culture supernatants of Example 23 to Example 27 of the present disclosure cultured in shake flasks. FIG. 14B shows Table 3 listing SEQ ID NOs and their corresponding genes referred in FIG. 10A. In order to further improve the titer of DDA, a linear fragment (represented as Cas-GOI in FIG. 10A) including an editing template is experimentally constructed. Examples 23 to 27 are constructed based on Cas-GOI. The difference between Example 23 to Example 27 are the construction of the first homology arm, the second homology arm and the expression cassette represented by the editing template, wherein the first homology arm and the second homology arm correspond to different specific fragments of different genes on the chromosome of *Candida viswanathii* for deletion at the enzyme (CYP52A13/14 or CYP52A15/16) that may compete with the conversion of dodecane to DDA in *Candida viswanathii*. For example, the first homology arm of the sequence referenced as SEQ ID NO: 35 in Example 23 (Δcyp13/14) (represented as CYP52A13-HRL in FIG. 10A) and the second homology arm of the sequence referenced as SEQ ID NO: 36 (represented as CYP52A13-HRR in FIG. 10A), and the first homology arm of the sequence referenced as SEQ ID NO: 37 (represented as CYP52A15-HRL in FIG. 10A) and the second homology arm of the sequence referenced as SEQ ID NO: 38 (represented as CYP52A15-HRR in FIG. 10A) in Example 24 (Δcyp15/16). Alternatively, the expression cassette for the conversion of dodecane to DDA can be integrated together with deletion of the enzyme (POX2) of the competing pathway. For example, the first homology arm of the sequence referenced as SEQ ID NO: 39 (represented as POX2-HRL in FIG. 10A) and the second homology arm of the sequence referenced as SEQ ID NO: 40 (represented by POX2-HRR in FIG. 10A) in Example 25 (p-C18), Example 26 (p-C19) and Example 27 (p-C). The spacer of Cas-GOI is the position of the targeting sequence corresponding to the target of the gene to be integrated in each Example. For example, N20::CYP52A13/14 of the sequence referenced as SEQ ID NO: 41 used in Example 23, N20::CYP52A15/16 of the sequence referenced as SEQ ID NO: 42 used in Example 24, N20::POX2 of the sequence referenced as SEQ ID NO: 43 in Example 25 and Example 26. After electroporating Cas-GOI of Example 23 to Example 27 into *Candida viswanathii* respectively, *Candida viswanathii* containing Example 23 to Example 27 are cultured in shake flasks to produce DDA respectively, and then the titer of DDA in the culture supernatants is analyzed by GC-FID. After 24 hours of shake flask culture, the titers of DDA of Example 23 (Δcyp13/14), Example 24 (Δcyp15/16) and Example 27 (p-C) are all comparable to DDA produced by *Candida viswanathii* (Control), while titers of DDA of Example 25 (p-C18) and Example 26 (p-C19) are 90% higher than that of Control.

The results indicate again that the gene editing system of *Candida viswanathii* of the present disclosure and uses thereof can significantly improve increase the production of DDA by using $P_{CYP52A13}$ to drive the expression of the CYP52A18 gene or the CYP52A19 gene and simultaneously blocking the enzyme (the POX2 gene) in the ω-hydroxylation pathway.

Figure 10C:
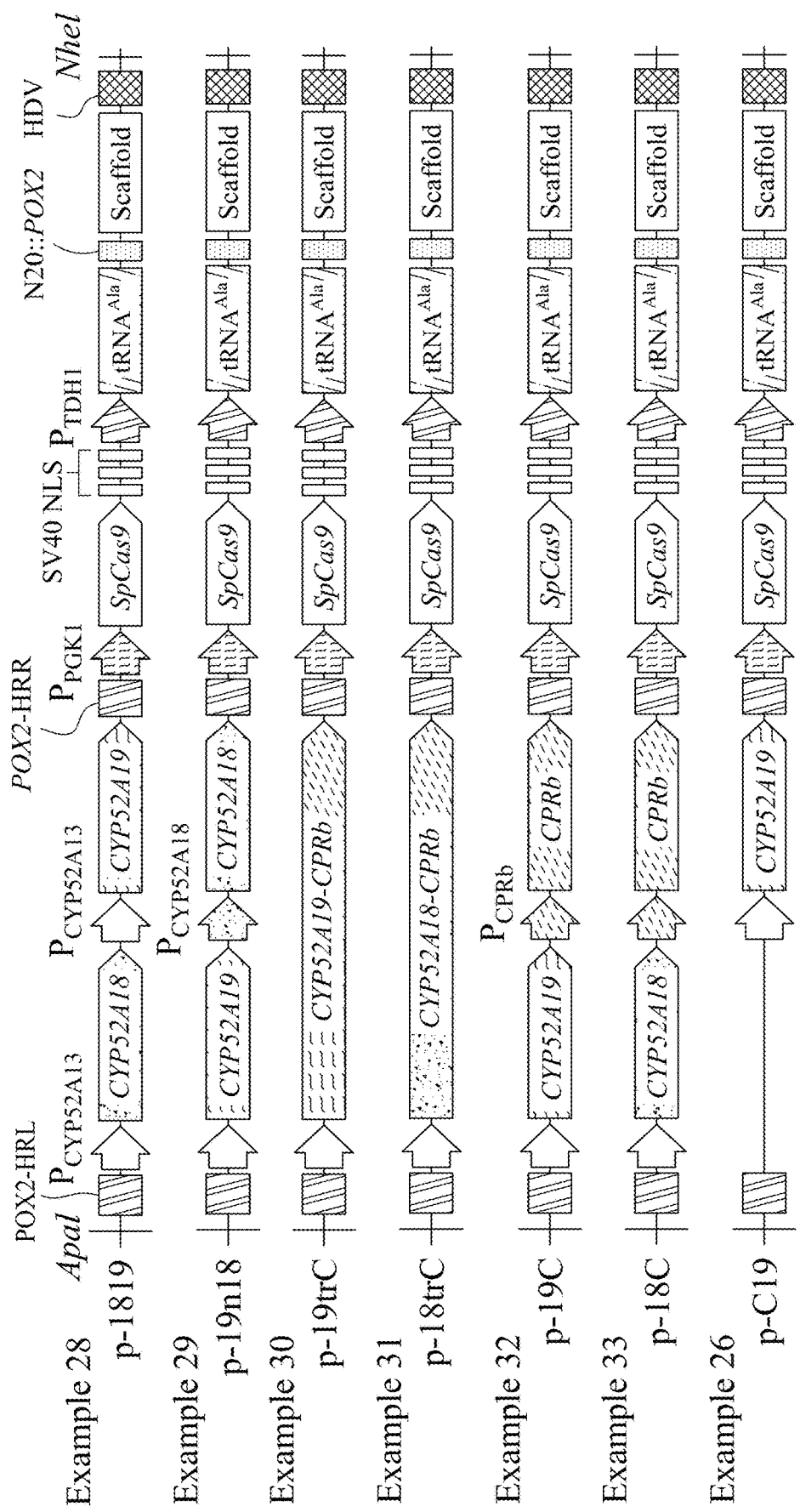
FIG. 10C is a schematic view showing constructions of expression cassettes of Example 26 and Example 28 to Example 33 of the present disclosure for screening and optimizing enzymes for producing dodecanedioic acid.
Figure 10D:
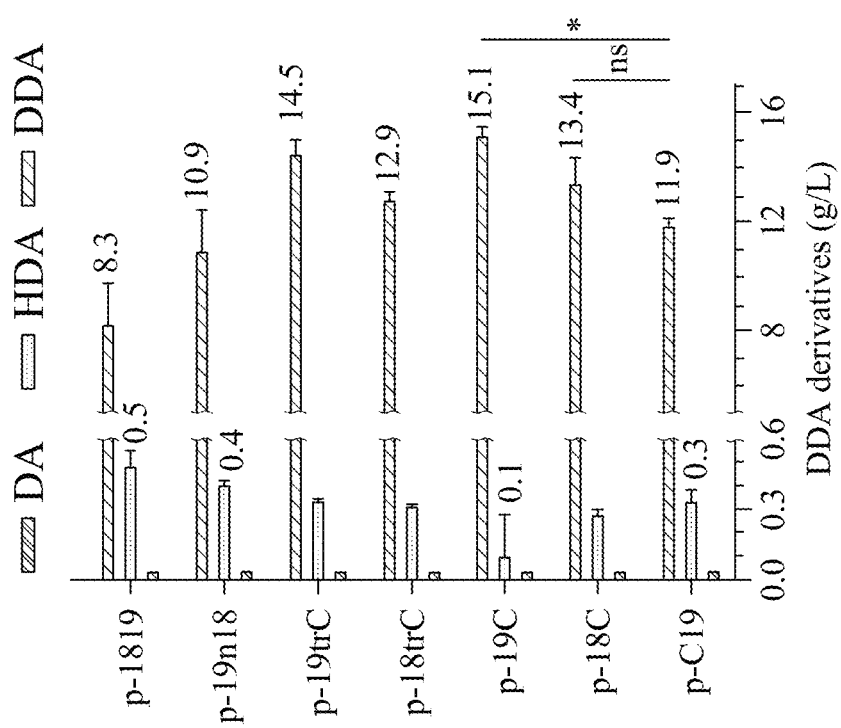
FIG. 10D shows analytical results of titer of dodecanedioic acid from culture supernatants of Example 26 and Example 28 to Example 33 of the present disclosure cultured in shake flasks.

Reference is made to FIG. 10C, FIG. 10D and FIG. 14B. FIG. 10C is a schematic view showing constructions of expression cassettes of Example 26 (p-C19), Example 28 (p-1819), Example 29 (p-19n18), Example 30 (p-19trC), Example 31 (p-18trC), Example 32 (p-19C) and Example 33 (p-18C) of the present disclosure for screening and optimizing enzymes for producing dodecanedioic acid. FIG. 10D shows analytical results of titer of dodecanedioic acid from culture supernatants of Example 26 and Example 28 to Example 33 of the present disclosure cultured in shake flasks. FIG. 14B shows Table 3 listing SEQ ID NOs and their corresponding genes referred in FIG. 10C. The results in the previous paragraph show that the selection of the exogenous gene promoter in the expression cassette and the selection of CYP or CPRb encoded by the exogenous gene significantly affect the titer of DDA. In order to further enhance the ability of the transformant to produce DDA, Example 28 to Example 33 are constructed. Example 26 and Example 28 to Example 33 are used to test DDA production performances together, so as to obtain a performance of the expression cassette for converting dodecane into DDA. Example 28 (p-1819), Example 29 (p-19n18), Example 32 (p-19C) and Example 33 (p-18C) express the CYP52A18 gene (represented as CYP52A18 in FIG. 10C), the CYP52A19 gene (represented as CYP52A19 in FIG. 10C) or the CPRb gene (represented as CPRb in FIG. 10C) individually with two expression cassettes. Example 30 (p-19trC) and Example 31 (p-18trC) expresses the CYP52A18-CPRb genes with the sequence referenced as SEQ ID NO: 44 with a single expression cassette (represented as CYP52A18-CPRb in FIG. 10C) or the CYP52A19-CPRb gene with the sequence referenced as SEQ ID NO: 45 (represented as CYP52A19-CPRb in FIG. 10C). The results in FIG. 10D show that Example 28 (p-1819) and Example 29 (p-19n18) co-expressing the CYP52A18 gene and the CYP52A19 gene respectively give lower titer of DDA (8.3-10.9 g/L) than Example 26 (p-C19) expressing the CYP52A19 gene alone under $P_{CYP52A13}$ (11.9 g/L). Conversely, the titers of DDA (12.9-15.1 g/L) of Example 32 (p-19C) and Example 33 (p-18C) co-expressing the CYP52A18 gene (or the CYP52A19 gene) and the CPRb gene respectively and Example 30 (p-19trC) and Example 31 (p-18trC) fusion co-expressing the CYP52A18-CPRb gene or the CYP52A19-CPRb gene are all greater than that of Example 26 (p-C19). Among these transformants, P-19C strain that transformed Example 32 (p-19C) can yield the highest DDA (15.1 g/L) within 24 hours.

Figure 10E:
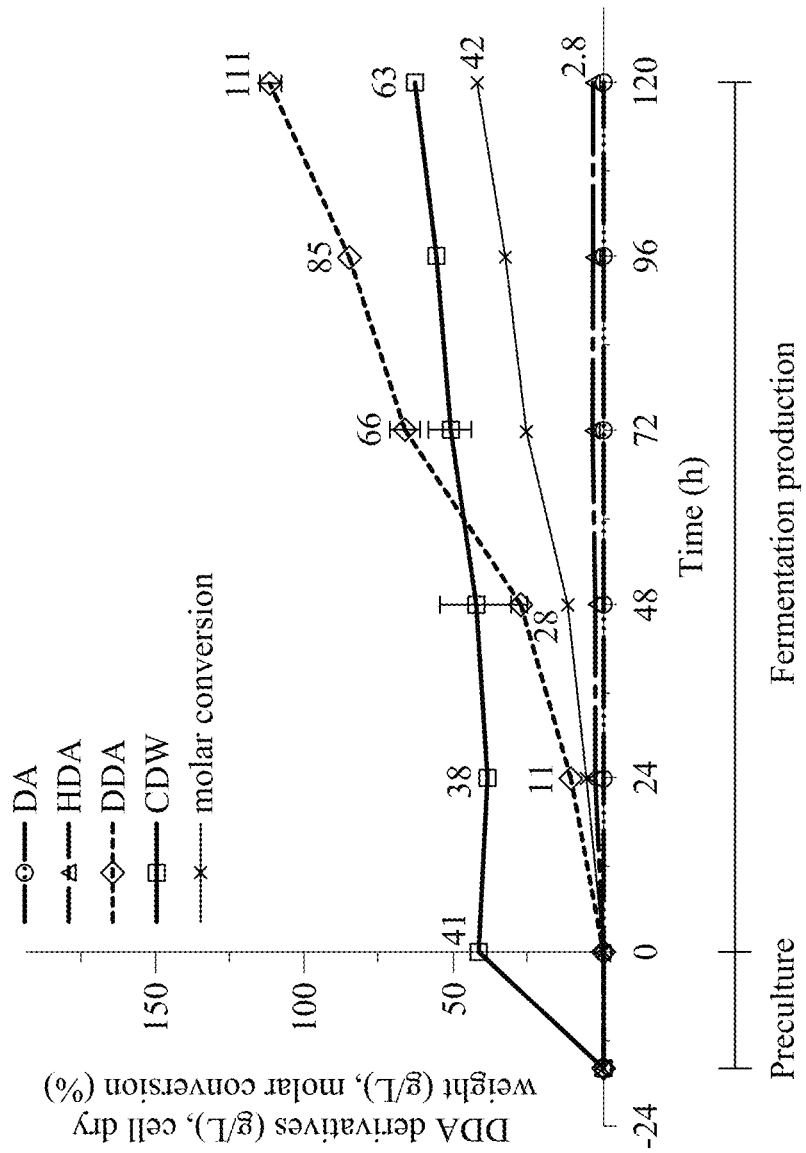
FIG. 10E shows analytical results of titer of dodecanedioic acid by fermentation production of *Candida viswanathii*.
Figure 10F:
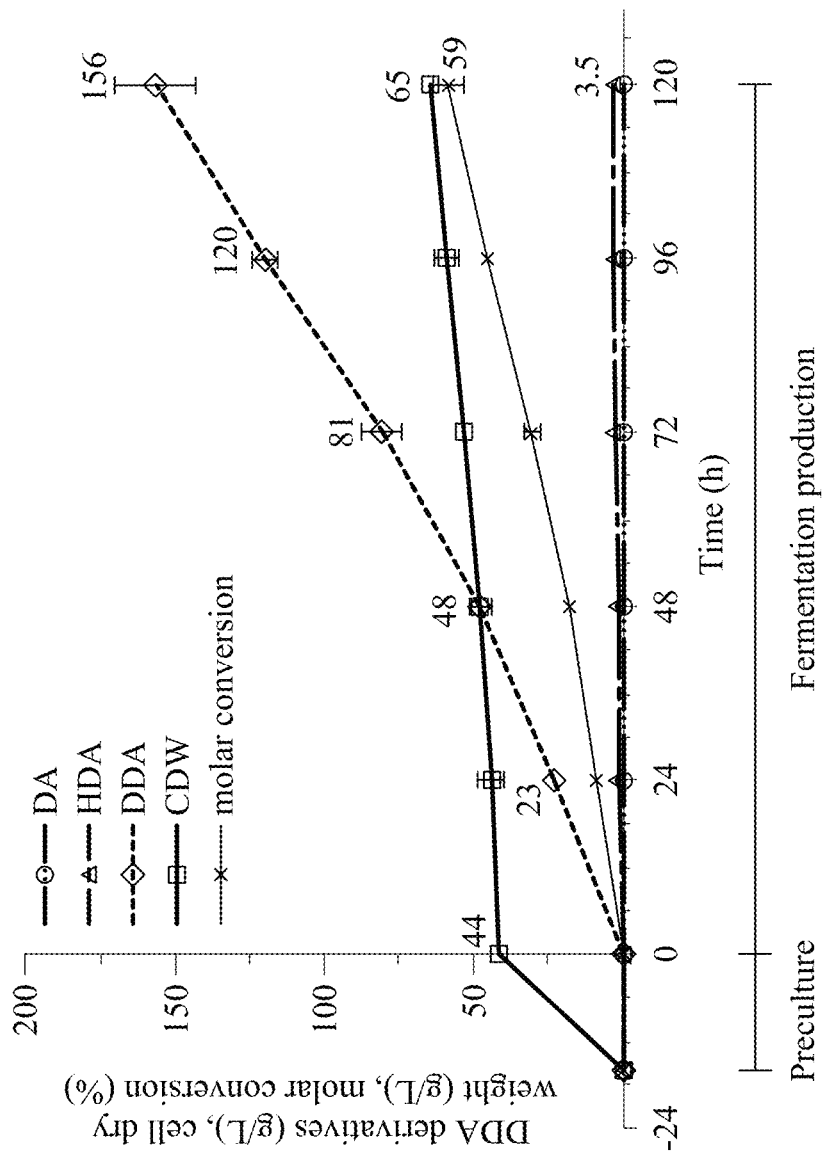
FIG. 10F shows analytical results of titer of dodecanedioic acid by fermentation production of P-19C strain of the present disclosure.

Reference is made to FIG. 10E and FIG. 10F. FIG. 10E shows analytical results of titer of dodecanedioic acid by fermentation production of *Candida viswanathii*. FIG. 10F shows analytical results of titer of dodecanedioic acid by fermentation production of P-19C strain of the present disclosure. In order to evaluate the potential of the P-19C strain for large-scale production of DDA, the P-19C strain is inoculated and pre-cultured in a 3 L fermenter. After 16 hours, dodecane (3.6 g/h) and a feed solution (containing urea and glucose) are added in a fed-batch mode to induce DDA production. In addition, *Candida viswanathii* is cultured and induced in the same manner as Control. The results showed that the P-19C strain grows with similar rate and final cell dry weight (CDW) (65 g/L) but produces DDA at a faster rate (48 g/L) within 48 hours compared to Control. Thereafter, DDA production of P-19C strain increases nearly linear and reaches 156 g/L at 120 hours. The corresponding productivity (1.3 g/L/h) and molar conversion (59%) of P-19C strain are about 41% higher than those of *Candida viswanathii*.

3.2 Screening and Optimizing of Enzymes for Producing Dodecanedioic Acid and Establishing of a Transformant for Producing Dodecanedioic Acid In *Candida viswanathii*, long-chain fatty alcohol oxidase 2 (FAO2) participates in the step of catalyzing the regeneration of long-chain alcohols into corresponding dicarboxylic acids through a series of oxidation reactions. The expression of FAO2 can be transiently induced by long-chain alkanes, but then sharply down-regulated, which affects the metabolic pathways that produce dicarboxylic acids. Therefore, a linear fragment co-expressing the FAO2 gene, the CYP52A19 gene and the CPRb gene is constructed to optimize the production of DDA. Since the linear fragment of Example 32 (p-19C) with the highest titer of DDA is very large (about 18.9 kb), integration of the FAO2 gene into Example 32 (p-19C) for co-integration of the CYP52A19 gene, the CPRb gene and the FAO2 gene is an extremely challenge. In order to solve the problem, the first gene editing fragment and the second gene editing fragment are designed experimentally, and different from the gene editing system of *Candida viswanathii* according to the aforementioned embodiment completing the recombination before transformation, the first gene editing fragment and the second gene editing fragment are recombined after being co-transformed into *Candida viswanathii* in this embodiment.

Figure 11A:
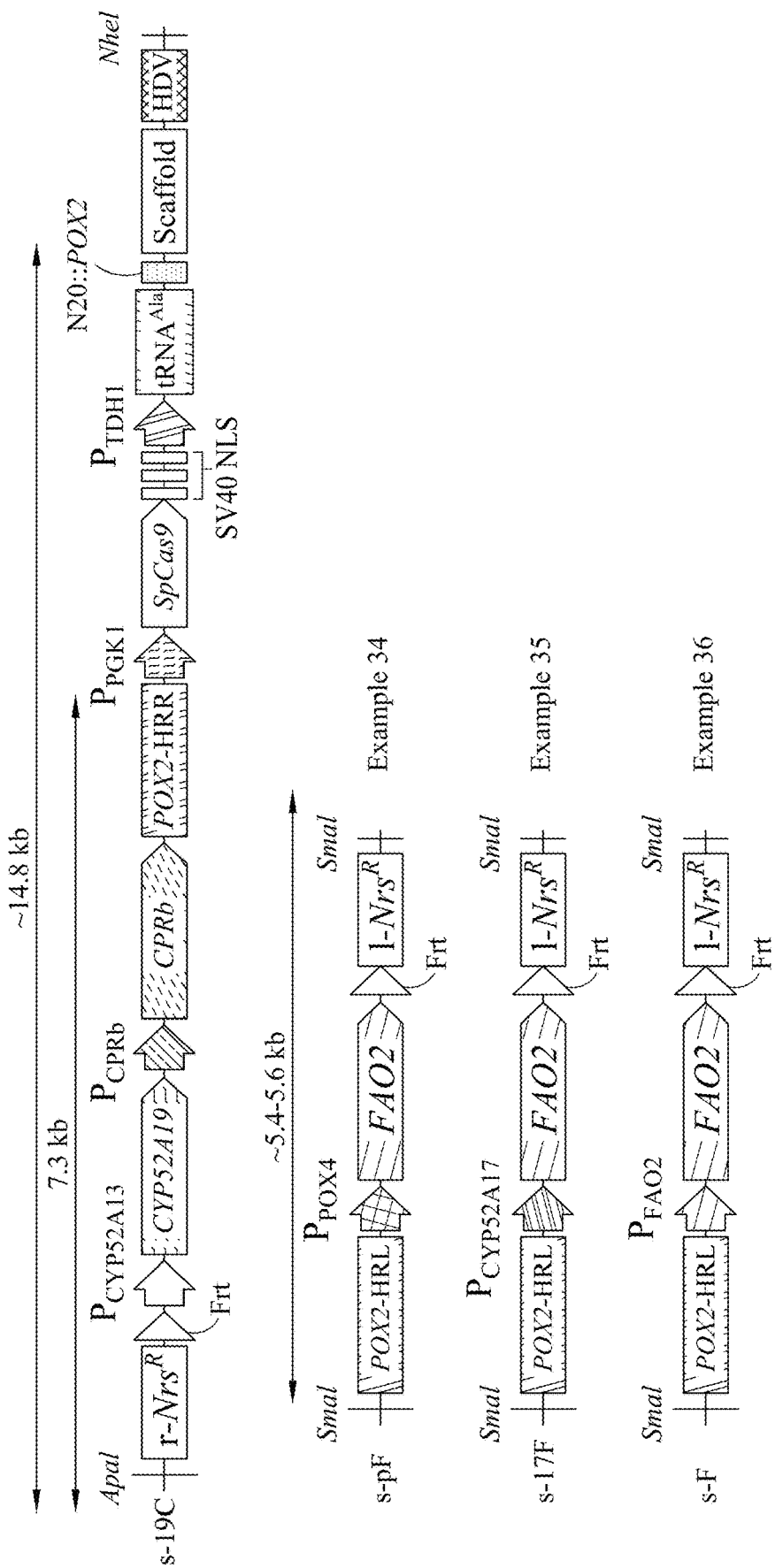
FIG. 11A is a schematic view showing constructions of expression cassettes of Example 34 to Example 36 of the present disclosure for screening enzymes of the long-chain alcohol oxidation pathway.
Figure 11B:
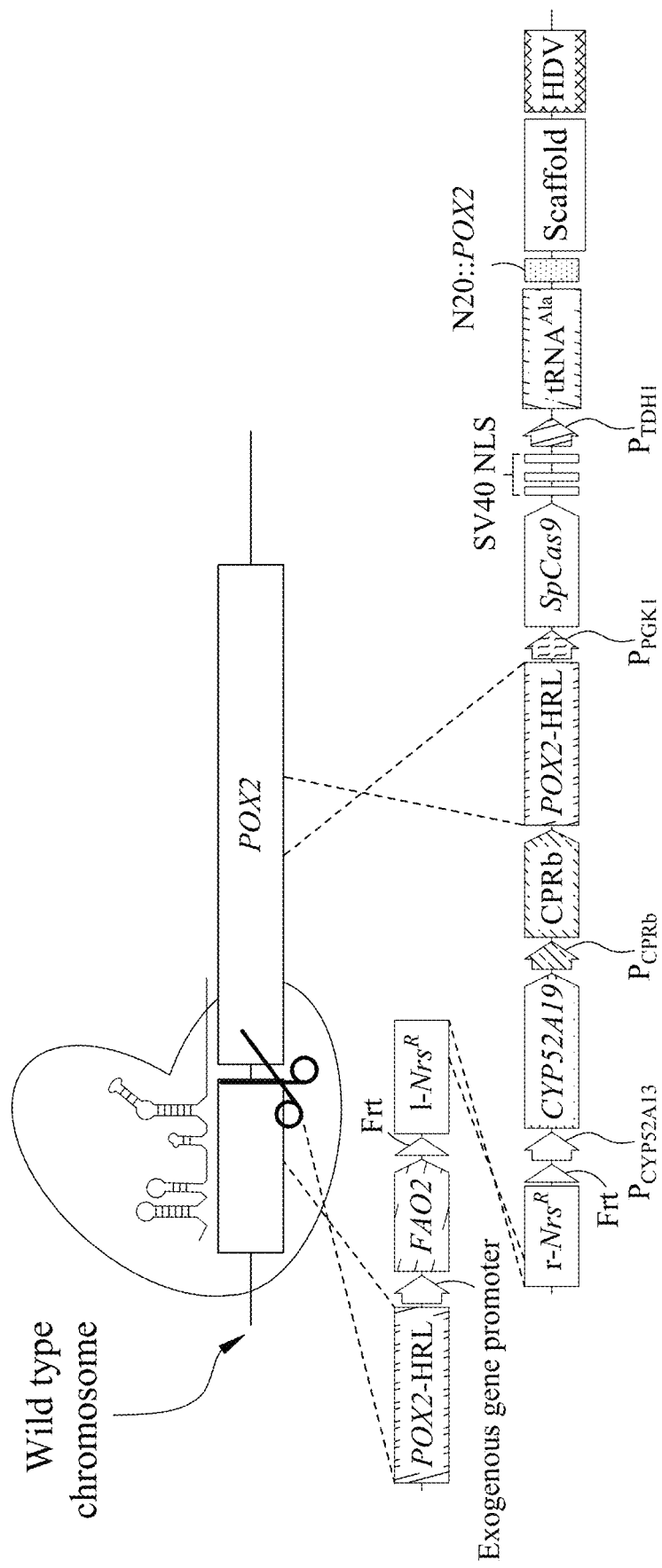
FIG. 11B is a schematic view showing the gene editing system of *Candida viswanathii* of the present disclosure constructing Example 34 to Example 36 in *Candida viswanathii*.

Reference is made to FIG. 11A, FIG. 11B and FIG. 14B. FIG. 11A is a schematic view showing constructions of expression cassettes of Example 34 (s-pF), Example 35 (s-17F) and Example 36 (s-F) of the present disclosure for screening enzymes of the long-chain alcohol oxidation pathway, and FIG. 11B is a schematic view showing the gene editing system of *Candida viswanathii* of the present disclosure constructing Example 34 to Example 36 in *Candida viswanathii*. FIG. 14B shows Table 3 listing SEQ ID NOs and their corresponding genes referred in FIG. 11B. Examples 34 to 36 are experimentally constructed as the first gene editing fragment, which successively included the first homology arm (represented as POX2-HRL in FIG. 11A and FIG. 11B), an expression cassette for optimizing the long-chain alcohol oxidation pathway and a first screening gene fragment (represented as 1-Nrs$^R$ in FIG. 11A and FIG. 11B). In the expression cassette for optimizing the long-chain alcohol oxidation pathway, three different exogenous gene promoters are used to drive the FAO2 gene of the sequence referenced as SEQ ID NO: 46 (represented as FAO2 in FIG. 11A and FIG. 11B), and the exogenous gene promoter is selected from Ppox4 of the sequence referenced as SEQ ID NO: 47, $P_{CYP52A17}$ of the sequence referenced as SEQ ID NO: 48 and $P_{FAO2}$ of the sequence referenced as SEQ ID NO: 49. Example 34 (s-pF) expressing the FAO2 gene under Ppox4, Example 35 (s-17F) expressing the FAO2 gene under $P_{CYP52A17}$ and Example 36 (s-F) expressing the FAO2 gene under $P_{FAO2}$ are constructed. The second gene editing fragment (represented as s-19C in FIG. 11A) is similar to Example 32 (p-19C), but segment from the first homology arm (represented as POX2-HRL in FIG. 11A and FIG. 11B) to the Nrs$^R$ gene is replaced by a second screening gene fragment (represented as r-Nrs$^R$ in FIG. 11A and FIG. 11B). The second screening gene fragment has a homologous fragment (not shown) that is homologous to part of the Nrs$^R$ gene, and the homologous fragment is about 400 bp.

The first screening gene fragment and the second screening gene fragment share the homologous fragment that is homologous to part of the Nrs$^R$ gene. Therefore, when the first gene editing fragment and the second first gene editing fragment are simultaneously electroporated into *Candida viswanathii*, the first gene editing fragment and the second gene editing fragment are recombined by the homologous fragment homologous to part of the Nrs$^R$ gene. The CRISPR-Cas9 system can simultaneously integrate the expression cassettes expressing the CYP52A19 gene, the CPRb gene and the FAO2 gene into the POX2 gene of *Candida viswanathii*, which can be used to overcome the problem that DNA size of the gene editing fragment to be integrated is too large.

Figure 11C:
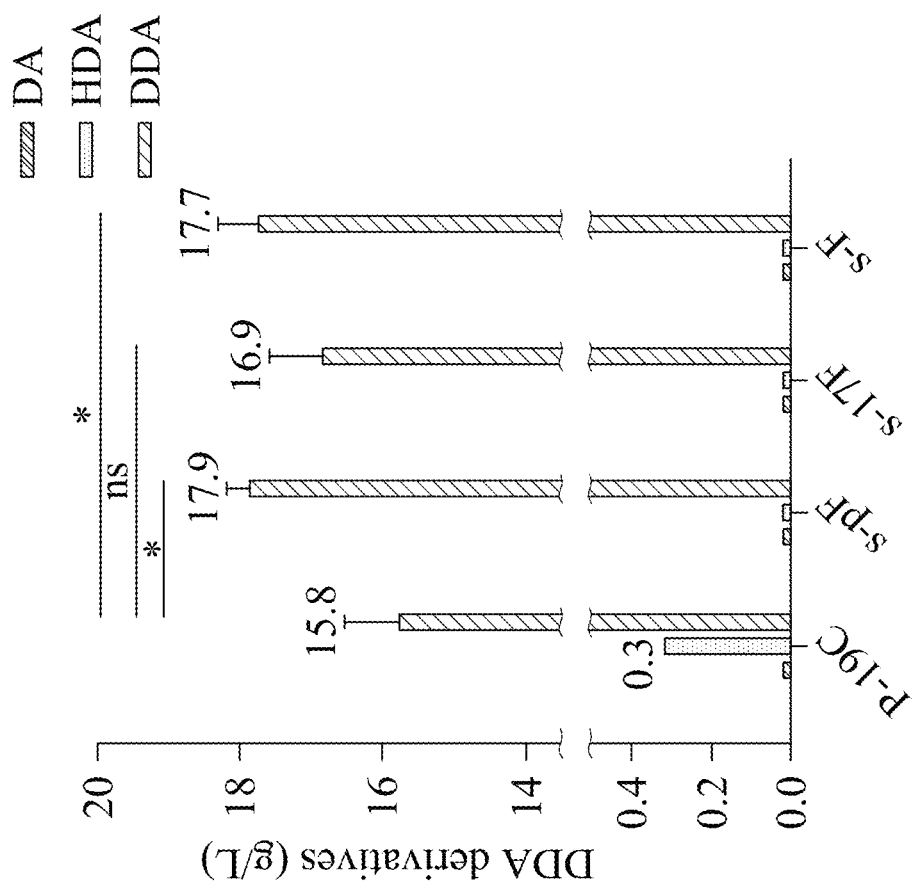
FIG. 11C shows analytical results of titer of dodecanedioic acid from culture supernatants of Example 34 to Example 36 of the present disclosure cultured in shake flasks.
Figure 11D:
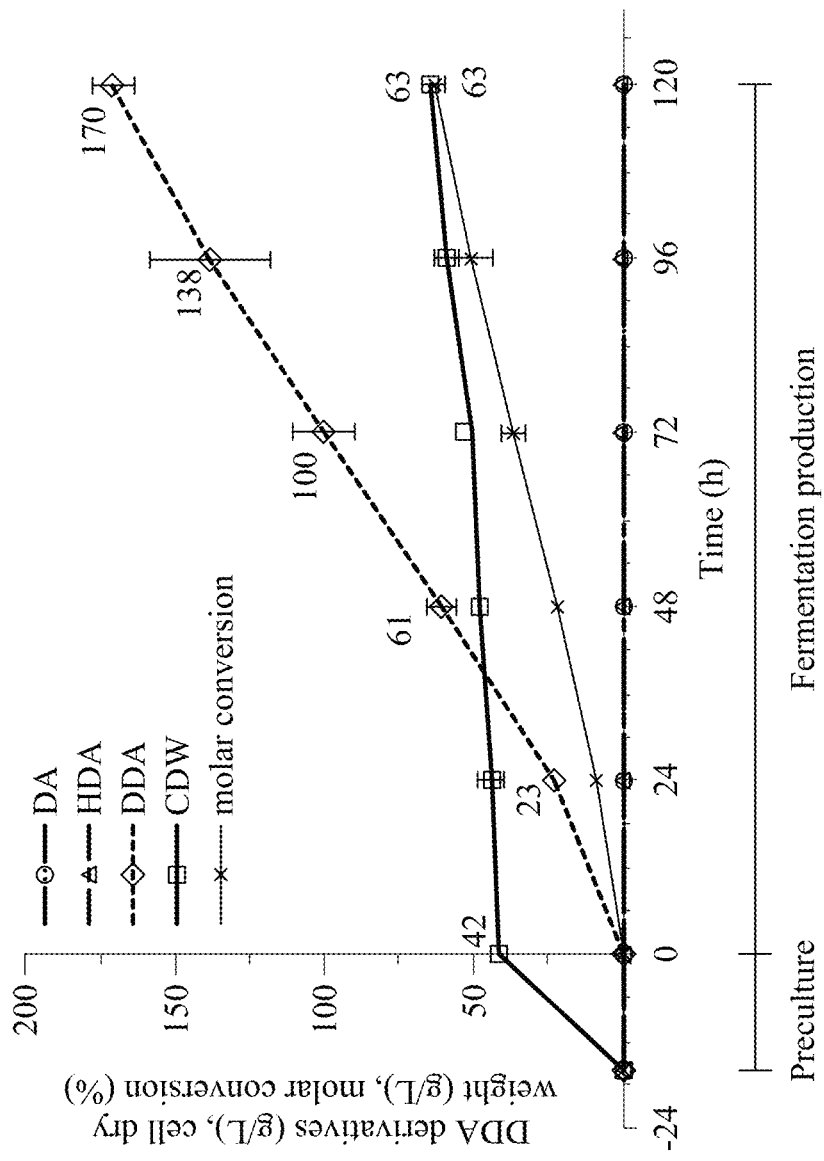
FIG. 11D shows analytical results of titer of dodecanedioic acid by fermentation production of PF19C strain of the present disclosure.

Reference is made to FIG. 11C and FIG. 11D. FIG. 11C shows analytical results of titer of dodecanedioic acid from culture supernatants of Example 34 to Example 36 of the present disclosure cultured in shake flasks, and FIG. 11D shows analytical results of titer of dodecanedioic acid by fermentation production of PF19C strain of the present disclosure. After 24 hours of shake flask culture, compared with the titer of DDA (15.8 g/L) produced by P-19C strain only expressing the CYP52A19 gene and the CPRb gene, the three transformants that transformed Example 34 (s-pF), Example 35 (s-17F) or Example 36 (s-F) all can yield higher DDA (16.9-17.9 g/L) than P-19C strain. Especially titer of the DDA (17.9 g/L) of the transformant (PF19C strain) that transformed Example 34 (s-pF) increases by 13% more than the P-19C strain. In order to evaluate the potential of PF19C strain to produce DDA on a large scale, PF19C strain is cultured in the 3 L fermenter. Compared with P-19C strain, PF19C strain grows at similar rate, and produces 170 g/L DDA and barely detectable intermediate HDA at 120 hours of fermentation production. The molar conversion rate is slightly increased to 63%, and the productivity reaches about 1.42 g/L/h.

The aforementioned results show that the gene editing system of *Candida viswanathii* of the present disclosure and uses thereof for co-expression of the exogenous genes of the enzyme producing dodecanedioic acid (the CYP52A19 gene and the CPRb gene) combined with the exogenous genes of enzymes of the long-chain alcohol oxidation pathway (the FAO2 gene) can significantly enhance oxidation reaction steps that converts HDA to DDA. Therefore, the gene editing system of *Candida viswanathii* of the present disclosure and uses thereof can be easily applied to the screening of enzymes to establish a stable transformant for producing dodecanedioic acid. And further, large fragments can be efficiently integrated into the gene of *Candida viswanathii* by the CRISPR-Cas9 system of split editing fragments.

Figure 12A:
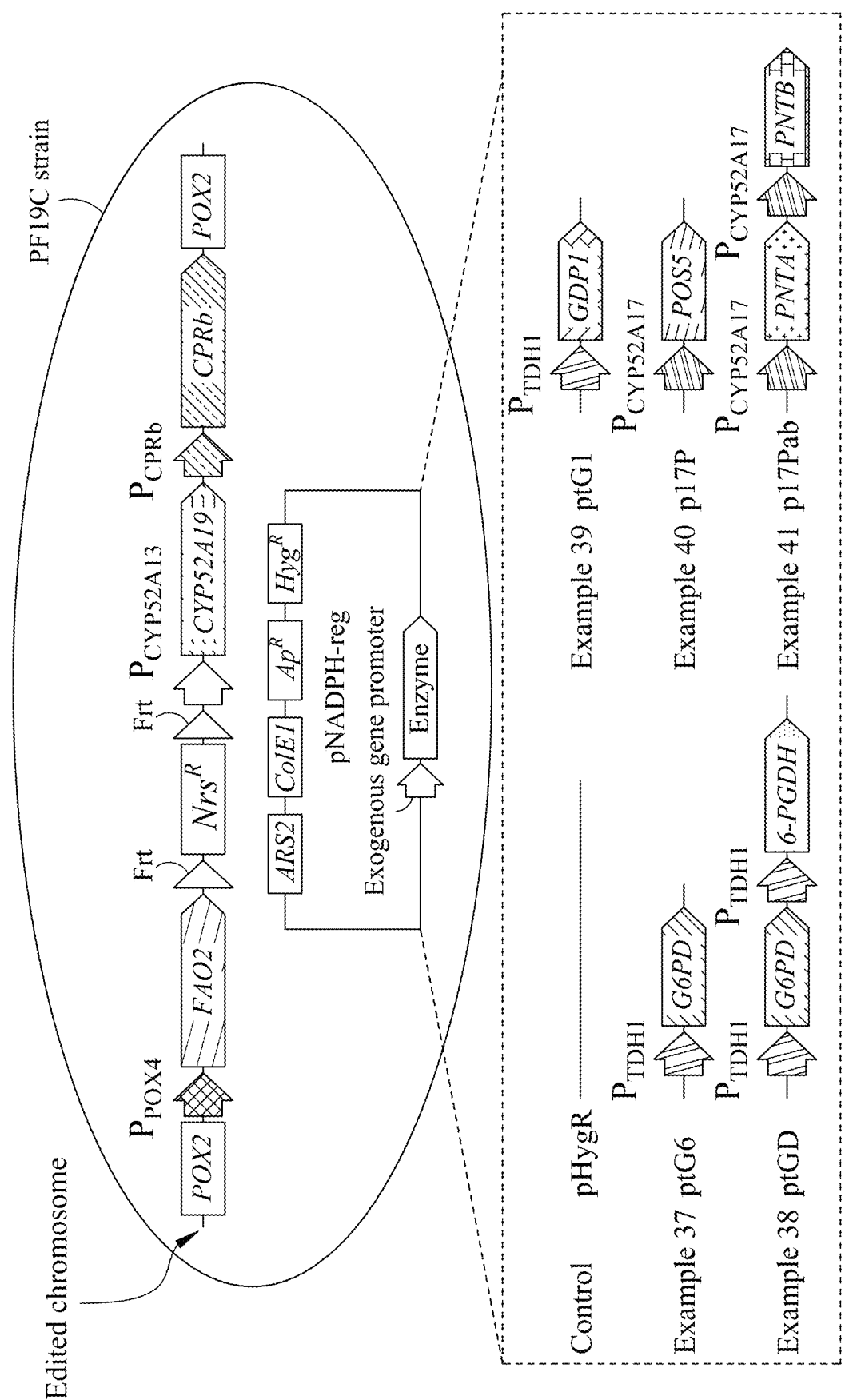
FIG. 12A is a schematic view showing constructions of expression cassettes of Example 37 to Example 41 of the present disclosure for screening enzymes of nicotinamide adenine dinucleotide phosphate (NADPH)-regenerating pathway.
Figure 12B:
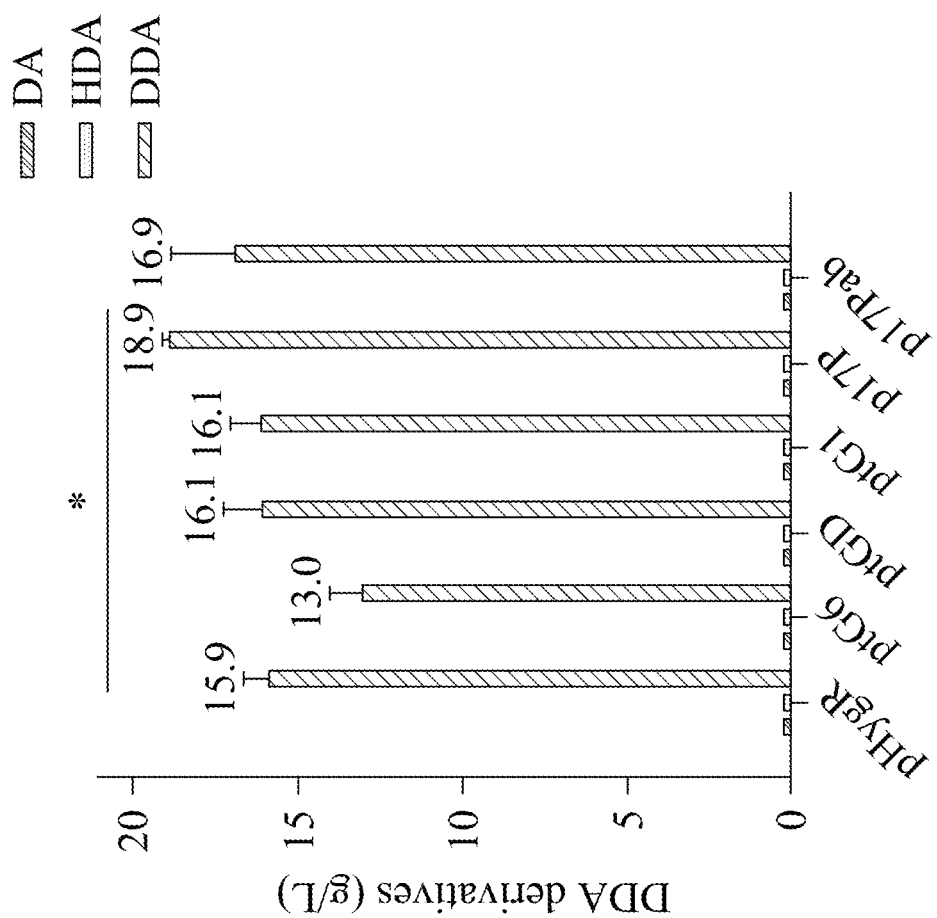
FIG. 12B shows analytical results of titer of dodecanedioic acid from culture supernatants of Example 37 to Example 41 of the present disclosure cultured in shake flasks.

Reference is made to FIG. 12A, FIG. 12B and FIG. 14B. FIG. 12A is a schematic view showing constructions of expression cassettes of Example 37 (ptG6), Example 38 (ptGD), Example 39 (ptG1), Example 40 (p17P) and Example 41 (p17Pab) of the present disclosure for screening enzymes of NADPH-regenerating pathway. FIG. 12B shows analytical results of titer of dodecanedioic acid from culture supernatants of Example 37 to Example 41 of the present disclosure cultured in shake flasks. FIG. 14B shows Table 3 listing SEQ ID NOs and their corresponding genes referred in FIG. 12A. The transformants for producing dodecanedioic acid established in this test example are all based on the extension of the metabolic pathway catalyzed by CYP and CPRb. In the catalytic process, CYP and CPR irreversibly and continuously consume NADPH as a cofactor, and the reaction goes downstream in the metabolic pathway. Therefore, NADPH regeneration enhancement is necessary to establish a more stable and continuous transformant for producing dodecanedioic acid. In *Candida viswanathii*, NADPH can be regenerated by activating endogenous glucose 6-phosphate dehydrogenase (the G6DP gene of the sequence referenced as SEQ ID NO: 50, represented as G6DP in FIG. 12A), 6-phosphogluconate dehydrogenase (the 6-PGDH gene of the sequence referenced as SEQ ID NO: 51, represented as 6-PGDH in FIG. 12A) or NADH kinase (the POS5 gene of the sequence referenced as SEQ ID NO: 52, represented as POS5 in FIG. 12A); or by activating exogenous glyceraldehyde-3-phosphate dehydrogenase 1 (the GDP1 gene of the sequence referenced as SEQ ID NO: 53, represented as GDP1 in FIG. 12A) or transhydrogenase (the PNTA gene or the PNTB gene, in which the PNTA gene of the sequence referenced as SEQ ID NO: 54 and represented as PNTA in FIG. 12A, and the PNTB gene of the sequence referenced as SEQ ID NO: 55 and represented as PNTB in FIG. 12A). A plasmid template pNADPH-reg is experimentally constructed to express an exogenous gene promoter and one of the above-mentioned enzymes, and then transformed into PF19C strain as Example 37 to Example 41 to screen the expression cassette having better performance of the exogenous gene promoter and enzyme driving NADPH regeneration. PF19C strain expressing the Hyg$^R$ gene (represented as Hyg$^R$ in FIG. 12A) but not expressing the expression cassette is used as Control. After 24 hours of shake flask culture, compared with the titer of DDA (15.9 g/L) of Control, the titer of DDA (18.9 g/L) of Example 40 (p17P) expressing the POS5 gene (represented by POS5 in FIG. 12A) under $P_{CYP52A17}$ is significantly higher than that of Control. The titer of DDA of other Examples is comparable with Control.

The aforementioned results indicate that the gene editing system of *Candida viswanathii* of the present disclosure and uses thereof to express the POS5 gene driven by $P_{CYP52A17}$ can effectively catalyze the regeneration of NADPH and further improve the production of DDA.

Figure 13A:
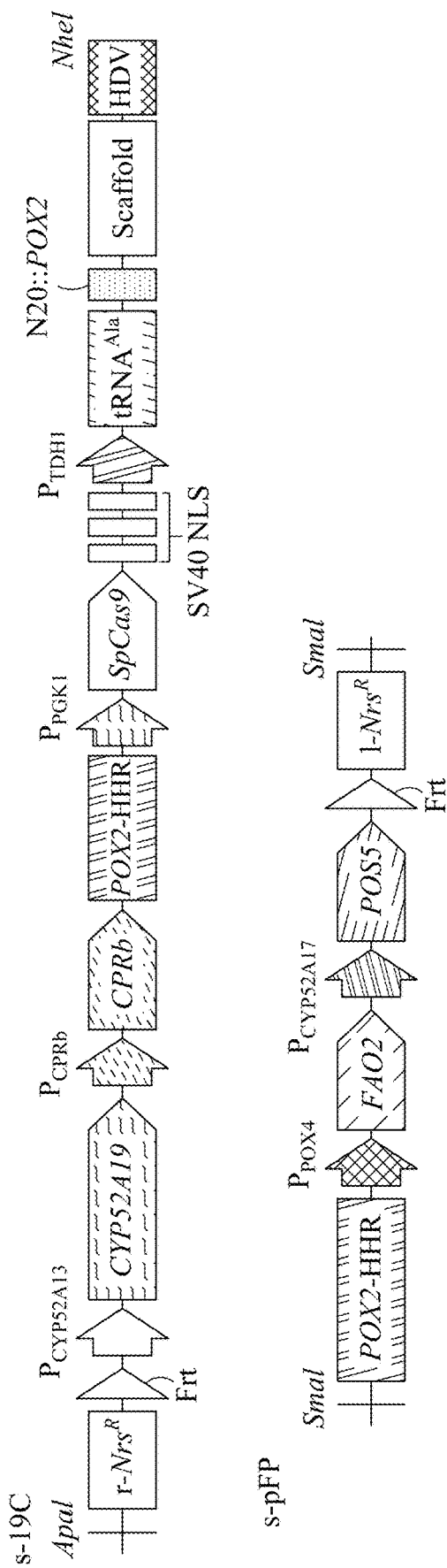
FIG. 13A is a schematic view showing construction of PFP19C strain of the present disclosure.
Figure 13B:
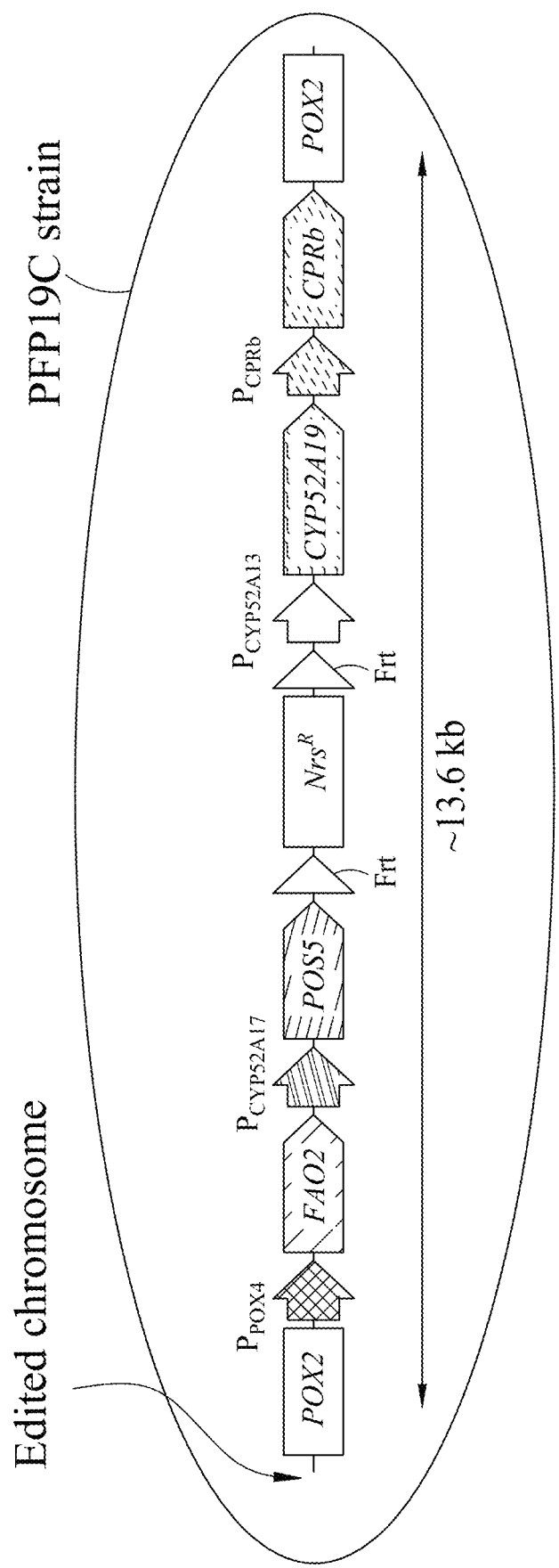
FIG. 13B is a schematic view showing the edited chromosome of the PFP19C strain of the present disclosure.
Figure 13C:
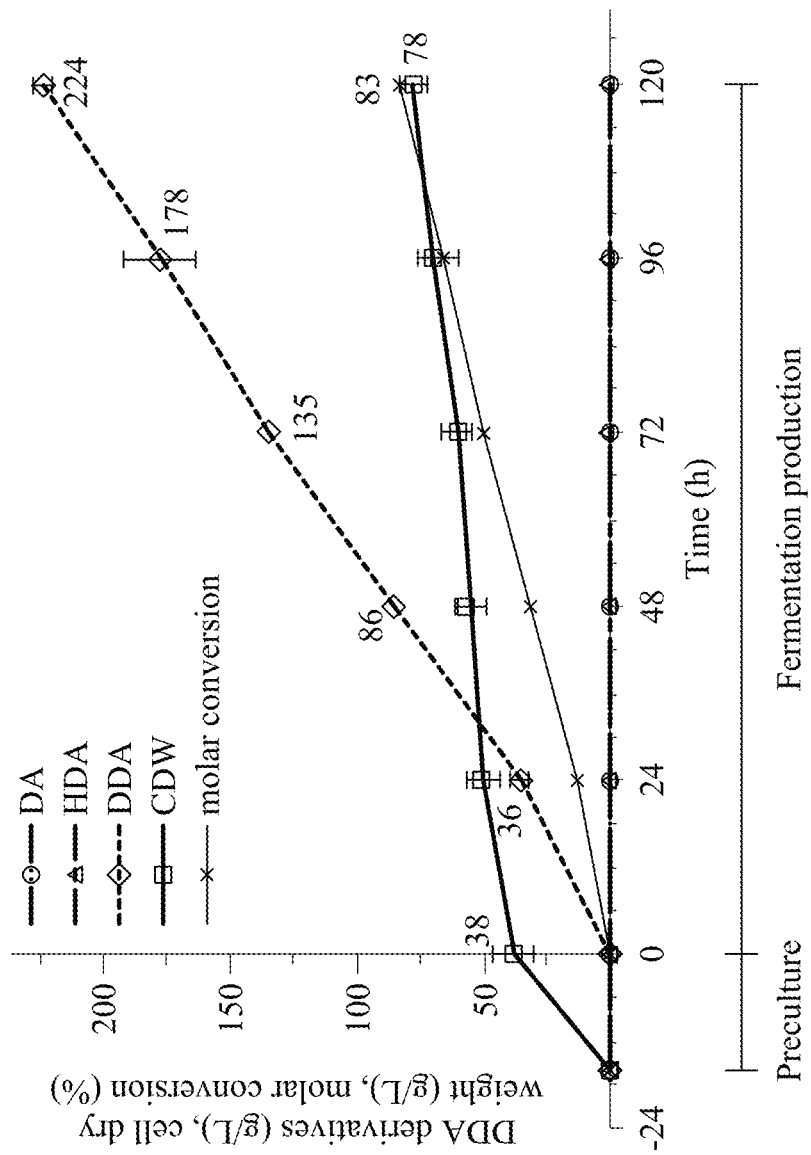
FIG. 13C shows analytical results of titer of dodecanedioic acid by fermentation production of PFP19C strain of the present disclosure.

Reference is made to FIG. 13A to FIG. 13C. FIG. 13A is a schematic view showing construction of PFP19C strain of the present disclosure, FIG. 13B is a schematic view showing the edited chromosome of the PFP19C strain of the present disclosure, and FIG. 13C shows analytical results of titer of dodecanedioic acid by fermentation production of PFP19C strain of the present disclosure. In view of the above results, the CYP52A19 gene (represented as CYP52A19 in FIG. 13A and FIG. 13B), the CPRb gene (represented as CPRb in FIG. 13A and FIG. 13B), the FAO2 gene (represented as FAO2 in FIG. 13A and FIG. 13B) and the POS5 gene (represented as POS5 in FIG. 13A and FIG. 13B) are further co-integrated into the POX2 gene (represented as POX2 in FIG. 13B) of Candida viswanathii to construct a transformant for producing dodecanedioic acid (PFP19C strain). Then the established transformants are cultured in the 3 L fermenter to produce DDA. Unlike Candida viswanathii that has a lag phase and grows slowly after induction, PFP19C strain grows at 120 hours to reach 78 g/L dry cell weight (CDW) and produces DDA reaching 224 g/L at 120 hours with a nearly linear rate. Remarkably, the molar conversion concurrently increased to 83% with no detectable intermediate byproducts and the productivity reached 1.87 g/L/h. Overall, PFP19C accumulates the biomass needed for growth faster in the fermenter and produced about 102% more DDA than parent Candida viswanathii.

The above results indicate that the transformant for producing dodecanedioic acid constructed by the gene editing of Candida viswanathii of the present disclosure and use thereof can not only integrate a large gene editing fragment of about 13.6 kb into the genome of Candida viswanathii, the growth rate of the transformant for producing dodecanedioic acid can be significantly improved by co-expressing the POS5 gene, and the titer, the productivity, product purity and molar conversion of DDA produced by the oxidation reaction of dodecane can also be improved. Thus, the result verify the potential and feasibility of applying the gene editing system of Candida viswanathii of the present disclosure and the gene editing method thereof to construct the transformant for producing dodecanedioic acid.

In addition, please refer to Table 1, which is the comparison of titer of dodecanedioic acid by fermentation production between the transformant for producing dodecanedioic acid of the present disclosure established in the test examples and Candida viswanathii.

TABLE 1

| Strain | exogenous gene integrated | Titer (g/L) HDA | Titer (g/L) DDA | Molar conversion (%) | Productivity (g/L/h) |
|---|---|---|---|---|---|
| Candida viswanathii | None | 2.8 | 111 | 42 | 0.93 |
| P-19C | CYP52A19 gene, CPRb gene | 3.5 | 156 | 59 | 1.3 |
| PF19C | CYP52A19 gene, CPRb gene, FAO2 gene | 0 | 170 | 63 | 1.42 |
| PFP19C | CYP52A19 gene, CPRb gene, FAO2 gene, POS5 gene | 0 | 224 | 83 | 1.87 |

The results in Table 1 show that the gene editing system of Candida viswanathii of the present disclosure and the gene editing method thereof co-express the CYP52A18 gene or the CYP52A19 gene driven by the endogenous promoter or P CYP52A13 and the CPRb gene driven by $P_{CPRb}$, which can significantly increase the production of DDA produced by Candida viswanathii. Furthermore, to further improve the titer, product purity, molar conversion rate and productivity of DDA, P-19C strain is constructed by integrating the above-mentioned exogenous gene into the POX2 gene of Candida viswanathii to block the w-hydroxylation pathway. Compared with Candida viswanathii, P-19C strain can increase the DDA production from 111 g/L to 156 g/L, and achieve a productivity of 1.3 g/L/h and a molar conversion of 59%. In addition, the gene editing system of Candida viswanathii of the present disclosure and the gene editing method thereof can be used in different optimization strategies to further construct the transformant for producing dodecanedioic acid, without being limited by the size of the gene editing target. For example, PF19C strain in which the FAO2 gene, the CYP52A19 gene, and the CPRb gene are co-integrated into the POX2 gene of Candida viswanathii is constructed to strengthen the oxidation pathway for converting long-chain alcohols to dicarboxylic acids, and PFP19C strain in which the POS5 gene, the FAO2 gene, the CYP52A19 gene and the CPRb gene are co-integrated into the of the POX2 gene of Candida viswanathii to further enhance NADPH regeneration. Thereby, the transformant for producing dodecanedioic acid of the present disclosure can finally effectively convert 200 g/L dodecane to 224 g/L DDA at a productivity of 1.87 g/L/h and a molar conversion rate of 83%, and there is almost no detectable by-product HDA. The above results indicate that the transformant for producing dodecanedioic acid and the method for producing dodecanedioic acid established by the gene editing system of Candida viswanathii of the present disclosure have high genome stability, high product selectivity and high substrate conversion rate. The results also verify the potential of the gene editing system of Candida viswanathii of the present disclosure and uses thereof in the field of the gene editing of Candida viswanathii and continuous production of DDA.

To sum up, the gene editing system of Candida viswanathii of the present disclosure and gene editing method thereof is the disclosure of firstly establishing the CRISPR-Cas9 system in Candida viswanathii. By screening the exogenous gene promoters, adjusting the combination of the first ribozyme and the second ribozyme and the recombination strategy of optimizing the homology arm can effectively overcome the operational difficulties and low recombination rate encountered in the conventional editing of Candida viswanathii with diploid. Thereby, the success rate and accuracy of gene editing of Candida viswanathii can be greatly increased to 60%, and gene editing methods such as deletion, mutation, replacement or fragment insertion can be easily and quickly realized without being affected by fragment size or insertion site, so as to obtain a gene-edited strain of Candida viswanathii that can be stably subcultured. Therefore, the gene editing system of Candida viswanathii of the present disclosure and the gene editing method thereof can be further applied to the construction of transformants for producing chemicals as a cell factory to participate in the sustainable economy of chemicals.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A transformant for producing dodecanedioic acid, comprising:
   a host cell, wherein the host cell is *Candida viswanathii*; and
   at least three exogenous genes, wherein the at least three exogenous genes comprise a CYP52A19 gene, a CPRb gene and a FAO2 gene, and the at least three exogenous genes are integrated into a chromosome of the host cell.

2. The transformant for producing dodecanedioic acid of claim 1, wherein the at least three exogenous genes are integrated into a POX2 gene of the chromosome of the host cell.

3. The transformant for producing dodecanedioic acid of claim 2, wherein the at least three exogenous genes comprise a POS5 gene.

4. A method for producing dodecanedioic acid, comprising:
   providing a reaction substrate, wherein the reaction substrate comprises dodecane; and
   performing a fermentation step, wherein the reaction substrate is inoculated with the transformant for producing dodecanedioic acid of claim 1, and then is cultured at a fermentation condition for a fermentation time to obtain a fermented substance, and the fermented substance comprises dodecanedioic acid.

5. The transformant for producing dodecanedioic acid of claim 1, wherein the at least three exogenous genes are integrated in the chromosome of the host cell using a gene editing system, and the gene editing system comprises:
   a first gene editing fragment, which successively comprises a first homology arm and a screening gene; and
   a second gene editing fragment connected to a C-terminus of the first gene editing fragment, which successively comprises a second homology arm, a Cas9 expression cassette and a sgRNA cassette, wherein the Cas9 expression cassette successively comprises a Cas9 promoter, a Cas9 gene and three nuclear localization sequences, the sgRNA cassette successively comprises a sgRNA promoter, a first ribozyme, a targeting sequence, a scaffold and a second ribozyme, and the first gene editing fragment and the second gene editing fragment are constructed as a linear fragment for gene editing of the chromosome of the host cell;
   wherein the first homology arm and the second homology arm respectively correspond to a specific fragment of a gene on the chromosome of the host cell, and the targeting sequence corresponds to a specific sequence of the gene on the chromosome of the host cell;
   wherein the first gene editing fragment and/or the second gene editing fragment comprise the at least three exogenous genes.

6. The transformant for producing dodecanedioic acid of claim 5, wherein the Cas9 promoter is $P_{PGK1}$, and the sgRNA promoter is $P_{TDH1}$.

7. The transformant for producing dodecanedioic acid of claim 6, wherein the first ribozyme is $tRNA^{Ala}$ having the sequence of SEQ ID NO: 12, and the second ribozyme is hepatitis delta virus (HDV) having the sequence of SEQ ID NO: 11.

8. The transformant for producing dodecanedioic acid of claim 5, wherein the screening gene of the first gene editing fragment further comprises a first screening gene fragment, the second gene editing fragment further comprises a second screening gene fragment at an N-terminus of the second homology arm, the first screening gene fragment has a homologous fragment, the second screening gene fragment has the homologous fragment, and the first screening gene fragment and the second screening gene fragment are recombined into the linear fragment by the homologous fragment of the first screening gene fragment and the homologous fragment of the second screening gene fragment.

* * * * *